United States Patent
Calderini et al.

(10) Patent No.: US 8,648,201 B2
(45) Date of Patent: Feb. 11, 2014

(54) AMINOPYRIDINE DERIVATIVES FOR TREATING TUMORS AND INFLAMMATORY DISEASES

(75) Inventors: Michel Calderini, Darmstadt (DE); Margarita Wucherer-Plietker, Messel (DE); Ulrich Graedler, Weinheim (DE); Christina Esdar, Mainz (DE)

(73) Assignee: MERCK PATENT GmbH, Darmstadt (DE)

( * ) Notice: Subject to any disclaimer, the term of this patent is extended or adjusted under 35 U.S.C. 154(b) by 0 days.

(21) Appl. No.: 13/383,605

(22) PCT Filed: Jun. 17, 2010

(86) PCT No.: PCT/EP2010/003659
§ 371 (c)(1),
(2), (4) Date: Jan. 12, 2012

(87) PCT Pub. No.: WO2011/006567
PCT Pub. Date: Jan. 20, 2011

(65) Prior Publication Data
US 2012/0115861 A1 May 10, 2012

(30) Foreign Application Priority Data

Jul. 15, 2009 (DE) .......................... 10 2009 033 208

(51) Int. Cl.
*C07D 401/14* (2006.01)
*C07D 413/06* (2006.01)
*A61K 31/4439* (2006.01)
*A61K 31/5355* (2006.01)

(52) U.S. Cl.
USPC ..... 546/273.4; 544/106; 544/114; 514/234.5; 514/333

(58) Field of Classification Search
USPC .......................... 544/106; 546/273.4; 514/333
See application file for complete search history.

(56) References Cited

U.S. PATENT DOCUMENTS

2007/0254868 A1  11/2007  Lauffer et al.

FOREIGN PATENT DOCUMENTS

| WO | WO 2004/069160 A2 | 8/2004 |
| WO | WO-2007/111904 | * 10/2007 |
| WO | WO 2007/111904 A2 | 10/2007 |

OTHER PUBLICATIONS

Gamo et al., Nature, vol. 465, p. 305-310 (2010).*
International Search Report of PCT/EP2010/003659 (Oct. 15, 2010).
F.J. Gamo et al., "Thousands of Chemical Starting Points for Antimalarial Lead Identification", Nature, vol. 465 (May 20, 2010) XP002600760, pp. 305-310.
Database Chembl-Ntd [Online] XP002605207—Database Accession No. 527649 (May 20, 2010).
Database Chembl-Ntd [Online] XP002605208—Database Accession No. 530945 (May 20, 2010).
Database Chembl-Ntd [Online] XP002605209—Database Accession No. 524805 (May 20, 2010).
Database Chembl-Ntd [Online] XP002605210—Database Accession No. 542271 (May 20, 2010).
Database Chembl-Ntd [Online] XP002605211—Database Accession No. 525200 (May 20, 2010).

* cited by examiner

*Primary Examiner* — Yong Chu
*Assistant Examiner* — Sonya Wright
(74) *Attorney, Agent, or Firm* — Millen, White, Zelano & Branigan, P.C.

(57) ABSTRACT

Compounds of the formula (I), in which $R^1$, $R^2$, $R^3$, $R^4$, $R^7$ and Y have the meanings indicated in Claim 1, are inhibitors of PDK1 and cell proliferation/cell vitality and can be employed for the treatment of tumors and for the treatment of inflammatory diseases.

14 Claims, No Drawings

AMINOPYRIDINE DERIVATIVES FOR TREATING TUMORS AND INFLAMMATORY DISEASES

The invention relates to compounds of the formula I

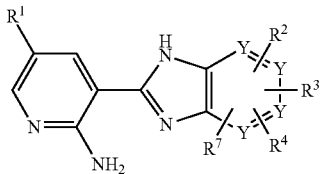

in which
$R^1$ denotes a mono- or bicyclic saturated, unsaturated or aromatic heterocycle having 1 to 4 N, O and/or S atoms, which may be unsubstituted or mono- or disubstituted by Hal, A, $OR^5$, $SR^5$, $NO_2$, CN, $NR^5COA$, $NR^5SO_2A$, $SO_2N(R^5)_2$, $S(O)_mA$, $[C(R^5)_2]_nCOOR^5$, $[C(R^5)_2]_nCON(R^5)_2$, $[C(R^5)_2]_nCONR^5[C(R^5)_2]_nAr$, $[C(R^5)_2]_nCONR^5[C(R^5)_2]_nHet$, $[C(R^5)_2]_nCO$-Het, $[C(R^5)_2]_nN(R^5)_2$, $[C(R^5)_2]_nAr$, $[C(R^5)_2]_nHet$, $O[C(R^5)_2]_nN(R^5)_2$, $O[C(R^5)_2]_nHet$, $NR^5COOA$, $NR^5CON(R^5)_2$, $NR^5COO[C(R^5)_2]_nN(R^5)_2$, $NR^5COO[C(R^5)_2]_nHet^1$, $NR^5CONR^5[C(R^5)_2]_nN(R^5)_2$, $NR^5CONR^5[C(R^5)_2]_nHet^1$, $OCONR^5[C(R^5)_2]_nN(R^5)_2$, $OCONR^5[C(R^5)_2]_nHet^1$, $[C(R^5)_2]_nOR^5$, $[C(R^5)_2]_nCONR^5[C(R^5)_2]_nN(R^5)_2$, CHO, COA, =S, =NH, =NA and/or =O (carbonyl oxygen),
Y, independently of one another, denotes N or C, where a maximum of two Y may denote N,
$R^2$, $R^3$, $R^4$, $R^7$ each, independently of one another, denote H, Hal, A, OA, $SR^5$, $NO_2$, CN, $NR^5COA$, $NR^5SO_2A$, $SO_2N(R^5)_2$, $S(O)_mA$, $S(O)_mHet$, CO—Ar, CO-Het, $[C(R^5)_2]_nAr$, $[C(R^5)_2]_nHet$, $C(R^5)(OR^5)Ar$, $C(R^5)(OR^5)Het$, $[C(R^5)_2]_nOR^5$, $[C(R^5)_2]_nOAr$, $[C(R^5)_2]_nOHet$, $[C(R^5)_2]_nN(R^5)_2$, $[C(R^5)_2]_nCON(R^5)_2$, $[C(R^5)_2]_nCOOR^5$, $[C(R^5)_2]_nCONR^5[C(R^5)_2]_nAr$, $[C(R^5)_2]_nCONR^5[C(R^5)_2]_nHet$, $[C(R^5)_2]_nCOO[C(R^5)_2]_nAr$, $[C(R^5)_2]_nCOO[C(R^5)_2]_nHet$, $[C(R^5)_2]_nNR^5CO[C(R^5)_2]_nAr$ or $[C(R^5)_2]_nNR^5CO[C(R^5)_2]_nHet$,
with the proviso that
a) if one Y denotes N, $R^7$ is absent;
b) if two Y denote N, $R^4$ and $R^7$ are absent;
two adjacent radicals
selected from the group $R^2$, $R^3$, $R^4$, $R^7$
together also denote $OCH_2O$, $OCH_2CH_2O$, NHCONH, $OCF_2O$, CH=N—NH or NH—N=CH,
$R^5$ denotes A or H,
A denotes unbranched or branched alkyl having 1-10 C atoms, in which 1-7 H atoms may be replaced by F and/or in which one or two $CH_2$ groups may be replaced by O, S, $NR^5$ and/or by CH=CH groups,
or cyclic alkyl having 3-7 C atoms,
Ar denotes phenyl, naphthyl or biphenyl, each of which is unsubstituted or mono-, di- or trisubstituted by Hal, A, $OR^5$, $N(R^5)_2$, $SR^5$, $NO_2$, CN, $COOR^5$, $CON(R^5)_2$, $NR^5COA$, $NR^5SO_2A$, $SO_2N(R^5)_2$, $S(O)_mA$, CO-$Het^1$, $Het^1$, $O[C(R^5)_2]_nN(R^5)_2$, $O[C(R^5)_2]_nHet^1$, NHCOOA, $NHCON(R^5)_2$, $NHCOO[C(R^5)_2]_nN(R^5)_2$, $NHCOO[C(R^5)_2]_nHet^1$, $NHCONH[C(R^5)_2]_nN(R^5)_2$, $NHCONH[C(R^5)_2]_nHet^1$, $OCONH[C(R^5)_2]_nN(R^5)_2$, $OCONH[C(R^5)_2]_nHet^1$ and/or COA,
Het denotes a mono- or bicyclic saturated, unsaturated or aromatic heterocycle having 1 to 4 N, O and/or S atoms, which may be unsubstituted or mono- to trisubstituted by Hal, A, $OR^5$, $N(R^5)_2$, $SR^5$, $NO_2$, CN, $COOR^5$, $CON(R^5)_2$, $NR^5COA$, $NR^5SO_2A$, $SO_2N(R^5)_2$, $S(O)_mA$, CO-$Het^1$, $Het^1$, $[C(R^5)_2]_nN(R)_2$, $[C(R^5)_2]_nHet^1$, $O[C(R^5)_2]_nN(R^5)_2$, $O[C(R^5)_2]_nHet^1$, NHCOOA, $NHCON(R^5)_2$, NHCOO[C$(R^5)_2]_nN(R^5)_2$, $NHCOO[C(R^5)_2]_nHet^1$, $NHCONH[C(R^5)_2]_nN(R^5)_2$, $NHCONH[C(R^5)_2]_nHet^1$, $OCONH[C(R^5)_2]_nN(R^5)_2$, $OCONH[C(R^5)_2]_nHet^1$, CO-$Het^1$, CHO, COA, =S, =NH, =NA and/or =O (carbonyl oxygen),
$Het^1$ denotes a monocyclic saturated heterocycle having 1 to 2 N and/or O atoms, which may be mono- or disubstituted by A, OA, OH, Hal and/or =O (carbonyl oxygen),
Hal denotes F, Cl, Br or I,
m denotes 0, 1 or 2,
n denotes 0, 1, 2, 3 or 4,
and pharmaceutically usable salts, tautomers and stereoisomers thereof, including mixtures thereof in all ratios.

The compounds of the formula I according to the invention also include the pharmaceutically usable derivatives and solvates thereof.

The invention was based on the object of finding novel compounds having valuable properties, in particular those which can be used for the preparation of medicaments.

It has been found that the compounds of the formula I and salts and/or solvates thereof have very valuable pharmacological properties while being well tolerated.

In particular, they exhibit a cell proliferation/cell vitality-inhibiting action as antagonists or agonists. The compounds according to the invention can therefore be used for the combating and/or treatment of tumours, tumour growth and/or tumour metastases.

The antiproliferative action can be tested in a proliferation assay/vitality assay.

Other pyridine and pyrazine derivatives for the treatment of cell-proliferative diseases are described in WO 2009/05337 A2.

Other aminoheteroaryl compounds are described as kinase inhibitors for combating cancer in WO 2006/021886, WO 2007/111904 and WO 2004/069160.

Other heterocyclic compounds are known from WO 2009/053737, WO 2009/126003 and US 2009/0197862.

Accordingly, the compounds according to the invention or a pharmaceutically acceptable salt thereof are administered for the treatment of cancer, including solid carcinomas, such as, for example, carcinomas (for example of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The compounds are furthermore suitable for the treatment of immune deficiency induced by HIV-1 (Human Immunodeficiency Virus Type 1).

Cancer-like hyperproliferative diseases are to be regarded as brain cancer, lung cancer, squamous epithelial cancer, bladder cancer, stomach cancer, pancreatic cancer, liver cancer, renal cancer, colorectal cancer, breast cancer, head cancer, neck cancer, oesophageal cancer, gynaecological cancer, thyroid cancer, lymphomas, chronic leukaemia and acute leukaemia. In particular, cancer-like cell growth is a disease which represents a target of the present invention. The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and to a process for the treatment of the said diseases comprising the administration of one or more compounds according to the invention to a patient in need of such an administration.

It can be shown that the compounds according to the invention have an antiproliferative action. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both the prevention of diseases and the treatment of pre-existing conditions. The prevention of proliferation/vitality is achieved by administration of the compounds according to the invention prior to the development of overt disease, for example for preventing tumour growth. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in vitro testing. Typically, a culture of the cell is incubated with a compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined.

The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

There are many diseases associated with deregulation of cell proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, perianastomatic prosthetic restenosis, restenosis after angioplasty or stent placement, and the like.

The compounds of the formula I, also act as regulators, modulators or inhibitors of protein kinases, in particular of the serine/threonine kinase type, which include, inter alia, phosphoinositide-dependent kinase 1 (PDK1). The compounds according to the invention exhibit a certain action in the inhibition of the serine/threonine kinase PDK1.

PDK1 phosphorylates and activates a sub-group of the AGC protein kinase family, comprising PKB, SGK, S6K and PKC isoforms. These kinases are involved in the PI3K signal transduction pathway and control basic cellular functions, such as survival, growth and differentiation. PDK1 is thus an important regulator of diverse metabolic, proliferative and life-sustaining effects.

Diseases caused by protein kinases are characterised by anomalous activity or hyperactivity of such protein kinases. Anomalous activity relates to either: (1) expression in cells which do not usually express these protein kinases; (2) increased kinase expression, which results in undesired cell proliferation, such as cancer; (3) increased kinase activity, which results in undesired cell proliferation, such as cancer, and/or in hyperactivity of the corresponding protein kinases. Hyperactivity relates either to amplification of the gene which encodes for a certain protein kinase, or the generation of an activity level which can be correlated with a cell proliferation disease (i.e. the severity of one or more symptoms of the cell proliferation disease increases with increasing kinase level). The bioavailability of a protein kinase may also be influenced by the presence or absence of a set of binding proteins of this kinase.

The most important types of cancer that can be treated using a compound according to the invention include colorectal cancer, small-cell lung cancer, non-small-cell lung cancer, multiple myeloma as well as renal cell carcinoma and endometrium carcinoma, particularly also types of cancer in which PTEN is mutated, inter alia breast cancer, prostate cancer and glioblastoma.

In addition, the compounds according to the invention can be used to achieve additive or synergistic effects in certain existing cancer chemotherapies and radiotherapies and/or to restore the efficacy of certain existing cancer chemotherapies and radiotherapies.

The compounds of the formula I, also act as regulators, modulators or inhibitors in the expression and/or functioning of proteins which play a role in inflammatory diseases, immune response regulation or cell proliferation.

The present invention relates to compounds which modulate interleukin-1 (IL-1) receptor-associated kinase (IRAK) and are useful in the prevention or treatment of inflammatory, cell-proliferative and immune-related conditions and diseases. The invention also relates to pharmaceutical compositions which comprise these compounds and the use of the compounds and compositions in question for the prevention or treatment of conditions or diseases mediated by IRAK.

The importance of IL-1 in inflammation has been demonstrated by the ability of the highly specific IL-1 receptor antagonist protein (IL-1Ra or IRAP) to relieve inflammatory conditions (for a review, see, for example, Dinarello (1997) *Cytokine Growth Factor Rev.* 8:253-265).

IL-1 treatment of cells induces the formation of a complex consisting of the two IL-1 receptor chains, IL-1R1 and IL-1 RAcP, and the resultant heterodimer recruits an adaptor molecule designated as MyD88 (Wesche et al. (1999) *J. Biol. Chem.* 274:19403-19410). MyD88 binds to a protein called IRAK (IL-1 receptor-associated kinase) (see, O'Neill et al. (1998) *J. Leukoc. Biol.* 63(6):650-657, Auron (1998) *Cytokine Growth Factor Rev.* 9(3-4):221-237 and O'Neill (2000) *Biochem. Soc. Trans.* 28(5)557-563, for review articles). IRAK is subsequently phosphorylated and released from the receptor complex to interact with a tumour necrosis factor receptor-associated factor, TRAF6, which transduces the signal to downstream effector molecules (Cao et al. (1996) *Nature* 383:443-446). TRAF6 can trigger the NIK/IKK kinase cascade to activate the transcription factor NF-κB. NF-κB regulates a number of genes which themselves regulate the immune and inflammatory responses.

Four IRAKs have been identified: IRAK-1 (Cao, et al. (1996) *Science* 271:1128-1131), IRAK-2 (Muzio, et al. (1997) *Science* 278:1612-1615), monocyte-specific IRAK-M, also known as IRAK-3 (Wesche, et al. (1999) *J. Biol. Chem.* 274:19403-10), and IRAK-4 (PCT Publication No. WO 01/051641). IRAK proteins have been shown to play a role in transducing signals other than those originating from the IL-1 receptors, including signals triggered by the activation of IL-18 receptors (Kanakaraj et al. (1999) *J. Exp. Med.* 189(7):1129-1138) and LPS receptors (Yang et al. (1999) *J. Immunol.* 163:639-643; Wesche et al. (1999) *J. Biol. Chem.* 274:19403-19410). Overexpression of IRAK-2 and IRAK-M has been shown to be capable of reconstituting the response to IL-1 and LPS in an IRAK-deficient cell line.

As used herein, the term "IRAK" refers to an interleukin—1 (IL-1) receptor-associated kinase protein or a variant thereof that is capable of mediating a cellular response to IL-1 in vitro or in vivo. IRAK may be kinase-active or kinase-inactive proteins. Examples of kinase-active IRAKs include IRAK-1 and IRAK-4. Examples of kinase-inactive IRAKs include IRAK-2 and IRAK-3 (also known as IRAK-M). Kinase-active IRAKs may be capable of trans-phosphorylation of other proteins or autophosphorylation. In preferred embodiments, IRAK is IRAK-1 and/or IRAK-4.

IRAK variants include proteins which are substantially homologous to native IRAK, i.e. proteins having one or more naturally or non-naturally occurring amino acid deletions, insertions or substitutions (for example IRAK derivatives, homologues or fragments). The amino acid sequence of an IRAK variant is preferably at least 80% identical to native IRAK, more preferably at least about 90% identical and even more preferably at least about 95% identical.

The terms "signal transduction", "signalling" and related terms refer to a process in which an extracellular signal (for example the concentration of a cytokine, hormone, neurotransmitter, growth factor) are transmitted via a cascade of intracellular protein-protein interactions to the cell nucleus and generate one or more cell responses (for example gene transcription, protein secretion, mitosis, apoptosis). The interaction of an extracellular signalling molecule (for example a cytokine, a hormone, a neurotransmitter, a growth factor) with one or more transmembrane protein receptors on the cell surface can activate one or more signal transduction pathways. The protein-protein interactions in a signal transduction pathway may be multivalent and include covalent and/or non-covalent protein modifications. An intracellular signalling molecule, i.e. a signal transducing protein or a signal transducer, may be involved in one or more signal transduction pathways. As described herein, protein-protein interactions include direct and indirect interactions.

As used herein, the expression "IRAK-responsive condition or disorder" and related expressions and terms relate to a condition or disorder that responds favourably to modulation of IRAK activity. Favourable responses to IRAK modulation include alleviation or elimination of the disease and/or its accompanying symptoms, inhibition of a disease, i.e. arrest or reduction of the development of the disease or its clinical symptoms, and regression of the disease or its clinical symptoms. An IRAK-responsive condition or disease may be completely or partially responsive to IRAK modulation. An IRAK-responsive condition or disorder may be associated with inappropriate, for example less than or greater than normal, IRAK activity. Inappropriate functional IRAK activity may arise as a consequence of IRAK expression in cells which normally do not express IRAK, decreased IRAK expression (which results in, for example lipid and metabolic disorders and diseases) or decreased IRAK expression. An IRAK-responsive condition or disease may include any IRAK-mediated condition or disease defined below.

As used herein, the expression "IRAK-mediated condition or disorder" and related expressions and terms relate to a condition or disorder characterised by inappropriate, for example less than or greater than normal, IRAK activity. Inappropriate functional IRAK activity may arise as a consequence of IRAK expression in cells which normally do not express IRAK, decreased IRAK expression or a degree of intracellular activation (resulting in, for example inflammatory and autoimmune disorders and diseases) or decreased IRAK expression. An IRAK-mediated condition or disorder may be completely or partially mediated by inappropriate functional IRAK activity. However, an IRAK-mediated condition or disorder is one in which modulation of IRAK results in an effect on the underlying condition or disorder (for example an IRAK inhibitor results in an improvement in patient well-being in at least some patients).

The term "modulates" relates to the ability of a compound to increase or decrease the function and/or expression of IRAK, where IRAK function may include kinase activity and/or protein binding. Modulation may occur in vitro or in vivo. Modulation, as described herein, includes the inhibition or activation of IRAK function and/or the downregulation or upregulation of IRAK expression, either directly or indirectly. A modulator preferably activates IRAK function and/or upregulates IRAK expression. More preferably, a modulator activates or inhibits IRAK function and/or upregulates or downregulates IRAK expression. Most preferably, a modulator inhibits IRAK function and/or down-regulates IRAK expression. The ability of a compound to inhibit IRAK function can be demonstrated in enzymatic assays or cell-based assays (for example inhibition of IL-1-stimulated NF-κB activation).

Diseases or conditions, including chronic diseases, of humans or other species can be treated or prevented with inhibitors of IRAK function. These diseases or conditions include (1) inflammatory or allergic diseases, such as, for example, systemic anaphylaxis and hypersensitivity responses, drug allergies, insect sting allergies and food allergies, (2) inflammatory bowel diseases, such as, for example, Crohn's disease, ulcerative colitis, ileitis and enteritis, (3) vaginitis, (4) psoriasis and inflammatory dermatoses, such as, for example, dermatitis, eczema, atopic dermatitis, allergic contact dermatitis and urticaria, (5) vasculitis, (6) spondyloarthropathies, (7) scleroderma, (8) asthma and respiratory allergic diseases, such as allergic asthma, allergic rhinitis, allergic conjunctivitis, hypersensitivity lung diseases and the like, and (9) autoimmune diseases, such as, for example, arthritis (including rheumatoid and psoriatic), systemic lupus erythematosus, type I diabetes, glomerulonephritis and the like, (10) transplant rejection (including allograft rejection and transplant-versus-host diseases), (11) other diseases in which undesired inflammatory diseases are to be inhibited, for example atherosclerosis, myositis, neurological disorders, such as strokes, ischaemic reperfusion injuries, open head traumas and close head traumas, neurodegenerative diseases (for example Parkinson's disease), multiple sclerosis, Alzheimer's disease, encephalitis, meningitis, osteoporosis, gout, hepatitis, nephritis, gall bladder diseases, sepsis, sarcoidosis, conjunctivitis, otitis, chronic obstructive pulmonary disease, sinusitis and Behcet's syndrome; (12) cell proliferative or neoplastic diseases, such as, for example, breast, skin, prostate, cervix, uterus, ovary, testes, bladder, lung, liver, larynx, oral cavity, colon cancer or cancer of the gastrointestinal tract (for example oesophagus, stomach, pancreas), brain, thyroid, blood or lymphatic system and diseases in which angiogenesis and neovascularisation play a role, (13) metabolic disorders that are sensitive to inhibition of TNF or IL-1 signalling, such as, for example, obesity, type II diabetes, metabolic syndrome, insulin resistance, hyperglycaemia, hyperuricaemia, hyperinsulinaemia, cachexia, hypercholesterolaemia, hyperlipidaemia, dyslipidaemia, mixed dyslipidaemia and hypertriglyceridaemia, eating disorders, such as anorexia nervosa and bulimia, (14) infectious diseases, for example bacteraemia and septic shock; (15) cardiovascular disorders, such as, for example, acute heart failure, hypotension, hypertension, angina pectoris, myocardial infarction, cardiomyopathy, congestive heart failure, atherosclerosis, coronary arterial diseases, restenosis and vascular stenosis, and (16) immune diseases and conditions.

In one embodiment, the present methods are directed to the treatment or prevention of diseases or conditions selected from rheumatoid arthritis, septic shock, inflammatory bowel diseases, bone mass loss, cancer, dermal sensitisation disorders, diabetes, obesity, ischaemic stroke, ischaemic reperfusion injury, head trauma, asthma, allergic diseases, multiple sclerosis and trans-plant rejection.

Other heterocyclic compounds are described as IRAK inhibitors for combating inflammatory diseases in U.S. Pat. No. 7,132,438 B2 or U.S. Pat. No. 7,199,119 B2.

Compounds of the formula I are also taken to mean the hydrates and solvates of these compounds, furthermore pharmaceutically usable derivatives.

The invention also relates to the optically active forms (stereoisomers), salts, the enantiomers, the racemates, the diastereomers and the hydrates and solvates of these compounds. Solvates of the compounds are taken to mean adductions of inert solvent molecules onto the compounds which form owing to their mutual attractive force. Solvate are, for example, mono- or dihydrates or alcoholates.

Pharmaceutically usable derivatives are taken to mean, for example, the salts of the compounds according to the invention and also so-called prodrug compounds.

Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I and pharmaceutically usable salts, tautomers and stereoisomers thereof, characterised in that
a) a compound of the formula II

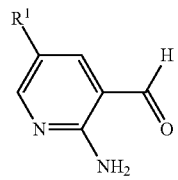

II in which $R^1$ has the meaning indicated in Claim 1, is reacted with a compound of the formula III

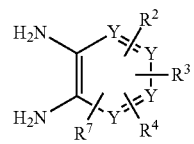

III in which Y, $R^2$, $R^3$, $R^4$, $R^7$ have the meanings indicated in Claim 1,
or
b) a compound of the formula IV

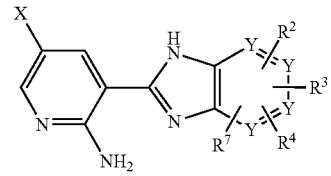

IV in which Y, $R^2$, $R^3$, $R^4$, $R^7$ have the meanings indicated in Claim 1 and X denotes Br or I,
is reacted with a compound of the formula V $R^1$-L    V in which $R^1$ has the meaning indicated in Claim 1 and
L denotes a boronic acid or boronic acid ester radical,
and/or a base or acid of the formula I is converted into one of its salts.

Above and below, the radicals $R^1$, $R^2$, $R^3$, $R^4$, $R^7$ and Y have the meanings indicated for the formula I, unless expressly indicated otherwise. For all radicals which occur more than once, their meanings are independent of one another.

ABBREVIATIONS

Ac acetyl
BOC tert-butoxycarbonyl
CBZ or Z benzyloxycarbonyl
DCCl dicyclohexylcarbodiimide
DMF dimethylformamide
EDCl N-ethyl-N,N'-(dimethylaminopropyl)carbodiimide
Et ethyl
Fmoc 9-fluorenylmethoxycarbonyl
HOBt 1-hydroxybenzotriazole Me methyl
Mtr 4-methoxy-2,3,6-trimethylphenylsulfonyl
HONSu N-hydroxysuccinimide
OBut tert-butyl ester
Oct octanoyl
OMe methyl ester
OEt ethyl ester
POA phenoxyacetyl
PPA polyphosphoric acid
TFA trifluoroacetic acid
Trt trityl(triphenylmethyl).

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

One or two $CH_2$ groups in A may also be replaced by N, O or S atoms and/or by —CH=CH— groups. A thus also denotes, for example, 2-methoxyethyl or 2-hydroxyethyl.

A furthermore denotes cyclic alkyl, preferably cyclopropyl, cyclobutyl, cyclopentyl, cyclohexyl or cycloheptyl.

A furthermore preferably denotes unbranched or branched alkyl having 1-10 C atoms, in which one $CH_2$ group may be replaced by an O atom and/or, in addition, 1-5 H atoms may be replaced by F.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-methylaminosulfonylphenyl, o-, m- or p-aminocarbonylphenyl, o-, m- or p-carboxyphenyl, o-, m- or p-methoxycarbonylphenyl, o-, m- or p-ethoxycarbonylphenyl, o-, m- or p-acetylphenyl, o-, m- or p-cyanophenyl, o-, m- or p-acetaminophenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl.

Ar preferably denotes phenyl which is unsubstituted or mono-, di- or trisubstituted by Hal and/o $NR^5COA$.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-etrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated. Unsubstituted Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)-phenyl or also 3,4-dihydro-2H-1,5-benzodioxepin-6- or -7-yl, furthermore preferably 2,3-dihydrobenzofuranyl or 2,3-dihydro-2-oxofuranyl.

Het furthermore preferably denotes a mono- or bicyclic saturated, unsaturated or aromatic heterocycle having 1 to 4 N, O and/or S atoms, which may be unsubstituted or mono- to trisubstituted by A, $COOR^5$ and/or =O (carbonyl oxygen).

Het particularly preferably denotes piperidinyl, 4,5-dihydropyridazinyl, pyridyl, morpholinyl, piperazinyl, pyrrolidinyl, tetrahydrofuranyl, 1,3-oxazinanyl, thienyl, pyrazolyl, thiazolyl, benzofuranyl, isoxazolyl, benzothienyl, 3,4-dihydro-2H-pyrido[3,2-b]-1,4-oxazinyl, pyrrolyl, pyrimidinyl, furanyl, imidazolyl, oxazolyl, triazolyl, tetrazolyl, thiadiazole, pyridazinyl, pyrazinyl, indolyl, isoindolyl, benzimidazolyl, indazolyl, quinolyl, 1,3-benzodioxolyl, tetrahydroimidazolyl, tetrahydropyrazolyl, oxazolidinyl or isoxazolidinyl, each of which is unsubstituted or mono- or disubstituted by A, $COOR^5$ and/or =O (carbonyl oxygen).

$Het^1$ preferably denotes a monocyclic saturated heterocycle having 1 to 2 N and/or O atoms, which may be mono- or disubstituted by A and/or =O. $Het^1$ very particularly preferably denotes pyrrolidinyl, tetrahydroimidazolyl, tetrahydropyrazolyl, piperidinyl, morpholinyl, piperazinyl, oxazolidinyl or isoxazolidinyl, each of which is unsubstituted or mono- or disubstituted by A and/or =O.

Irrespective of further substitutions, $R^1$ denotes a mono- or bicyclic saturated, unsaturated or aromatic heterocycle having 1 to 4 N, O and/or S atoms, in which the heterocycle has the meanings as indicated above for Het.

$R^1$ preferably denotes a mono- or bicyclic saturated, unsaturated or aromatic heterocycle having 1 to 4 N, O and/or S atoms, which may be unsubstituted mono- or disubstituted by Hal, A, $OR^5$, CN, $[C(R^5)_2]_nCOOR^5$, $[C(R^5)_2]_nCON(R^5)_2$, $[C(R^5)_2]_nCONR^5[C(R^5)_2]_nAr$, $[C(R^5)_2]_nCONR^5[C(R^5)_2]_nHet$, $[C(R^5)_2]_nCO$-Het, $[C(R^5)_2]_nN(R^5)_2$, $[C(R^5)_2]_nAr$, $[C(R^5)_2]_nHet$, $[C(R^5)_2]_nOR^5$ and/or $[C(R^5)_2]_nCONR^5[C(R^5)_2]_nN(R^5)_2$.

R¹ particularly preferably denotes pyrazolyl, thiazolyl, thienyl, pyridyl, benzofuranyl, isoxazolyl, benzothienyl, 3,4-dihydro-2H-pyrido[3,2-b]-1,4-oxazinyl, pyrrolyl, pyrimidinyl, furanyl, imidazolyl, oxazolyl, triazolyl, tetrazolyl, thiadiazole, pyridazinyl, pyrazinyl, indolyl, isoindolyl, benzimidazolyl, indazolyl, quinolyl or 1,3-benzodioxolyl, each of which is unsubstituted or mono- or disubstituted by A, $CH_2COHet$, $(CH_2)_nOH$, $(CH_2)_nHet$, $CONH(CH_2)_nHet$, $(CH_2)_nNH_2$, OA, Hal, $(CH_2)_nNHA$, $(CH_2)_nNA_2$, $CH_2Ar$, $CH_2CONA_2$, $(CH_2)_nOA$, $(CH_2)_nCOOH$, $(CH_2)_nCOOA$, $CONH(CH_2)_2NA_2$, $CONH_2$, CONHA, $CONA_2$, $CONH(CH_2)_2OA$ and/or CN.

$R^2$, $R^3$, $R^4$, $R^7$, preferably denote, in each case independently of one another, H, Hal, A, OA, $SO_2N(R^5)_2$, $S(O)_mHet$, CO—Ar, $[C(R^5)_2]_nAr$, $[C(R^5)_2]_nHet$, $C(R^5)(OR^5)Ar$, $[C(R^5)_2]_nOR^5$, $[C(R^5)_2]_nOAr$, $[C(R^5)_2]_nN(R^5)_2$, $[C(R^5)_2]_nCON(R^5)_2$, $[C(R^5)_2]_nCOOR^5$, $[C(R^5)_2]_nCONR^5[C(R^5)_2]_nAr$, $[C(R^5)_2]_nCONR^5[C(R^5)_2]_nHet$ or $[C(R^5)_2]_nNR^5CO[C(R^5)_2]_nAr$, with the proviso that
a) if one Y denotes N, $R^7$ is absent;
b) if two Y denote N, $R^4$ and $R^7$ are absent;
two adjacent radicals
selected from the group $R^2$, $R^3$, $R^4$, $R^7$
together also denote $OCH_2O$, $OCH_2CH_2O$, NHCONH, $OCF_2O$, CH=N—NH or NH—N=CH.

$R^2$, $R^3$, $R^4$, $R^7$, particularly preferably denote, in each case independently of one another, H, $(CH_2)_nOH$, $(CH_2)_nOA$, $(CH_2)_nHet$, Hal, A, $SO_2NH_2$, $SO_2NHA$, $SO_2NA_2$, $(CH_2)_nAr$, CH(OH)Ar, $(CH_2)_nNHCO(CH_2)_nAr$, COAr, $(CH_2)_nCONH(CH_2)_nAr$, $(CH_2)_nCONH(CH_2)_nHet$, $(CH_2)_nCOOH$, $(CH_2)_nCOOA$, $(CH_2)_nCONH_2$, $(CH_2)_nCONHA$, $(CH_2)_nCONA_2$, $SO_2Het$, $(CH_2)_nNH_2$, $(CH_2)_nNHA$, $(CH_2)_nNA_2$, $(CH_2)_nOAr$ or $CONH(CH_2)_2OA$, with the proviso that
a) if one Y denotes N, $R^7$ is absent;
b) if two Y denote N, $R^4$ and $R^7$ are absent;
two adjacent radicals
selected from the group $R^2$, $R^3$, $R^4$, $R^7$
together also denote $OCH_2O$, $OCH_2CH_2O$, NHCONH, $OCF_2O$, CH=N—NH or NH—N=CH, Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ij, which conform to the formula I and in which the radicals not designated in greater detail have the meaning indicated for the formula I, but in which in Ia R¹ denotes a mono- or bicyclic saturated, unsaturated or aromatic heterocycle having 1 to 4 N, O and/or S atoms, which may be unsubstituted or mono- or disubstituted by Hal, A, $OR^5$, CN, $[C(R^5)_2]_nCOOR^5$, $[C(R^5)_2]_nCON(R^5)_2$, $[C(R^5)_2]_nCONR^5[C(R^5)_2]_nAr$, $[C(R^5)_2]_nCONR^5[C(R^5)_2]_nHet$, $[C(R^5)_2]_nCO-Het$, $[C(R^5)_2]_nN(R^5)_2$, $[C(R^5)_2]_nAr$, $[C(R^5)_2]_nHet$, $[C(R^5)_2]_nOR^5$ and/or $[C(R^5)_2]_nCONR^5[C(R^5)_2]_nN(R^5)_2$;

in Ib R¹ denotes pyrazolyl, thiazolyl, thienyl, pyridyl, benzofuranyl, isoxazolyl, benzothienyl, 3,4-dihydro-2H-pyrido[3,2-b]-1,4-oxazinyl, pyrrolyl, pyrimidinyl, furanyl, imidazolyl, oxazolyl, triazolyl, tetrazolyl, thiadiazole, pyridazinyl, pyrazinyl, indolyl, isoindolyl, benzimidazolyl, indazolyl, quinolyl or 1,3-benzodioxolyl, each of which is unsubstituted or mono- or disubstituted by A, $CH_2COHet$, $(CH_2)_nOH$, $(CH_2)_nHet$, $CONH(CH_2)_nHet$, $(CH_2)_nNH_2$, OA, Hal, $(CH_2)_nNHA$, $(CH_2)_nNA_2$, $CH_2Ar$, $CH_2CONA_2$, $(CH_2)_nOA$, $(CH_2)_nCOOH$, $(CH_2)_nCOOA$, $CONH(CH_2)_2NA_2$, $CONH_2$, CONHA, $CONA_2$, $CONH(CH_2)_2OA$ and/or CN;

in Ic $R^2$, $R^3$, $R^4$, $R^7$ each, independently of one another, denote H, Hal, A, OA, $SO_2N(R^5)_2$, $S(O)_mHet$, CO—Ar, $[C(R^5)_2]_nAr$, $[C(R^5)_2]_nHet$, $C(R^5)(OR^5)Ar$, $[C(R^5)_2]_nOR^5$, $[C(R^5)_2]_nOAr$, $[C(R^5)_2]_nN(R^5)_2$, $[C(R^5)_2]_nCON(R^5)_2$, $[C(R^5)_2]_nCOOR^5$, $[C(R^5)_2]_nCONR^5[C(R^5)_2]_nAr$, $[C(R^5)_2]_nCONR^5[C(R^5)_2]_nHet$ or $[C(R^5)_2]_nNR^5CO[C(R^5)_2]_nAr$ with the proviso that
a) if one Y denotes N, $R^7$ is absent;
b) if two Y denote N, $R^4$ and $R^7$ are absent;
two adjacent radicals
selected from the group $R^2$, $R^3$, $R^4$, $R^7$
together also denote $OCH_2O$, $OCH_2CH_2O$, NHCONH, $OCF_2O$, CH=N—NH or NH—N=CH;

in Id $R^2$, $R^3$, $R^4$, $R^7$ each, independently of one another, denote H, $(CH_2)_nOH$, $(CH_2)_nOA$, Het, Hal, A, $SO_2NH_2$, $SO_2NHA$, $SO_2NA_2$, $(CH_2)_nAr$, $(CH_2)_nHet$, CH(OH)Ar, $(CH_2)_nNHCO(CH_2)_nAr$, COAr, $(CH_2)_nCONH(CH_2)_nAr$, $(CH_2)_nCONH(CH_2)_nHet$, $(CH_2)_nCOOH$, $(CH_2)_nCOOA$, $(CH_2)_nCONH_2$, $(CH_2)_nCONHA$, $(CH_2)_nCONA_2$, $SO_2Het$, $(CH_2)_nNH_2$, $(CH_2)_nNHA$, $(CH_2)_nNA_2$, $(CH_2)_nOAr$ or $CONH(CH_2)_2OA$ with the proviso that
a) if one Y denotes N, $R^7$ is absent;
b) if two Y denote N, $R^4$ and $R^7$ are absent;
two adjacent radicals
selected from the group $R^2$, $R^3$, $R^4$, $R^7$
together also denote $OCH_2O$, $OCH_2CH_2O$, NHCONH, $OCF_2O$, CH=N—NH or NH—N=CH;

in Ie A denotes unbranched or branched alkyl having 1-10 C atoms, in which 1-5 H atoms may be replaced by F and/or in which one $CH_2$ group may be replaced by O;

in If Ar denotes phenyl which is unsubstituted or mono-, di- or trisubstituted by Hal and/or $NR^5COA$;

in Ig Het denotes a mono- or bicyclic saturated, unsaturated or aromatic heterocycle having 1 to 4 N, O and/or S atoms, which may be unsubstituted or mono- to trisubstituted by A, $COOR^5$ and/or =O (carbonyl oxygen);

in Ih Het denotes piperidinyl, 4,5-dihydropyridazinyl, pyridyl, morpholinyl, piperazinyl, pyrrolidinyl, tetrahydrofuranyl, 1,3-oxazinanyl, thienyl, pyrazolyl, thiazolyl, benzofuranyl, isoxazolyl, benzothienyl, 3,4-dihydro-2H-pyrido[3,2-b]-1,4-oxazinyl, pyrrolyl, pyrimidinyl, furanyl, imidazolyl, oxazolyl, triazolyl, tetrazolyl, thiadiazole, pyridazinyl, pyrazinyl, indolyl, isoindolyl, benzimidazolyl, indazolyl, quinolyl, 1,3-benzodioxolyl, tetrahydroimidazolyl, tetrahydropyrazolyl, oxazolidinyl or isoxazolidinyl, each of which is unsubstituted or mono- or disubstituted by A, $COOR^5$ and/or =O (carbonyl oxygen);

in Ii Het¹ denotes pyrrolidinyl, tetrahydroimidazolyl, tetrahydropyrazolyl, piperidinyl, morpholinyl, piperazinyl, oxazolidinyl or isoxazolidinyl, each of which is unsubstituted or mono- or disubstituted by A and/or =O;

in Ij R¹ denotes a mono- or bicyclic saturated, unsaturated or aromatic heterocycle having 1 to 4 N, O and/or S atoms, which may be unsubstituted or mono- or disubstituted by Hal, A, $OR^5$, CN, $[C(R^5)_2]_nCOOR^5$, $[C(R^5)_2]_nCON(R^5)_2$,

[C(R⁵)₂]ₙCONR⁵[C(R⁵)₂]ₙAr, [C(R⁵)₂]ₙCONR⁵[C(R⁵)₂]ₙHet, [C(R⁵)₂]ₙCO-Het, [C(R⁵)₂]ₙN(R⁵)₂, [C(R⁵)₂]ₙAr, [C(R⁵)₂]ₙHet, [C(R⁵)₂]ₙOR⁵ and/or [C(R⁵)₂]ₙCONR⁵[C(R⁵)₂]ₙN(R⁵)₂, Y, independently of one another, denotes N or C, where a maximum of two Y may denote N, R², R³, R⁴, R⁷ each, independently of one another, denote H, Hal, A, OA, SO₂N(R⁵)₂, S(O)ₘHet, CO—Ar, [C(R⁵)₂]ₙAr, [C(R⁵)₂]ₙHet, C(R⁵)(OR⁵)Ar, [C(R⁵)₂]ₙOR⁵, [C(R⁵)₂]ₙOAr, [C(R⁵)₂]ₙN(R⁵)₂, [C(R⁵)₂]ₙCON(R⁵)₂, [C(R⁵)₂]ₙCOOR⁵, [C(R⁵)₂]ₙCONR⁵[C(R⁵)₂]ₙAr, [C(R⁵)₂]ₙCONR⁵[C(R⁵)₂]ₙHet or [C(R⁵)₂]ₙNR⁵CO[C(R⁵)₂]ₙAr with the proviso that
a) if one Y denotes N, R⁷ is absent;
b) if two Y denote N, R⁴ and R⁷ are absent;
two adjacent radicals selected from the group R², R³, R⁴, R⁷ together also denote OCH₂O, OCH₂CH₂O, NHCONH, OCF₂O, CH=N—NH or NH—N=CH, R⁵ denotes A or H, A denotes unbranched or branched alkyl having 1-10 C atoms, in which 1-5 H atoms may be replaced by F and/or in which one CH₂ group may be replaced by O, Ar denotes phenyl which is unsubstituted or mono-, di- or trisubstituted by Hal and/or NR⁵COA, Het denotes a mono- or bicyclic saturated, unsaturated or aromatic heterocycle having 1 to 4 N, O and/or S atoms, which may be unsubstituted or mono- to trisubstituted by A, COOR⁵ and/or =O (carbonyl oxygen), Hal denotes F, Cl, Br or I, m denotes 0, 1 or 2, n denotes 0, 1, 2, 3 or 4;

and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds of the formula I can preferably be obtained by reacting a compounds of the formula II with a compound of the formula III.

The starting compounds of the formulae II and III are generally known. If they are novel, however, they can be prepared by methods known per se.

The reaction is carried out in an inert solvent and is generally carried out in the presence of NaHSO₃/Na₂S₂O₅.

Depending on the conditions used, the reaction time is between a few minutes and 14 days, the reaction temperature is between about −15° and 150°, normally between 10° and 100°, particularly preferably between 15° and 80° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to DMF.

Compounds of the formula I can furthermore preferably be obtained by reacting a compound of the formula IV with a compound of the formula V. The reaction is carried out under conditions as are known to the person skilled in the art for a Suzuki reaction.

The starting compounds of the formulae IV and V are generally known. If they are novel, however, they can be prepared by methods known per se.

In the compounds of the formula V, L preferably denotes

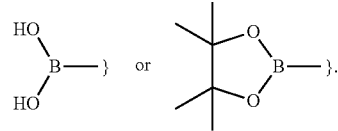

The reaction is carried out under standard conditions of a Suzuki coupling. Depending on the conditions used, the reaction time is between a few minutes and 14 days, the reaction temperature is between about −30° and 140°, normally between 0° and 150°, in particular between about 60° and about 130° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to DMF.

Furthermore, free amino groups can be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide;

alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable salts, tautomers and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable salts and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable salts and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable salts and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment and control of cancer diseases.

The present invention encompasses the use of the compounds of the formula I and/or physiologically acceptable salts, tautomers and stereoisomers thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma bowel cancer. A further group of preferred forms of cancer are monocytic leukaemia, lung adenocarcinoma, small-cell lung carcinomas, pancreatic cancer, glioblastomas and breast carcinoma.

Also encompassed is the use of the compounds of the formula I and/or physiologically acceptable salts, tautomers and stereoisomers thereof for the preparation of a medicament for the treatment and/or control of a tumour-induced disease in a mammal, in which to this method a therapeutically effective amount of a compound according to the invention is administered to a sick mammal in need of such treatment. The therapeutic amount varies according to the particular disease and can be determined by the person skilled in the art without undue effort.

Particular preference is given to the use for the treatment of a disease, where the disease is a solid tumour.

The solid tumour is preferably selected from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention furthermore relates to the use of the compounds according to the invention for the treatment of bone pathologies, where the bone pathology originates from the group osteosarcoma, osteoarthritis and rickets.

The compounds of the formula I may also be administered at the same time as other well-known therapeutic agents that are selected for their particular usefulness against the condition that is being treated.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors.

The present compounds are particularly suitable for administration at the same time as radiotherapy.

"Oestrogen receptor modulators" refers to compounds which interfere with or inhibit the binding of oestrogen to the receptor, regardless of mechanism.

Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cisaminedichloro(2-methylpyridine)platinum, benzylguanine, glufosfamide, GPX100, (trans,trans,trans)bis-mu-(hexane-1,6-diamine)-mu-[diamineplatinum(I)]bis[diamine(chloro)platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxo-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-Lvalyl-L-valyl-N-methyl-L-valyl-L-prolyl-L-proline-t-butylamide, TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)-dione, lurtotecan, 7-[2-(N-isopropylamino)ethyl]-(20S)camptothecin, BNP1350, BNP11100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexahydrofuro(3',4':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASKRAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Evidence of the Action of Pharmacological Inhibitors on the Proliferation/Vitality of Tumour Cells In Vitro 1.0 Background In the present experiment description, the inhibition of tumour cell proliferation/tumour cell vitality by active ingredients is described.

The cells are sown in a suitable cell density in microtitre plates (96-well format) and the test substances are added in the form of a concentration series. After four further days of cultivation in serum-containing medium, the tumour cell proliferation/tumour cell vitality can be determined by means of an Alamar Blue test system.

2.0 Experimental Procedure 2.1 Cell Culture

For example commercially available colon carcinoma cell lines, ovary cell lines, prostate cell lines or breast cell lines, etc.

The cells are cultivated in medium. At intervals of several days, the cells are detached from the culture dishes with the aid of trypsin solution and sown in suitable dilution in fresh medium. The cells are cultivated at 37° Celsius and 10% $CO_2$.

2.2. Sowing of the Cells

A defined number of cells (for example 2000 cells) per culture/well in a volume of 180 µl of culture medium are sown in microtitre plates (96 well cell-culture plates) using a multichannel pipette. The cells are subsequently cultivated in a CO2 incubator (37° C. and 10% CO2).

2.3. Addition of the Test Substances

The test substances are dissolved, for example, in DMSO and subsequently employed in corresponding concentration (if desired in a dilution series) in the cell culture medium. The dilution steps can be adapted depending on the efficiency of the active ingredients and the desired spread of the concentrations. Cell culture medium is added to the test substances in corresponding concentrations. The addition of the test substances to the cells can take place on the same day as the sowing of the cells. To this end, in each case 20 µl of substance solution from the predilution plate are added to the cultures/wells. The cells are cultivated for a further 4 days at 37° Celsius and 10% $CO_2$.

2.4. Measurement of the Colour Reaction

In each case, 20 µl of Alamar Blue reagent are added per well, and the microtitre plates are incubated, for example, for a further seven hours in a CO2 incubator (at 37° C. and 10% CO2). The plates are measured in a reader with a fluorescence filter at a wavelength of 540 nm. The plates can be shaken gently immediately before the measurement.

3. Evaluation

The absorbance value of the medium control (no cells and test substances used) is subtracted from all other absorbance values. The controls (cells without test substance) are set equal to 100 percent, and all other absorbance values are set in relation thereto (for example in % of control):

Calculation:

100*(value with cells and test substance−value of medium control)/(value with cells−value of medium control)

$IC_{50}$ values (50% inhibition) are determined with the aid of statistics programs, such as, for example, RS1. $IC_{50}$ data of compounds according to the invention are indicated in Table 1.

4.0 Test for the Inhibition of PDK1

The experimental batches are carried out in a flashplate system with 384 wells/microtitration plate.

In each case, the PDK1 sample $His_6$-PDK1(1-50)(3.4 nM), the PDK1 substrate biotin-bA-bA-KTFCGTPEYLAPEVR-REPRILSEEEQEMFRDFDYIADWC (400 nM), 4 µM ATP (with 0.2 µCi of $^{33}$P-ATP/well) and the test substance in 50 µl of conventional experimental solution per well are incubated at 30° C. for 60 min. The test substances are employed in corresponding concentrations (if desired in a dilution series). The control is carried out without test substance. The reaction is stopped using standard methods and washed. The activity of the kinase is measured via the incorporated radioactivity in top count. In order to determine the non-specific kinase reaction (blank value), the experimental batches are carried out in the presence of 100 nM staurosporin.

5.0 Evaluation

The radioactivity (decompositions per minute) of the blank value (no use of test substance in the presence of staurosporin) is subtracted from all other radioactivity values. The controls (kinase activity without test substance) are set equal to 100 percent and all other radioactivity values (after subtracting the blank value) are expressed set in relation thereto (for example in % of the control).

Calculation:

$$100 * \frac{\text{(value of the kinase activity with test substance} - \text{blank value)}}{\text{(value of the control} - \text{blank value)}} = \% \text{ of the control}$$

$IC_{50}$ values (50% inhibition) are determined with the aid of statistics programmes, such as, for example, RS1. $IC_{50}$ data of compounds according to the invention are indicated in Table 1.

| Material | Order No. | Manufacturer |
| --- | --- | --- |
| Microtitre plates for cell culture (Nunclon Surface 96-well plate) | 167008 | Nunc |
| DMEM | P04-03550 | Pan Biotech |
| PBS (10x) Dulbecco | 14200-067 | Gibco |
| 96-well plates (polypropylene) | 267334 | Nunc |
| AlamarBlue ™ | BUF012B | Serotec |
| FCS | 1302 | Pan Biotech GmbH |
| Trypsin/EDTA solution 10x | L 2153 | Biochrom AG |
| 75 $cm^2$ culture bottles | 353136 | BD Falcon |
| A2780 | 93112519 | ECACC |
| Colo205 | CCL222 | ATCC |
| MCF7 | HTB22 | ATCC |
| PC3 | CRL-1435 | ATCC |
| 384-well flash plates | SMP410A001PK | Perkin Elmer |

1. Test for the Inhibition of Irak4

The experimental batches are carried out in a flashplate system with 384 wells/microtitre plate.

In each case, the IRAK4 sample $His_6$-IRAK4 (7.3 nM), the biotinylated substrate peptide STK substrate 1-biotin (Cisbio Bioassays, France) (300 nM), 10 µM ATP (with 0.25 µCi of $^{33}$P-ATP/well) and the test substance in 50 µl of conventional experimental solution per well are incubated at 22° C. for 180 min. The test substances are employed in corresponding concentrations (if desired in a dilution series). The control is carried out without test substance. The reaction is stopped using standard methods and washed. The activity of the kinase is measured via the incorporated radioactivity in top count. In order to determine the non-specific kinase reaction (blank value), the experimental batches are carried out in the presence of 1 µM staurosporin.

2. Evaluation

The radioactivity (decompositions per minute) of the blank value (no use of test substance in the presence of 1 µM staurosporin) is subtracted from all other radioactivity values. The controls (kinase activity without test substance) are set equal to 100 percent and all other radioactivity values (after subtracting the blank value) are expressed set in relation thereto (for example in % of the control).

Calculation:

$$100 * \frac{\text{(value of the kinase activity with test substance} - \text{blank value)}}{\text{(value of the control} - \text{blank value)}} = \% \text{ of the control}$$

$IC_{50}$ values (50% inhibition) are determined with the aid of statistics programs, such as, for example, RS1.

| Material | Manufacturer | Order number |
|---|---|---|
| Hepes | Merck | 1.10110 |
| MnCl$_2$ | Merck | 1.05934 |
| EDTA, 0.5M | Sigma | E-7889 |
| EGTA | Merck | 1.08435 |
| DMSO | Merck | 1.02952 |
| [33P]-ATP Spec. radioact. 3000 Ci/mmol 1 mCi/0.1 ml | Perkin Elmer | NEG302H |
| Staurosporin | LC Labs | S-9300 |
| BSA, 30% | Sigma | A9205 |
| MgCl$_2$ | Merck | 1.05833 |
| ATP | Calbiochem | 1191 |
| IRAK-4 | Merck | Merck, Lab. Dr.Jaekel |
| STK 1-biotin | Cisbio | 61ST1BLE/C |
| Tween-60 | Merck | 8.22186 |
| NaCl | Merck | 1.06404 |
| FlashPlate 384 HTS | Perkin Elmer | SMP410A Streptavidin coated |

1. Test for the Inhibition of IRAK1

The experimental batches are carried out in a flashplate system with 384 wells/microtitre plate.

In each case, in order to investigate the inhibition of the autophosphorylation activity of IRAK1, the IRAK1 sample His$_6$-IRAK1 (5.1 nM), 1 µM ATP (with 0.25 µCi of $^{33}$P-ATP/well) and the test substance in 50 µl of conventional experimental solution per well are incubated at 22° C. for 180 min. The test substances are employed in corresponding concentrations (if desired in a dilution series). The control is carried out without test substance. The reaction is stopped using standard methods and washed. The activity of the kinase is measured via the incorporated radioactivity in top count. In order to determine the non-specific kinase reaction (blank value), the experimental batches are carried out in the presence of 1 µM staurosporin.

2. Evaluation

The radioactivity (decompositions per minute) of the blank value (no use of test substance in the presence of 1 µM staurosporin) is subtracted from all other radioactivity values. The controls (kinase activity without test substance) are set equal to 100 percent and all other radioactivity values (after subtracting the blank value) are expressed set in relation thereto (for example in % of the control).

Calculation:

$$100 * \frac{\text{(value of the kinase activity with test substance} - \text{blank value)}}{\text{(value of the control} - \text{blank value)}} = \% \text{ of the control}$$

$IC_{50}$ values (50% inhibition) are determined with the aid of statistics programs, such as, for example, RS1.

| Material | Manufacturer | Order number |
|---|---|---|
| Hepes | Merck | 1.10110 |
| EDTA | VWR | E-7889 |
| EDTA | Merck | 1.08418 |
| EGTA | Merck | 1.08435 |
| DMSO | Merck | 1.02952 |
| Staurosporin | LC Labs | S-9300 |
| [33P]-ATP Spec. radioact. 3000 Ci/mmol 1 mCi/0.1 ml | Perkin Elmer | NEG302H |
| BSA, 30% | Sigma | A9205 |
| MgCl$_2$ | Merck | 1.05833 |
| ATP | Calbiochem | 1191 |
| IRAK-1 | Merck | Merck, Lab. Dr.Jaekel Pool B, 232Y08C1.IRK |
| Triton X-100 | Sigma | X-100 |
| NaCl | Merck | 1.06404 |

APCI-MS (atmospheric pressure chemical ionisation-mass spectrometry) (M+H)$^+$.

ESI-MS (electrospray ionisation-mass spectrometry) (M+H)$^+$.

HPLC-APCI-MS & HPLC-ESI-MS conditions
Solvent A: water+0.1% of HCOOH
Solvent B: acetonitrile+0.1% of HCOOH
Solvent C: C
Solvent D: D
Min pressure (bar): 0
Max pressure (bar): 300
Delay volume (ml): 0.00
Equilibration time (min): 0.00
Gradient curve: linear
Gradient program:

| Time (min) | Flow (ml/min) | A (%) | B (%) | C (%) | D (%) |
|---|---|---|---|---|---|
| 0.00 | 0.50 | 98 | 2 | 0 | 0 |
| 5.00 | 0.50 | 2 | 98 | 0 | 0 |
| 8.00 | 0.50 | 2 | 98 | 0 | 0 |
| 8.10 | 0.50 | 98 | 2 | 0 | 0 |
| 13.00 | 0.50 | 98 | 2 | 0 | 0 |

Column: Purosphere RP-18, 55-2, Art. 1.50241.0001, batch: 641047
Pump: Flux Instruments Rheos 2000
Finnigan MAT Spectra System P4000
Detection: Finnigan Surveyor PDA Detector
Finnigan MAT Spectra System UV 6000LP
MS: Finnigan LCQ Deca XP Plus Finnigan LCQ DECA
ESI interface APCI interface
Positive/negative ionisation Positive ionisation
EI-MS (electon impact-mass spectrometry) M$^+$
EI ionisation 70 eV Ion source temperature 220° C., direct evaporation Mass spectrometer: VG Autospec LC-MS (high performance liquid chromatography-mass spectrometry) (M+H)+.

The MS data are obtained as follows: mass spectrum: (M+H)+; Agilent 1100 series system (ion source: electrospray (positive mode); scan: 85-1000 m/e; fragmentation voltage: variable; gas temperature: 300° C., DAD: 220 nm. Flow rate: 2.4 ml/min. The splitter used reduces the flow rate after the DAD to 0.6 ml/min for the MS; column: Chromolith Speed ROD RP-18e 50-4.6; solvent: LiChrosolv Merck KGaA; solvent A: H$_2$O (0.05% of formic acid); solvent B: CH$_3$CN (0.04% of formic acid); gradient: in 2.8 min from 96% of A to 100% of B; followed by 0.5 min 100% of B.

Preparative HPLC Conditions:

Column: Chromolith-prep RP-18e 100-25

Equipment: Shimadzu LC 8A

Eluent A: water+0.1% of TFA

Eluent B: acetonitrile+0.1% of TFA

Gradient: 99:1→1:99 in 15 min.

Flow rate: 30 ml/min

Detection: UV 220 nm $^1$H-NMR: Bruker DPX-300, DRX-500, DRX-400 or AVII-400.

The microwave chemistry is carried out using an "Emrys™ Optimiser single mode microwave reactor" from Personal Chemistry.

General Synthesis Schemes for the Preparation of Compounds According to the Invention Method 1:

Route A

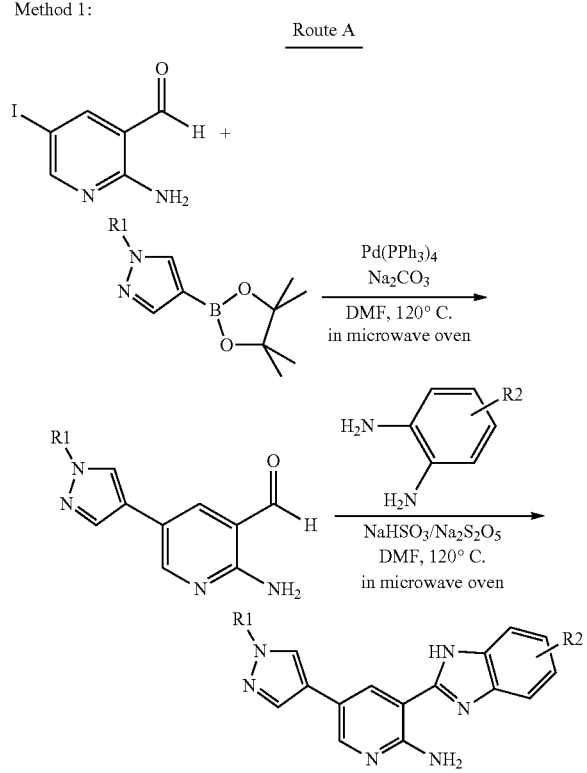

Route B

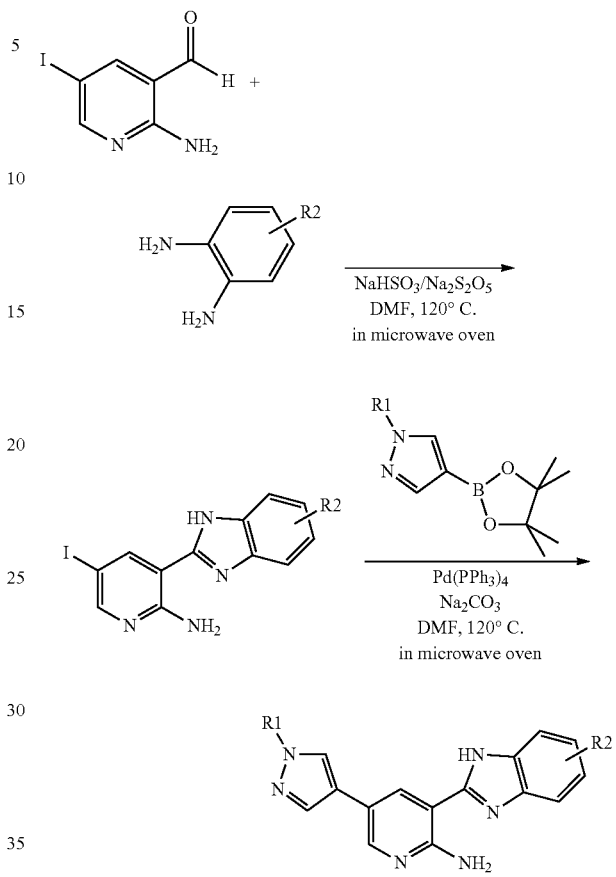

Method 2:

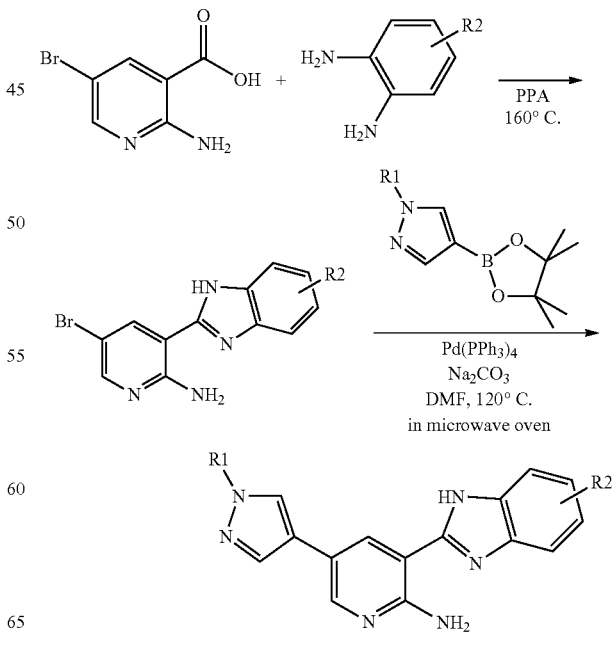

EXAMPLE 1

Preparation of 6-{2-[2-amino-5-(1-methyl-1H-pyrazol-4-yl)pyridin-3-yl]-3H-benzimidazol-5-yl}-5-methyl-4,5-dihydro-2H-pyridazin-3-one ("A1")

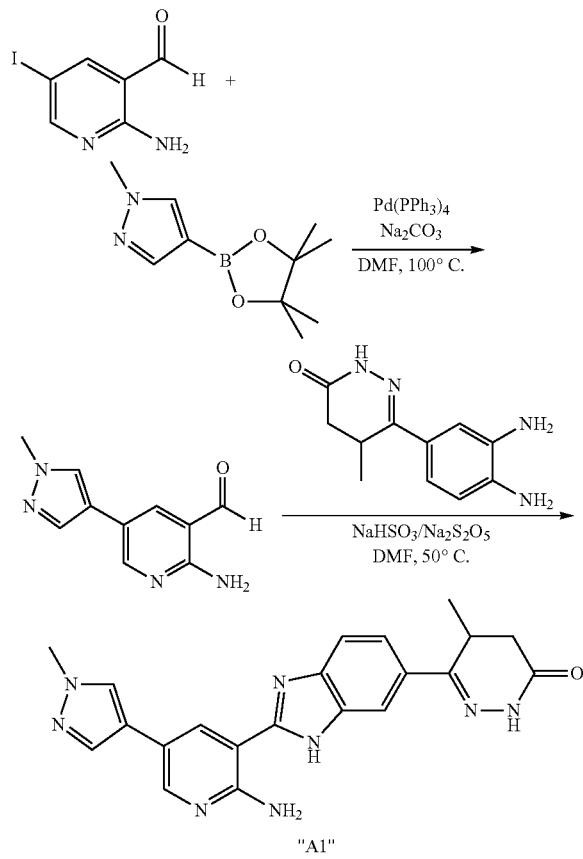

"A1"

1.1 20 ml (40 mmol) of 2 M sodium carbonate solution and 466 mg (0.403 mmol) of tetrakis(triphenylphosphine)palladium(0) are added to a solution, kept under nitrogen, of 2 g (8.064 mmol) of 2-amino-5-iodopyridine-3-carbaldehyde and 3.017 g (14.5 mmol) of 1-methyl-4-(4,4,5,5-tetramethyl-1,3,2-dioxaborolan-2-yl)-1H-pyrazole in 20 ml of N,N-dimethylformamide, the mixture is heated to 100° C. and stirred at this temperature for 1 hour. The reaction mixture is cooled to room temperature, filtered, and the filtrate is partitioned between water and ethyl acetate. The organic phase is dried over sodium sulfate, evaporated, and the residue is triturated with ether and filtered off with suction: 2-amino-5-(1-methyl-1H-pyrazol-4-yl)pyridine-3-carbaldehyde as white solid; ESI 203.

1.2 300 µl (1.485 mmol) of 38-40% sodium hydrogensulfite solution are added to a solution of 100 mg (0.495 mmol) of 2-amino-5-(1-methyl-1H-pyrazol-4-yl)pyridine-3-carbaldehyde and 108 mg (0.495 mmol) of 6-(3,4-diaminophenyl)-5-methyl-4,5-dihydro-2H-pyridazin-3-one in 4 ml of DMF, and the resultant suspension is stirred at 50° C. for 72 hours. The reaction mixture is cooled to RT, water is added, and the precipitated product is filtered off with suction, washed with water and dried, giving 6-{2-[2-amino-5-(1-methyl-1H-pyrazol-4-yl)pyridin-3-yl]-3H-benzimidazol-5-yl}-5-methyl-4,5-dihydro-2H-pyridazin-3-one as yellow solid; APCI-401;

$^1$H NMR (400 MHz, DMSO-d$_6$) δ [ppm] 8.96 (d, J=1.9, 1H), 8.32 (d, J=1.8, 1H), 8.12 (s, 1H), 8.01 (s, 1H), 7.96-7.77 (m, 2H), 7.67 (d, J=8.6, 1 H), 3.84 (d, J=28.4, 3H), 3.53-3.36 (m, 1H), 2.70 (dd, J=15.6, 7.9, 1 H), 2.27 (d, J=16.1, 1 H), 1.13 (d, J=7.3, 3H).

Synthesis of 6-(3,4-diaminophenyl)-5-methyl-4,5-dihydro-2H-pyridazin-3-one is described in Jonas, R.; Klockow, M.; Lues, I.; Prücher, H.; Schliep, H. J.; Wurziger, H. *Eur. J. Med. Chem.* 1993, 28, 129.

The "pyridazinone" building blocks are prepared analogously to the procedure in *Eur. J. Med. Chem.* 1993, 28, 129.

The separation of the racemate (R,S)-6-{2-[2-amino-5-(1-methyl-1H-pyrazol-4-yl)pyridin-3-yl]-3H-benzimidazol-5-yl}-5-methyl-4,5-dihydro-2H-pyridazin-3-one into the two enantiomers (R)-6-{2-[2-amino-5-(1-methyl-1H-pyrazol-4-yl)pyridin-3-yl]-3H-benzimidazol-5-yl}-5-methyl-4,5-dihydro-2H-pyridazin-3-one ("A2") and (S)-6-{2-[2-amino-5-(1-methyl-1H-pyrazol-4-yl)pyridin-3-yl]-3H-benzimidazol-5-yl}-5-methyl-4,5-dihydro-2H-pyridazin-3-one ("A3")

is carried out by means of preparative chiral HPLC and a polarimeter as detector.

Preparative HPLC: at Room Temperature
Instrument: VWR LaPrep
Mobile phase. MeOH/EtOH 1/1
Flow rate. 100 ml/min
Column: ChiralPAK® AD 2×(25×5 cm)
Wavelength 270 nM
Racemate: 100 mg of racemate/injection (injection solvent. EtOH/MeOH/DEA 5:3:2)
Enantiomer 1 ("A2"): $t_R$=23.4 min (−) MeOH/EtOH 1:1
Enantiomer 2 ("A3"): $t_R$=33.8 min (+) MeOH/EtOH 1:1
Analytical HPLC: at Room Temperature
Instrument: HPLC LaChrom 7000
Mobile phase. MeOH/EtOH 1/1
Flow rate. 0.8 ml/min
Column: ChiralPAK® AD-H (25×0.46 cm)
Wavelength 270 nM
Enantiomer 1 ("A2"): $t_R$=14.6 min
Enantiomer 2 ("A3"): $t_R$=20.5 min The following compounds are obtained analogously to Example 1

| No. | Name and/or structure | Analysis |
|---|---|---|
| "A4" | 6-{2-[2-Amino-5-(1-methyl-1H-pyrazol-4-yl)-pyridin-3-yl]-1H-benzimidazol-5-yl}-5-ethyl-4,5-dihydro-2H-pyridazin-3-one, trifluoroacetate | APCI-MS [M + H]$^+$ 415.3 |
| | $^1$H NMR (500 MHz, DMSO-d$_6$ + TFA-d$_1$) δ [ppm] 9.07 (d, J = 2.0, 1H), 8.43 (d, J = 2.0, 1H), 8.23 (s, 1H), 8.10 (d, J = 0.9, 1H), 8.00 (s, 1H), 7.91 (dd, J = 8.7, 1.5, 1H), 7.78 (d, J = 8.6, 1H), 3.95 (s, 3H), 3.41 (d, J = 6.8, 1H), 2.73 (dd, J = 16.9, 7.0, 1H), 2.47 (d, J = 16.1, 1H), 1.56 (ddd, J = 22.8, 15.1, 7.2, 2H), 0.94 (t, J = 7.4, 3H) | |
| "A5" | 6-{2-[2-Amino-5-(1-methyl-1H-pyrazol-4-yl)-pyridin-3-yl]-3H-benzimidazol-5-yl}-5,5-dimethyl-4,5-dihydro-2H-pyridazin-3-one | ESI-MS [M + H]$^+$ 415.3 |
| "A6" | 6-{2-[2-Amino-5-(1-methyl-1H-pyrazol-4-yl)-pyridin-3-yl]-3H-benzimidazol-5-yl}-2,5-dimethyl-4,5-dihydro-2H-pyridazin-3-one | EI-MS [M]$^+$ 414.3 |
| | $^1$H NMR (400 MHz, DMSO-d$_6$ + TFA-d$_1$) δ [ppm] 9.06 (d, J = 1.8, 1H), 8.44 (d, J = 1.8, 1H), 8.23 (s, 1H), 8.13 (s, 1H), 8.02-7.98 (m, 1H), 7.93 (d, J = 7.7, 1H), 7.77 (s, 1H), 3.95 (s, 3H), 3.62-3.51 (m, 1H), 3.40 (s, 3H), 2.80 (dd, J = 16.5, 6.6, 1H), 2.40 (d, J = 16.4, 1H), 1.17 (d, J = 7.2, 3H) | |

-continued

| "A7" | 6-{2-[2-Amino-5-(1-methyl-1H-pyrazol-4-yl)-pyridin-3-yl]-3H-benzimidazol-5-yl}-4,5-dihydro-2H-pyridazin-3-one | EI-MS [M]+ 386.2 |
|---|---|---|
| | $^1$H NMR (500 MHz, DMSO-d$_6$ + TFA-d$_1$) δ [ppm] 9.00 (d, J = 2.0, 1H), 8.35 (d, J = 2.0, 1H), 8.14 (s, 1H), 7.99 (s, 1H), 7.94 (s, 1H), 7.81 (dd, J = 8.6, 1.5, 1H), 7.69 (d, J = 8.6, 1H), 3.89 (s, 3H), 3.03 (t, J = 8.2, 2H), 2.46 (d, J = 8.2, 2H) | |
| "A8" | 6-{2-[2-Amino-5-(1-methyl-1H-pyrazol-4-yl)-pyridin-3-yl]-3H-benzimidazol-5-yl}-2H-pyridazin-3-one | ESI-MS [M + H]+ 485.3 |
| | $^1$H NMR (500 MHz, DMSO-d$_6$ + TFA-d$_1$) δ [ppm] 9.01 (s, 1H), 8.39 (s, 1H), 8.18 (d, J = 27.8, 2H), 8.11 (d, J = 9.9, 1H), 7.98 (s, 1H), 7.82 (dd, J = 40.7, 8.5, 2H), 7.03 (d, J = 9.8, 1H), 3.94 (s, 3H) | |

EXAMPLE 2

Preparation of 6-(2-{2-amino-5-[1-(2-morpholin-4-ylethyl)-1H-pyrazol-4-yl]-pyridin-3-yl}-1H-benzimidazol-5-yl)-5-methyl-4,5-dihydro-2H-pyridazin-3-one ("A9") by method 1 and route B is stirred at 50° C. for 14 h. The reaction mixture is cooled to room temperature, and water is added. The yellow precipitate is filtered off, washed with water and diethyl ether and subsequently dried: 2-amino-5-(1-methyl-1H-pyrazol-4-yl)pyridine-3-carbaldehyde as yellow solid; HPLC-MS [M+H]+ 447.

2.2 100 mg (0.224 mmol) of 2-amino-5-(1-methyl-1H-pyrazol-4-yl)pyridine-3-carbaldehyde and 135 mg (0.440 mmol) of 4-{2-[4-(4,4,5,5-tetramethyl-1,3,2-dioxaborolan-2-yl)pyrazol-1-yl]ethyl}morpholine is dissolved in 1.2 ml of N,N-dimethylformamide in a nitrogen-filled microwave vessel, and 0.666 ml (1.32 mmol) of 2M sodium carbonate solution and 23 mg (0.02 mmol) of tetrakis(triphenylphosphine)palladium(0) are added. The reaction solution is irradiated with microwaves for 30 min at 120° C. in Biotage SmithSynthesizer. The reaction mixture is cooled to room temperature, and ethyl acetate/water is added. The aqueous phase again

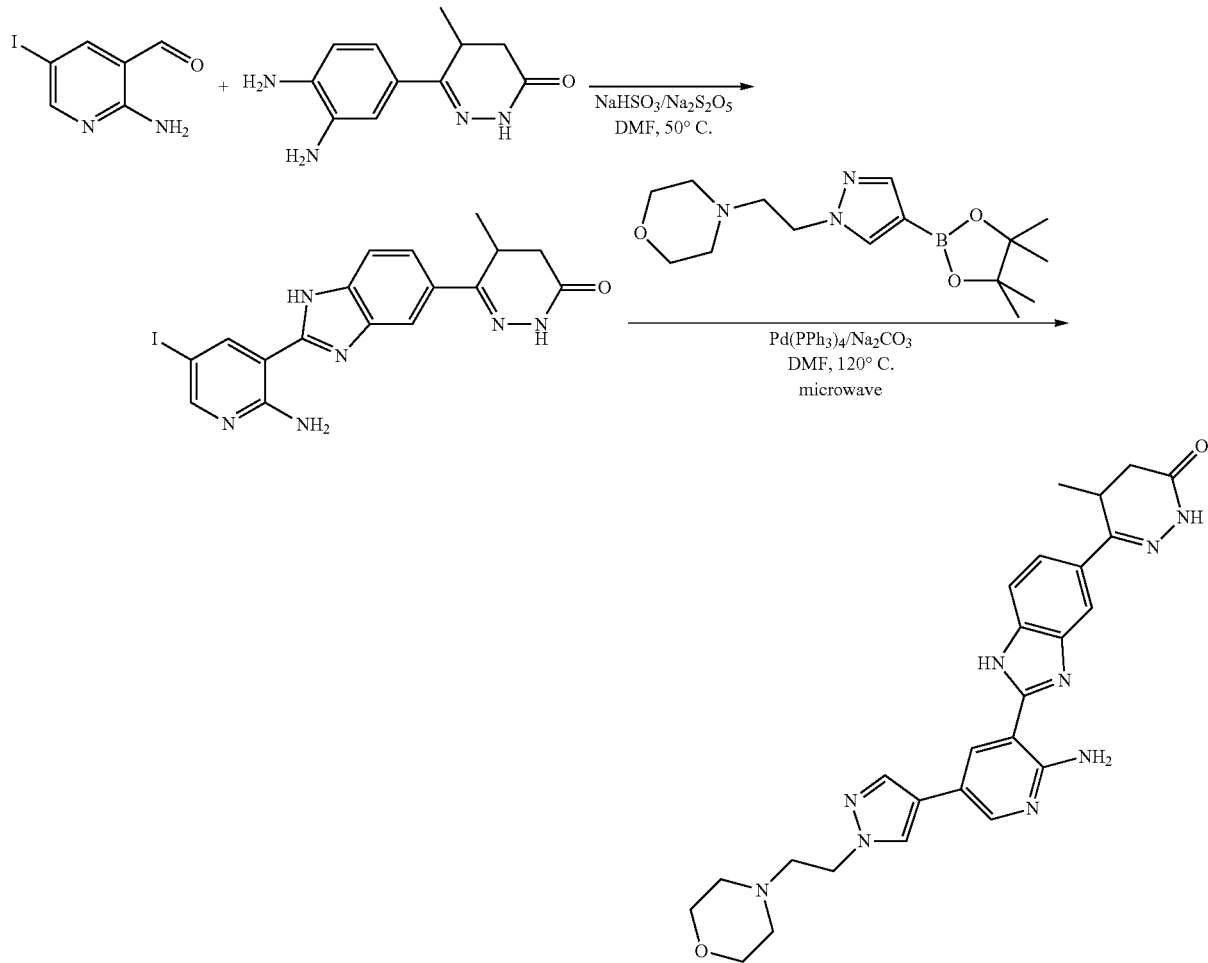

2.1 6.75 ml (33.9 mmol) of sodium hydrogensulfite solution (38-40%) are added to a solution of 2.8 g (11.289 mmol) of 2-amino-5-iodopyridine-3-carbaldehyde and 2.464 g (11.290 mmol) of 6-(3,4-diaminophenyl)-5-methyl-4,5-dihydro-2H-pyridazin-3-one in 30 ml of DMF, and the mixture extracted by shaking with ethyl acetate. The combined organic phases are washed 3× with water, dried using sodium sulfate, and evaporated to dryness. The residue is purified by means of RP-HPLC: 6-(2-{2-amino-5-[1-(2-morpholin-4-yl-ethyl)-1H-pyrazol-4-yl]pyridin-3-yl}-1H-benzimidazol-5-- yl)-5-methyl-4,5-dihydro-2H-pyridazin-3-one trifluoroacetate as yellowish crystals; APCI-MS [M+H]+ 500;
¹H NMR (500 MHz, DMSO-d₆+TFA-d₁) δ [ppm] 9.09 (d, J=2.0, 1H), 8.44 (d, J=2.0, 1H), 8.36 (s, 1H), 8.12 (s, 1H), 8.08 (s, 1H), 7.88 (dd, J=8.7, 1.6, 1H), 7.75 (d, J=8.6, 1H), 4.66 (t, J=6.4, 2H), 3.97 (s, 2H), 3.71 (dd, J=15.0, 8.5, 4H), 3.51 (dd, J=14.6, 7.4, 3H), 3.19 (s, 2H), 2.74 (dd, J=16.8, 6.9, 1H), 2.29 (d, J=15.5, 1H), 1.15 (d, J=7.3, 3H).

The following compounds are prepared analogously to Example 2; unless stated otherwise, the boronic acid and boronic acid ester are commercially available or described in the literature:

| No. | Name and/or structure | Analysis |
|---|---|---|
| "A10" | 6-(2-{2-Amino-5-[1-(3-fluorobenzyl)-1H-pyrazol-4-yl]-pyridin-3-yl}-1H-benzimidazol-5-yl)-5-methyl-4,5-dihydro-2H-pyridazin-3-one trifluoroacetate | APCI-MS [M + H]+ 495 |
| | 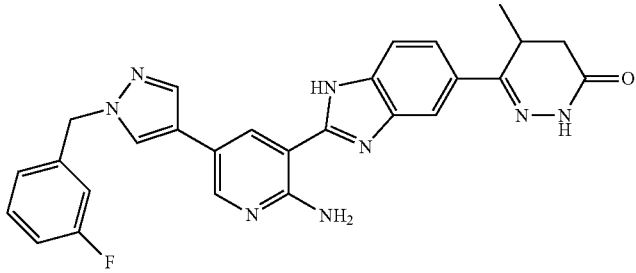 | |
| | ¹H NMR (500 MHz, DMSO-d₆ + TFA-d₁) δ [ppm] 9.08 (d, J = 2.0, 1H), 8.47 (d, J = 2.0, 1H), 8.37 (s, 1H), 8.11 (s, 1H), 8.09 (s, 1H), 7.91 (dd, J = 8.7, 1.5, 1H), 7.78 (d, J = 8.6, 1H), 7.47-7.40 (m, 1H), 7.19-7.08 (m, 3H), 5.49 (s, 2H), 3.60-3.51 (m, 1H), 2.77 (dd, J = 16.7, 6.8, 1H), 2.32 (d, J = 15.6, 1H), 1.18 (d, J = 7.3, 3H) | |
| "A11" | 6-{2-[2-Amino-5-(1-isopropyl-1H-pyrazol-4-yl)pyridin-3-yl]-1H-benzimidazol-5-yl}-5-methyl-4,5-dihydro-2H-pyridazin-3-one, trifluoroacetate | APCI-MS [M + H]+ 429 |
| | ¹H NMR (500 MHz, DMSO-d₆ + TFA-d₁) δ [ppm] 9.05 (d, J = 2.0, 1H), 8.42 (d, J = 2.0, 1H), 8.30 (s, 1H), 8.08 (d, J = 1.1, 1H), 7.99 (s, 1H), 7.88 (dd, J = 8.6, 1.6, 1H), 7.76 (d, J = 8.6, 1H), 4.56 (hept, J = 6.7, 1H), 3.59-3.45 (m, 1H), 2.75 (dd, J = 16.7, 6.9, 1H), 2.29 (d, J = 15.5, 1H), 1.48 (d, J = 6.7, 6H), 1.15 (d, J = 7.3, 3H) | |
| "A12" | 6-(2-{2-Amino-5-[1-(2-methoxyethyl)-1H-pyrazol-4-yl]-pyridin-3-yl}-1H-benzimidazol-5-yl)-5-methyl-4,5-dihydro-2H-pyridazin-3-one, trifluoroacetate | APCI-MS [M + H]+ 445 |
| | 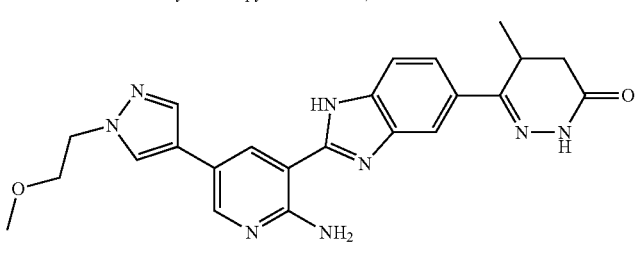 | |
| | ¹H NMR (500 MHz, DMSO-d₆ + TFA-d₁) δ [ppm] 9.07 (d, J = 2.0, 1H), 8.46 (d, J = 2.0, 1H), 8.25 (s, 1H), 8.10 (s, 1H), 8.04 (s, 1H), 7.90 (dd, J = 8.7, 1.6, 1H), 7.78 (d, J = 8.6, 1H), 4.36 (t, J = 5.1, 2H), 3.76 (t, J = 5.2, 2H), 3.63-3.49 (m, 1H), 3.28 (s, 3H), 2.77 (dd, J = 16.7, 6.8, 1H), 2.31 (d, J = 15.6, 1H), 1.17 (d, J = 7.3, 3H) | |
| "A13" | 6-(2-{2-Amino-5-[1-(3-methoxypropyl)-1H-pyrazol-4-yl]-pyridin-3-yl}-1H-benzimidazol-5-yl)-5-methyl-4,5-dihydro-2H-pyridazin-3-one, trifluoroacetate | APCI-MS [M + H]+ 459 |
| | ¹H NMR (400 MHz, DMSO-d₆ + TFA-d₁) δ [ppm] 9.08 (d, J = 2.0, 1H), 8.46 (d, J = 2.1, 1H), 8.27 (s, 1H), 8.11 (s, 1H), 8.04 (s, 1H), 7.92 (dd, J = 8.7, 1.6, 1H), 7.79 (d, J = 8.7, 1H), 4.26 (t, J = 7.0, 2H), 3.62-3.51 (m, 1H), 3.36 (t, J = 6.0, 2H), 3.28 (s, 3H), 2.78 (dd, J = 16.7, 6.8, 1H), 2.33 (d, J = 15.6, 1H), 2.10 (p, J = 6.5, 2H), 1.19 (d, J = 7.3, 3H) | |

| No. | Name and/or structure | Analysis |
|---|---|---|
| "A14" | 6-(2-{2-Amino-5-[1-(2-pyrrolidin-1-ylethyl)-1H-pyrazol-4-yl]pyridin-3-yl}-1H-benzimidazol-5-yl)-5-methyl-4,5-dihydro-2H-pyridazin-3-one, trifluoroacetate | APCI-MS [M + H]⁺ 484 |

<sup>1</sup>H NMR (400 MHz, DMSO-d$_6$ + TFA-d$_1$) δ [ppm] 9.08 (d, J = 2.0, 1H), 8.44 (d, J = 2.0, 1H), 8.35 (s, 1H), 8.12 (s, 1H), 8.08 (s, 1H), 7.88 (dd, J = 8.7, 1.6, 1H), 7.75 (d, J = 8.7, 1H), 4.59 (t, J = 6.1, 2H), 3.73 (t, J = 6.1, 2H), 3.61-3.47 (m, 3H), 3.11-2.99 (m, 2H), 2.74 (dd, J = 16.8, 6.8, 1H), 2.29 (d, J = 15.7, 1H), 2.08-1.93 (m, 2H), 1.93-1.79 (m, 2H), 1.15 (d, J = 7.3, 3H)

| No. | Name and/or structure | Analysis |
|---|---|---|
| "A15" | 6-(2-{2-Amino-5-[1-(2-dimethylaminoethyl)-1H-pyrazol-4-yl]pyridin-3-yl}-1H-benzimidazol-5-yl)-5-methyl-4,5-dihydro-2H-pyridazin-3-one, trifluoroacetate | APCI-MS [M + H]⁺ 458 |

$^1$H NMR (400 MHz, DMSO-d$_6$ +TFA-d) δ [ppm] 9.12 (d, J = 2.0, 1H), 8.49 (d, J = 2.0, 1H), 8.40 (s, 1H), 8.16 (s, 1H), 8.12 (s, 1H), 7.92 (dd, J = 8.7, 1.5, 1H), 7.80 (d, J = 8.6, 1H), 4.66 (t, J = 6.2, 2H), 3.69 (t, J = 6.2, 2H), 3.61-3.51 (m, 1H), 2.90 (s, 6H), 2.78 (dd, J = 16.7, 6.8, 1H), 2.33 (d, J = 15.7, 1H), 1.19 (d, J = 7.3, 3H)

| No. | Name and/or structure | Analysis |
|---|---|---|
| "A16" | 6-(2-{2-Amino-5-[1-(1-methylpiperidin-4-yl)-1H-pyrazol-4-yl]pyridin-3-yl}-1H-benzimidazol-5-yl)-5-methyl-4,5-dihydro-2H-pyridazin-3-one, trifluoroacetate | APCI-MS [M + H]⁺ 484 |

$^1$H NMR (500 MHz, DMSO-d$_6$ + TFA-d$_1$) δ [ppm] 9.10 (d, J = 2.0, 1H), 8.48 (d, J = 2.0, 1H), 8.37 (s, 1H), 8.12 (s, 1H), 8.10 (s, 1H), 7.92 (dd, J = 8.7, 1.5, 1H), 7.79 (d, J = 8.6, 1H), 4.57 (tt, J = 11.7, 3.9, 1H), 3.65 (d, J = 12.6, 2H), 3.59-3.52 (m, 1H), 3.26 (t, J = 11.9, 2H), 2.89 (s, 3H), 2.78 (dd, J = 16.8, 6.9, 1H), 2.39-2.18 (m, 5H), 1.19 (d, J = 7.3, 3H)

| No. | Name and/or structure | Analysis |
|---|---|---|
| "A17" | After the Suzuki coupling of the Boc-protected piperidine-pyrazoleboronic acid ester, the Boc protecting group is cleaved off under standard conditions in dioxane/HCl, giving 6-{2-[2-amino-5-(1-piperidin-4-yl-1H-pyrazol-4-yl)-pyridin-3-yl]-1H-benzimidazol-5-yl}-5-methyl-4,5-dihydro-2H-pyridazin-3-one, trifluoroacetate | APCI-MS [M + H]⁺ 470 |

$^1$H NMR (500 MHz, DMSO-d$_6$ + TFA-d$_1$) δ [ppm] 9.11 (d, J = 2.0, 1H), 8.48 (d, J = 2.0, 1H), 8.37 (s, 1H), 8.12 (s, 1H), 8.10 (s, 1H), 7.92 (dd, J = 8.7, 1.5, 1H), 7.79 (d, J = 8.6, 1H), 4.66-4.57 (m, 1H), 3.60-3.52 (m, 1H), 3.52-3.45 (m, 2H), 3.19 (td, J = 12.7, 3.0, 2H), 2.78 (dd, J = 16.7, 6.8, 1H), 2.38-2.27 (m, 3H), 2.27-2.17 (m, 2H), 1.19 (d, J = 7.3, 3H)

| No. | Name and/or structure | Analysis |
|---|---|---|
| "A18" | 6-(2-{2-Amino-5-[1-(tetrahydrofuran-2-ylmethyl)-1H-pyrazol-4-yl]pyridin-3-yl}-1H-benzimidazol-5-yl)-5-methyl-4,5-dihydro-2H-pyridazin-3-one, trifluoroacetate | APCI-MS [M + H]⁺ 471 |
| "A19" | Cleaving off of the protecting group from the BOC-protected compound gives 6-[2-(6-amino-6'-piperazin-1-yl-[3,3']bipyridinyl-5-yl)-1H-benzimidazol-5-yl]-5-methyl-4,5-dihydro-2H-pyridazin-3-one, trifluoroacetate | ESI-MS [M + H]⁺ 482.3 |

$^1$H NMR (500 MHz, DMSO-d$_6$ + TFA-d$_1$) δ [ppm] 9.12 (d, J = 2.1, 1H), 8.57 (t, J = 2.1, 2H), 8.30 (dd, J = 9.3, 2.4, 1H), 8.08 (s, 1H), 7.88 (dd, J = 8.7, 1.5, 1H), 7.75 (d, J = 8.7, 1H), 7.40 (d, J = 9.3, 1H), 3.95-3.87 (m, 4H), 3.52 (p, J = 7.7, 1H), 3.34-3.27 (m, 4H), 2.73 (dd, J = 16.8, 6.8, 1H), 2.29 (d, J = 15.8, 1H), 1.15 (d, J = 7.3, 3H)

| No. | Name and/or structure | Analysis |
|---|---|---|
| "A20" | 6-{2-[2-Amino-5-(2-dimethylaminothiazol-4-yl)pyridin-3-yl]-1H-benzimidazol-5-yl}-5-methyl-4,5-dihydro-2H-pyridazin-3-one | HPLC-MS [M + H]⁺ 447.2 |
| "A21" | 6-[2-(6-Amino-6'-methoxy-[3,3']bipyridinyl-5-yl)-1H-benzimidazol-5-yl]-5-methyl-4,5-dihydro-2H-pyridazin-3-one, trifluoroacetate | ESI-MS [M + H]⁺ 428.3 |

| No. | Name and/or structure | Analysis |
|---|---|---|
| | $^1$H NMR (500 MHz, DMSO-d$_6$ + TFA-d$_1$) δ [ppm] 9.14 (d, J = 2.1, 1H), 8.64 (d, J = 2.5, 1H), 8.53 (d, J = 2.1, 1H), 8.15 (dd, J = 8.7, 2.6, 1H), 8.07 (d, J = 1.0, 1H), 7.88 (dd, J = 8.7, 1.6, 1H), 7.74 (d, J = 8.6, 1H), 7.03 (d, J = 8.6, 1H), 3.93 (s, 3H), 3.52 (p, J = 7.1, 1H), 2.73 (dd, J = 16.8, 6.9, 1H), 2.29 (d, J = 15.6, 1H), 1.15 (d, J = 7.3, 3H) | |
| "A22" | 6-[2-(6,6'-Diamino-[3,3']bipyridinyl-5-yl)-1H-benzimidazol-5-yl]-5-methyl-4,5-dihydro-2H-pyridazin-3-one, trifluoroacetate 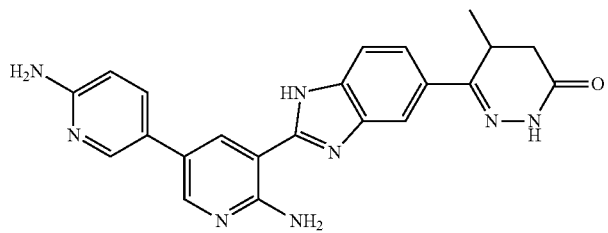 | ESI-MS [M + H]$^+$ 413.3 |
| | $^1$H NMR (500 MHz, DMSO-d$_6$ + TFA-d$_1$) δ [ppm] 9.14 (d, J = 2.1, 1H), 8.59 (d, J = 2.1, 1H), 8.44 (d, J = 2.2, 1H), 8.40 (dd, J = 9.3, 2.3, 1H), 8.13 (s, 1H), 7.94 (dd, J = 8.7, 1.5, 1H), 7.80 (d, J = 8.7, 1H), 7.24 (d, J = 9.3, 1H), 3.61-3.51 (m, 1H), 2.79 (dd, J = 16.8, 6.9, 1H), 2.35 (d, J = 15.6, 1H), 1.21 (d, J = 7.3, 3H) | |

EXAMPLE 2A

Preparation of 6-{2-[2-amino-5-(4-fluoro-2H-pyrazol-3-yl)pyridin-3-yl]-1H-benzimidazol-5-yl}-5-methyl-4,5-dihydro-2H-pyridazin-3-one ("A23")

Alternatively to the standard conditions of Suzuki coupling in method 1 route A, the synthesis sequence can also be carried out under conditions of a Stille coupling.

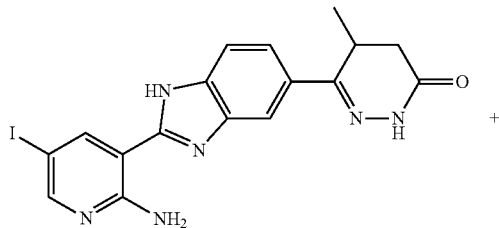

+

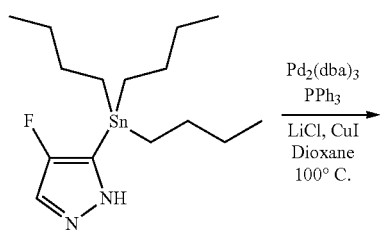

$\xrightarrow{\substack{Pd_2(dba)_3 \\ PPh_3 \\ LiCl, CuI \\ Dioxane \\ 100° C.}}$

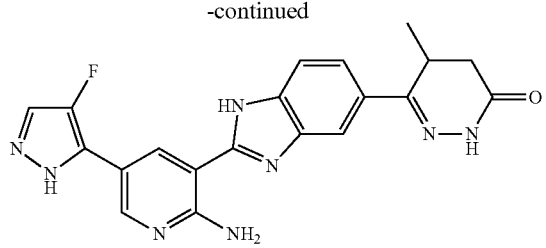

100 mg (0.224 mmol) of 6-[2-(2-amino-5-iodopyridin-3-yl)-1H-benzimidazol-5-yl]-5-methyl-4,5-dihydro-2H-pyridazin-3-one, 252.2 mg (0.672 mmol) of 4-fluoro-5-tributylstannanyl-1H-pyrazole, 41.5 mg (0.045 mmol) of tris(dibenzylideneacetone)dipalladium(0), 23.5 mg (0.090 mmol) of triphenylphosphine, 28.5 mg (0.672 mmol) of lithium chloride and 8.5 mg (0.045 mmol) of copper iodide in 2 ml of dioxane are introduced into a nitrogen-filled reaction vessel. The mixture is stirred at 100° C. for 14 h under a nitrogen protective atmosphere. The reaction mixture is cooled to room temperature, and the solvent is removed. DCM and 2N HCl are added to the residue. The precipitate is separated off and washed with DCM/water. The precipitate is purified further via preparative RP-HPLC, giving 6-{2-[2-amino-5-(4-fluoro-2H-pyrazol-3-yl)pyridin-3-yl]-1H-benzimidazol-5-yl}-5-methyl-4,5-dihydro-2H-pyridazin-3-one; HPLC-MS [M+H]$^+$ 405.2;

$^1$H NMR (500 MHz, DMSO-d$_6$+TFA-d$_1$) δ [ppm] 9.14 (d, J=1.9, 1H), 8.42 (d, J=1.9, 1H), 8.06 (d, J=4.4, 2H), 7.88 (dd, J=8.7, 1.6, 1H), 7.74 (d, J=8.6, 1H), 3.54 (p, J=7.6, 1H), 2.75 (dd, J=16.7, 6.8, 1H), 2.30 (d, J=15.6, 1H), 1.15 (d, J=7.3, 3H).

EXAMPLE 3

Preparation of (4-{6-amino-5-[5-(4-methyl-6-oxo-1,4,5,6-tetrahydropyridazin-3-yl)-1H-benzimidazol-2-yl]pyridin-3-yl}pyrazol-1-yl)acetic acid ("A24")

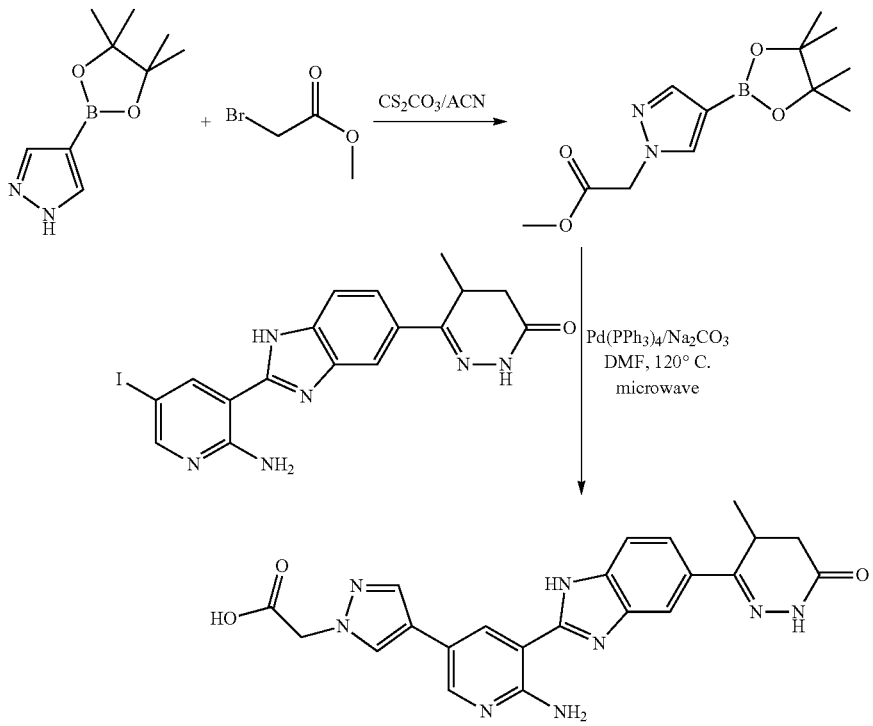

3.1 3.11 g (5.051 mmol) of 4-(4,4,5,5-tetramethyl-1,3,2-dioxaborolan-2-yl)-1H-pyrazole and 1.808 g (5.550 mmol) of caesium carbonate are suspended in 20 ml of ACN. 468 µl (5.050 mmol) of methyl bromoacetate are added, and the mixture is stirred at RT for 72 hours. The precipitate is filtered off with suction and rinsed with ACN. The mother liquor is distilled off to dryness, ethyl acetate is added, and the mixture is washed rapidly 2× with water. The organic phase is immediately dried using sodium sulfate and distilled off to dryness: methyl [4-(4,4,5,5-tetramethyl-1,3,2-dioxaborolan-2-yl)pyrazol-1-yl]acetate as solid; EI-MS [M]⁺ 266.

3.2 100 mg (0.224 mmol) of 2-amino-5-(1-methyl-1H-pyrazol-4-yl)pyridine-3-carbaldehyde and 117 mg (0.440 mmol) of methyl 4-(4,4,5,5-tetramethyl-1,3,2-dioxaborolan-2-yl)pyrazol-1-yl]acetate is dissolved in 1.2 ml of N,N-dimethylformamide in a nitrogen-filled microwave vessel, and 0.666 ml (1.32 mmol) of 2M sodium carbonate solution and 23 mg (0.02 mmol) of tetrakis(triphenylphosphine)palladium (0) are added. The reaction solution is irradiated with microwaves for 30 min at 120° C. in the Biotage SmithSynthesizer. The reaction mixture is cooled to room temperature, and ethyl acetate/water is added. The aqueous phase again extracted by shaking with ethyl acetate. The aqueous phase is acidified using 1N HCl and extracted by shaking 2× with dichloromethane/a little isopropanol. The organic phase is dried using sodium sulfate, and evaporated to dryness. The residue is purified by means of RP-HPLC; since the ester is hydrolysed during the reaction, the following is obtained: (4-{6-amino-5-[5-(4-methyl-6-oxo-1,4,5,6-tetrahydropyridazin-3-yl)-1H-benzimidazol-2-yl]pyridin-3-yl}-pyrazol-1-yl)acetic acid, trifluoroacetate as yellowish crystals; HPLC-MS [M+H]⁺ 445.3;

$^1$H NMR (400 MHz, DMSO-d$_6$+TFA-d$_1$) δ [ppm] 9.10 (d, J=1.9, 1H), 8.49 (d, J=1.9, 1H), 8.29 (s, 1H), 8.11 (s, 1H), 8.07 (s, 1H), 7.92 (dd, J=8.7, 1.3, 1 H), 7.79 (d, J=8.7, 1 H), 5.12 (s, 2H), 3.65-3.50 (m, 1H), 2.78 (dd, J=16.8, 6.9, 1H), 2.33 (d, J=16.2, 1H), 1.19 (d, J=7.3, 3H).

EXAMPLE 4

Preparation of 2-(4-{6-amino-5-[5-(4-methyl-6-oxo-1,4,5,6-tetrahydropyridazin-3-yl)-1H-benzimidazol-2-yl]pyridin-3-yl}pyrazol-1-yl)-N,N-dimethylacetamide ("A25")

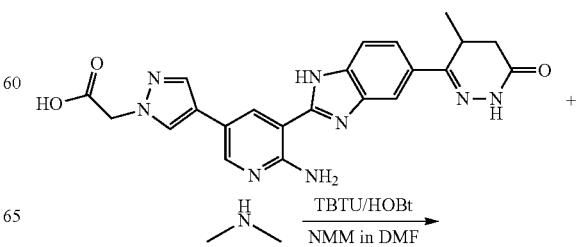

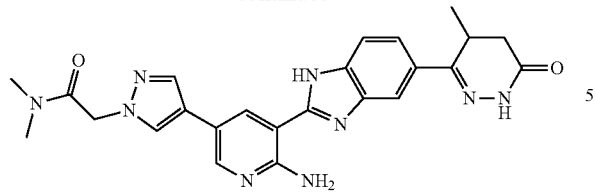

50 mg of "A24" (0.112 mmol) are dissolved in 5 ml of DMF. 35 mg (0.110 mmol) of TBTU, 4.458 mg (0.033 mmol) of HOBt, 83 µl (0.165 mmol) of 2M dimethylamine in THF and 61 µl (0.550 mmol) of N-methylmorpholine are added. The reaction mixture is stirred at room temperature for 14 h, water is added, and the mixture is freeze-dried. The residue is purified by means of RP-HPLC: 2-(4-{6-amino-5-[5-(4-methyl-6-oxo-1,4,5,6-tetrahydropyridazin-3-yl)-1H-benzimidazol-2-yl]pyridin-3-yl}pyrazol-1-yl)-N,N-dimethylacetamide, trifluoroacetate as yellowish crystals; APCI-MS [M+H]⁺ 472;

$^1$H NMR (500 MHz, DMSO-d$_6$+TFA-d$_1$) δ [ppm] 9.09 (d, J=2.0, 1H), 8.47 (d, J=2.1, 1H), 8.21 (s, 1H), 8.11 (s, 1H), 8.03 (s, 1H), 7.91 (dd, J=8.7, 1.5, 1H), 7.78 (d, J=8.7, 1 H), 5.24 (s, 2H), 3.61-3.51 (m, 1H), 3.10 (s, 3H), 2.91 (s, 3H), 2.78 (dd, J=16.7, 6.9, 1H), 2.32 (d, J=15.6, 1H), 1.18 (d, J=7.3, 3H).

6-[2-(2-Amino-5-{1-[2-(4-methylpiperazin-1-yl)-2-oxoethyl]-1H-pyrazol-4-yl}-pyridin-3-yl)-1H-benzimidazol-5-yl]-5-methyl-4,5-dihydro-2H-pyridazin-3-one ("A26"), trifluoroacetate is obtained analogously as yellowish crystals APCI-MS [M+H]⁺ 527;
$^1$H NMR (500 MHz, DMSO-d$_6$+TFA-d$_1$) δ [ppm] 9.11 (d, J=2.0, 1H), 8.49 (d, J=2.0, 1H), 8.22 (s, 1H), 8.11 (s, 1H), 8.06 (s, 1H), 7.91 (dd, J=8.6, 1.6, 1H), 7.79 (d, J=8.6, 1H), 5.36 (q, J=16.1, 2H), 4.35 (dd, J=125.8, 13.9, 2H), 3.61-3.46 (m, 4H), 3.23-3.00 (m, 3H), 2.90 (s, 3H), 2.78 (dd, J=16.8, 6.9, 1H), 2.33 (d, J=15.7, 1H), 1.19 (d, J=7.3, 3H).

EXAMPLE 4A

Preparation of 2-{4-[6-amino-5-(6-methoxy-1H-benzimidazol-2-yl)pyridin-3-yl]pyrazol-1-yl}-N-(3,4-difluorobenzyl)acetamide ("A27")

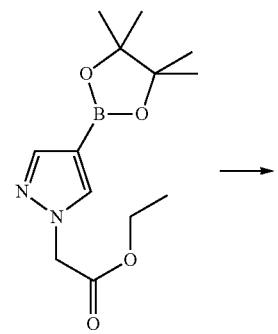

4a.1 {4-[6-Amino-5-(6-methoxy-1H-benzimidazol-2-yl)pyridin-3-yl]-pyrazol-1-yl}acetic acid is prepared by route 1 method B (120° C. in the flask for 14 h, instead of microwaves), the ethyl ester is hydrolysed in the process, and the crude product is reacted further in this way; HPLC-MS [M+H]⁺ 365.2.

4a.2 146 mg of {4-[6-amino-5-(6-methoxy-1H-benzimidazol-2-yl)pyridin-3-yl]pyrazol-1-yl}acetic acid (0.120 mmol) are dissolved in 1.5 ml of DMF. 17.5 mg (0.120 mmol) of 3,4-difluorobenzylamine, 16.2 mg (0.120 mmol) of HOBt, 23 mg (0120 mmol) of EDC and 26.4 µl (0.240 mmol) of N-methylmorpholine are added. The reaction mixture is stirred at room temperature for 14 h, and water/ethyl acetate is subsequently added. The aqueous phase is extracted 2× with ethyl acetate. The combined organic phases are washed with water, dried using sodium sulfate, filtered and evaporated to dryness. The residue is purified by means of preparative RP-HPLC, giving 2-{4-[6-amino-5-(6-methoxy-1H-benzimidazol-2-yl)pyridin-3-yl]pyrazol-1-yl}-N-(3,4-difluorobenzyl)acetamide; HPLC-MS [M+H]⁺ 490.2;

EXAMPLE 5

Preparation of 6-(2-{2-amino-5-[1-(2-oxo-2-piperidin-1-ylethyl)-1H-pyrazol-4-yl]pyridin-3-yl}-3H-benzimidazol-5-yl)-5-methyl-4,5-dihydro-2H-pyridazin-3-one ("A28")

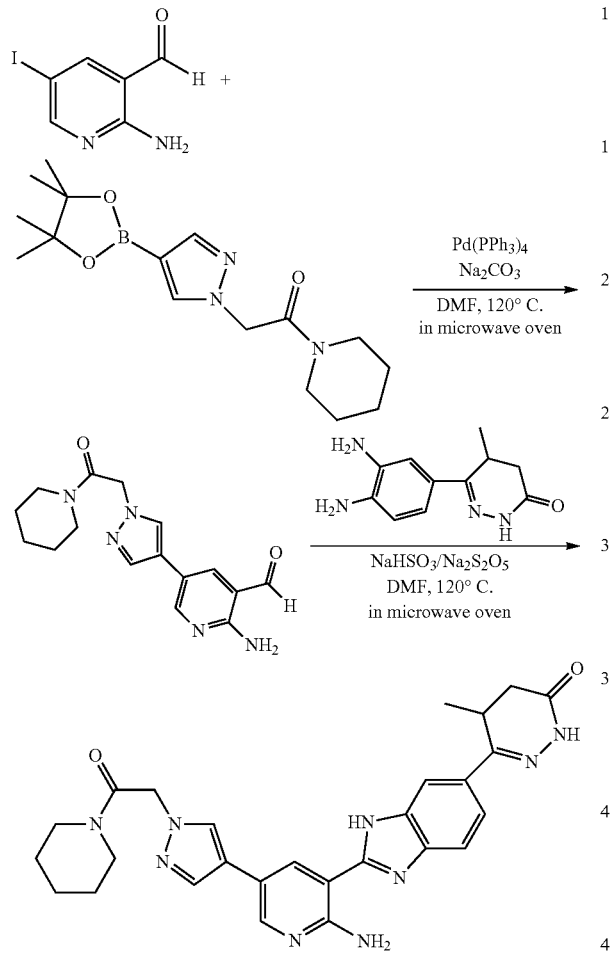

5.1 200 mg (0.806 mmol) of 2-amino-5-iodopyridine-3-carbaldehyde and 501 mg (1.570 mmol) of 1-piperidin-1-yl-2-[4-(4,4,5,5-tetramethyl-1,3,2-dioxaborolan-2-yl)pyrazol-1-yl]ethanone are dissolved in 4 ml of N,N-dimethylformamide in an argon-filled microwave vessel, and 2.5 ml (5 mmol) of 2M sodium carbonate solution and 93.2 mg (0.081 mmol) of tetrakis(triphenylphosphine)palladium (0) are added. The reaction solution is irradiated with microwaves for 30 min at 120° C. in the Biotage SmithSynthesizer. The reaction mixture is cooled to room temperature, water is added, and the mixture is filtered. The filtrate is extracted three times with ethyl acetate, and the combined organic phases are washed 2× with water, dried using sodium sulfate, and evaporated to dryness. The oily residue is purified by means of RP-HPLC, giving 2-amino-5-[1-(2-oxo-2-piperidin-1-ylethyl)-1H-pyrazol-4-yl]pyridine-3-carbaldehyde as yellowish powder; ESI-MS [M+H]+ 314.2.

5.2 110.07 μl (0.558 mmol) of 38-40% sodium hydrogensulfite solution are added to a solution of 70 mg (0.223 mmol) of 2-amino-5-[1-(2-oxo-2-piperidin-1-ylethyl)-1H-pyrazol-4-yl]pyridine-3-carbaldehyde and 58.51 mg (0.268 mmol) of 6-(3,4-diaminophenyl)-5-methyl-4,5-dihydro-2H-pyridazin-3-one in 3 ml DMF, and the mixture is irradiated with microwaves for 30 min at 120° C. in the Biotage SmithSynthesizer. The reaction mixture is cooled to room temperature, and water is added. The precipitate is filtered off and washed with water and subsequently dried. The residue is purified by means of RP-HPLC: 6-(2-{2-amino-5-[1-(2-oxo-2-piperidin-1-ylethyl)-1H-pyrazol-4-yl]pyridin-3-yl}-3H-benzimidazol-5-yl)-5-methyl-4,5-dihydro-2H-pyridazin-3-one as yellow solid; HPLC-MS [M+H]+ 512.2;

$^1$H NMR (400 MHz, DMSO-d$_6$+TFA-d$_1$) δ [ppm] 9.05 (d, J=2.1, 1H), 8.41 (d, J=2.0, 1H), 8.17 (s, 1H), 8.08-8.03 (m, 1H), 7.98 (d, J=0.6, 1 H), 7.87 (dd, J=8.7, 1.6, 1 H), 7.72 (d, J=8.7, 1H), 5.19 (s, 2H), 3.54-3.40 (m, 5H), 2.76-2.69 (m, 1H), 2.28 (d, J=15.7, 1 H), 1.63-1.40 (m, 6H), 1.14 (d, J=7.3, 3H).

An analogous procedure gives 6-(2-{2-amino-5-[1-(2-hydroxyethyl)-1H-pyrazol-4-yl]pyridin-3-yl}-3H-benzimidazol-5-yl)-5-methyl-4,5-dihydro-2H-pyridazin-3-one ("A29")

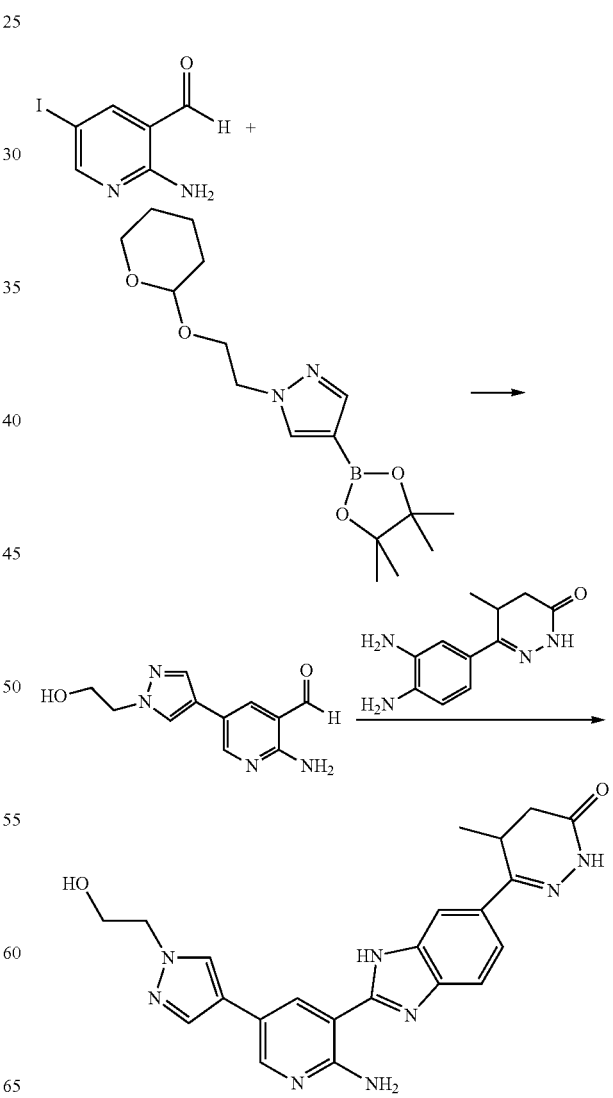

HPLC-MS [M+H]+ 431.2;

¹H NMR (500 MHz, DMSO-d₆+TFA-d₁) δ [ppm] 9.09 (d, J=2.0, 1H), 8.47 (d, J=2.0, 1H), 8.28 (s, 1H), 8.11 (d, J=1.0, 1H), 8.04 (s, 1H), 7.92 (dd, J=8.7, 1.6, 1H), 7.79 (d, J=8.6, 1H), 4.26 (t, J=5.4, 2H), 3.83 (t, J=5.4, 2H), 3.56 (p, J=7.1, 1H), 2.78 (dd, J=16.8, 6.8, 1H), 2.33 (d, J=15.6, 1H), 1.19 (d, J=7.3, 3H).

An analogous procedure gives

2-{4-[6-amino-5-(5-fluoro-6-methoxy-1H-benzimidazol-2-yl)pyridin-3-yl]pyrazol-1-yl}-1-piperidin-1-ylethanone ("A30")

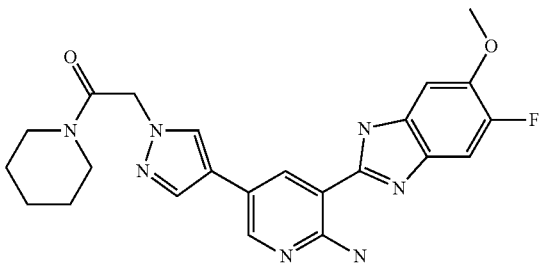 [SMILES: COc1cc2[nH]c(-c3cc(-c4cnn(CC(=O)N5CCCCC5)c4)cnc3N)nc2cc1F]

HPLC-MS [M+H]+ 450.2;

¹H NMR (500 MHz, DMSO-d₆+TFA-d₁) δ [ppm] 9.05 (d, J=2.0, 1H), 8.44 (d, J=2.0, 1H), 8.23 (s, 1H), 8.03 (s, 1H), 7.60 (d, J=10.9, 1H), 7.40 (d, J=7.7, 1 H), 5.25 (s, 2H), 3.97 (s, 3H), 3.51 (s, 4H), 1.69-1.47 (m, 6H).

EXAMPLE 6

Preparation of 3-(1H-benzimidazol-2-yl)-5-(1-piperidin-4-yl-1H-pyrazol-4-yl)pyridin-2-ylamine ("A31") [method 1 route A]

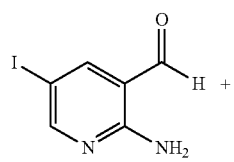

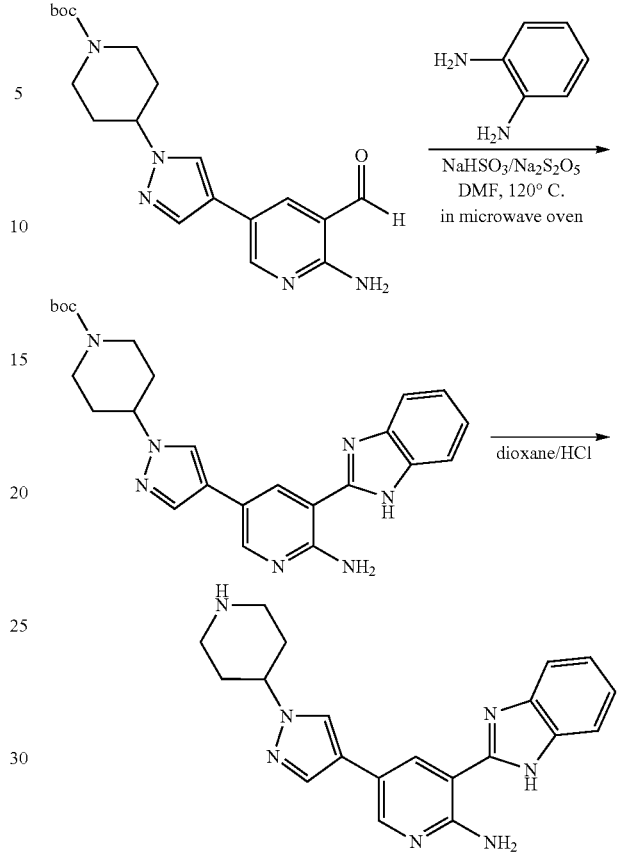

6.1 Suzuki Coupling:

150 mg (0.605 mmol) of 2-amino-5-iodopyridine-3-carbaldehyde and 413 mg (1.089 mmol) of tert-butyl 4-[4-(4,4,5,5-tetramethyl-1,3-dioxolan-2-yl)pyrazol-1-yl]piperidine-1-carboxylate are dissolved in 2.3 ml of N,N-dimethylformamide in a nitrogen-filled microwave vessel, and 1.7 ml (3.4 mmol) of 2M sodium carbonate solution and 35 mg (0.030 mmol) of tetrakis(triphenylphosphine)palladium(0) are added. The reaction solution is irradiated with microwaves for 30 min at 120° C. in the Biotage SmithSynthesizer. The reaction mixture is cooled to room temperature and filtered. The filtrate is evaporated to dryness. The oily residue is purified by means of RP-HPLC, giving tert-butyl 4-[4-(6-amino-5-formylpyridin-3-yl)pyrazol-1-yl]-piperidine-1-carboxylate; HPLC-MS [M+H]+ 372.2.

6.2 Cyclisation to the Benzimidazole:

133.8 μl (0.679 mmol) of 38-40% sodium hydrogensulfite solution are added to a solution of 84.1 mg (0.226 mmol) of tert-butyl 4-[4-(6-amino-5-formylpyridin-3-yl)pyrazol-1-yl]piperidine-1-carboxylate and 29.4 mg (0.272 mmol) of o-phenylenediamine in 4 ml of DMF, and the mixture is irradiated with microwaves for 30 min at 120° C. in the Biotage SmithSynthesizer. The reaction mixture is cooled to room temperature and evaporated to dryness. The residue is purified by means of RP-HPLC: tert-butyl 4-{4-[6-amino-5-(1H-benzimidazol-2-yl)pyridin-3-yl]pyrazol-1-yl}piperidine-1-carboxylate; HPLC-MS [M+H]+ 460.2.

6.3 BOC Removal:

5 ml of 4M HCl in dioxane are added to 41.8 mg (0.091 mmol) of tert-butyl 4-{4-[6-amino-5-(1H-benzimidazol-2-yl)pyridin-3-yl]pyrazol-1-yl}piperidine-1-carboxylate, and the mixture is stirred at room temperature for 14 h. The

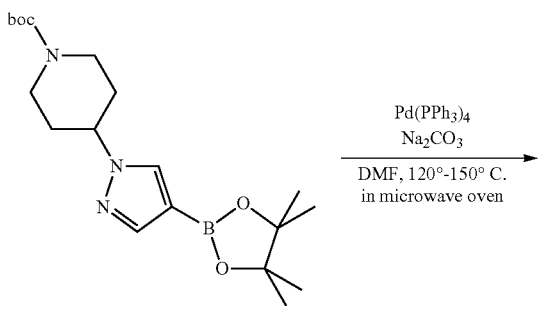

reaction mixture is evaporated to dryness, and water is added. The aqueous phase is adjusted to pH>10 using 2N NaOH and extracted 3× with ethyl acetate. The organic phases are dried using sodium sulfate, filtered and evaporated. The residue is lyophilised, giving 3-(1H-benzimidazol-2-yl)-5-(1-piperidin-4-yl-1H-pyrazol-4-yl)pyridin-2-ylamine as free base; HPLC-MS [M+H]+ 360.2;

$^1$H NMR (500 MHz, DMSO-d$_6$+TFA-d$_1$) δ [ppm] 9.04 (d, J=2.1, 1H), 8.45 (d, J=2.1, 1H), 8.32 (s, 1H), 8.06 (s, 1H), 7.75 (dd, J=6.1, 3.1, 2H), 7.36 (dd, J=6.1, 3.1, 2H), 4.62-4.54 (m, 1H), 3.45 (d, J=13.0, 2H), 3.15 (td, J=12.6, 2.9, 2H), 2.27 (dd, J=13.3, 2.9, 2H), 2.23-2.12 (m, 2H).

In general, the Boc removal is carried out using the standard methods of 4N HCl in dioxane or TFA/DCM, and the substances are isolated as free base or as HCl or TFA salt.

The following compounds are obtained analogously

| No. | Name and/or structure | Analysis |
|---|---|---|
| "A32" | 5-(1H-Benzimidazol-2-yl)-[3,4']bipyridinyl-6-ylamine | HPLC-MS [M + H]+ 288.0 |
| "A33" | 3-(1H-Benzimidazol-2-yl)-5-furan-2-ylpyridin-2-ylamine | HPLC-MS [M + H]+ 277.1 |
| "A34" | 3-(1H-Benzimidazol-2-yl)-5-(1-methyl-1H-pyrazol-4-yl)-pyridin-2-ylamine | HPLC-MS [M + H]+ 291.2 |

$^1$H NMR (400 MHz, DMSO-d$_6$ + TFA-d$_1$) δ [ppm] 9.01 (d, J = 2.1, 1H), 8.39 (d, J = 2.1, 1H), 8.17 (s, 1H), 7.96 (d, J = 0.6, 1H), 7.74 (dd, J = 6.1, 3.1, 2H), 7.35 (dd, J = 6.1, 3.2, 2H), 3.91 (s, 3H).

| No. | Name and/or structure | Analysis |
|---|---|---|
| "A35" | 5-(1H-Benzimidazol-2-yl)-[3,3']bipyridinyl-6,6'-diamine | HPLC-MS [M + H]+ 303.1 |

| No. | Name and/or structure | Analysis |
|---|---|---|
| "A36" | 3-(5-Isopropyl-1H-benzimidazol-2-yl)-5-(1-methyl-1H-pyrazol-4-yl)-pyridin-2-ylamine | HPLC-MS [M + H]$^+$ 333.2 |
| "A37" | 5-(1H-Benzimidazol-2-yl)-[3,3']bipyridinyl-6-ylamine | HPLC-MS [M + H]$^+$ 288.2 |
| "A38" | 3-(1H-Benzimidazol-2-yl)-5-furan-3-ylpyridin-2-ylamine | HPLC-MS [M + H]$^+$ 277.2 |
| "A39" | 3-(1H-Benzimidazol-2-yl)-5-(1H-pyrazol-4-yl)pyridin-2-ylamine  $^1$H NMR (500 MHz, DMSO-d$_6$ + TFA-d$_1$) δ [ppm] 9.05 (d, J = 2.1, 1H), 8.45 (d, J = 2.1, 1H), 8.20 (s, 2H), 7.73 (dd, J = 6.1, 3.1, 2H), 7.36 (dd, J = 6.1, 3.1, 2H) | HPLC-MS [M + H]$^+$ 277.2 |
| "A40" | 3-(1H-Benzimidazol-2-yl)-5-[1-(2-pyrrolidin-1-ylethyl)-1H-pyrazol-4-yl]pyridin-2-ylamine | HPLC-MS [M + H]$^+$ 374.2 |

| No. | Name and/or structure | Analysis |
|---|---|---|
| "A41" | 3-(1H-Benzimidazol-2-yl)-5-pyrimidin-5-ylpyridin-2-yl-amine | HPLC-MS [M + H]+ 289.2 |
| "A42" | 3-(7-Methyl-1H-benzimidazol-2-yl)-5-(1-methyl-1H-pyrazol-4-yl)pyridin-2-amine | HPLC-MS [M + H]+ 305.2 |

1H NMR (500 MHz, DMSO-$d_6$ + TFA-$d_1$) δ [ppm] 9.03 (d, J = 2.1, 1H), 8.41 (d, J = 2.1, 1H), 8.19 (s, 1H), 7.97 (d, J = 0.5, 1H), 7.54 (d, J = 8.1, 1H), 7.27 (t, J = 7.7, 1H), 7.16 (d, J = 7.3, 1H), 3.92 (s, 3H), 2.62 (s, 3H)

| No. | Name and/or structure | Analysis |
|---|---|---|
| "A43" | 3-(6-Methoxy-1H-benzimidazol-2-yl)-5-(1-methyl-1H-pyrazol-4-yl)pyridin-2-ylamine | HPLC-MS [M + H]+ 321.2 |

1H NMR (500 MHz, DMSO-$d_6$ + TFA-$d_1$) δ [ppm] 8.95 (d, J = 2.1, 1H), 8.37 (d, J = 2.1, 1H), 8.17 (s, 1H), 7.95 (d, J = 0.6, 1H), 7.64 (d, J = 8.8, 1H), 7.19 (d, J = 2.3, 1H), 7.00 (dd, J = 8.9, 2.4, 1H), 3.91 (s, 3H), 3.84 (s, 3H)

| No. | Name and/or structure | Analysis |
|---|---|---|
| "A44" | 3-(1H-Benzimidazol-2-yl)-5-(1-propyl-1H-pyrazol-4-yl)-pyridin-2-ylamine | HPLC-MS [M + H]+ 319.2 |

-continued

| No. | Name and/or structure | Analysis |
|---|---|---|
| "A45" | 5-(1-Isobutyl-1H-pyrazol-4-yl)-3-(7-methyl-1H-benzimidazol-2-yl)pyridin-2-ylamine 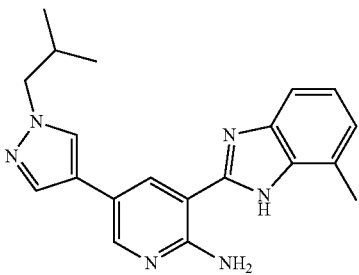 | HPLC-MS [M + H]+ 347.2 |
| "A46" | 3-(7-Methyl-1H-benzimidazol-2-yl)-5-[1-(3-methylbutyl)-1H-pyrazol-4-yl]pyridin-2-ylamine 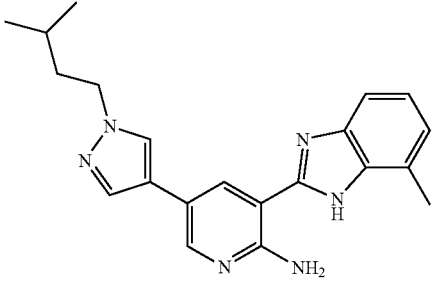 | HPLC-MS [M + H]+ 361.2 |
| "A47" | 5-(7-Methyl-1H-benzimidazol-2-yl)-[3,3']bipyridinyl-6-ylamine 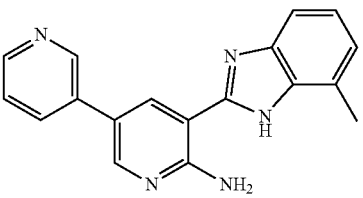 | HPLC-MS [M + H]+ 302.0 |
| "A48" | 3-(7-Methyl-1H-benzimidazol-2-yl)-5-[1-(2-morpholin-4-ylethyl)-1H-pyrazol-4-yl]pyridin-2-ylamine 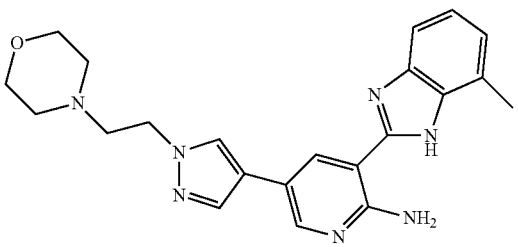 | HPLC-MS [M + H]+ 404.2 |

-continued

| No. | Name and/or structure | Analysis |
|---|---|---|
| "A49" | 3-(5H-[1,3]Dioxolo[4',5':4,5]benzo[1,2-d]imidazol-6-yl)-5-(1-piperidin-4-yl-1H-pyrazol-4-yl)pyridin-2-ylamine | HPLC-MS [M + H]+ 404.2 |
| "A50" | 3-(6-Fluoro-1H-benzimidazol-2-yl)-5-(1-piperidin-4-yl-1H-pyrazol-4-yl)pyridin-2-ylamine<br>hydrochloride | HPLC-MS [M + H]+ 378.2 |
| "A51" | 2-[2-Amino-5-(1-methyl-1H-pyrazol-4-yl)pyridin-3-yl]-3H-benzimidazole-5-carboxylic acid<br><br>$^1$H NMR (400 MHz, DMSO-$d_6$ + TFA-$d_1$) δ [ppm] 9.07 (d, J = 2.1, 1H), 8.42 (d, J = 2.1, 1H), 8.33 (dd, J = 1.5, 0.6, 1H), 8.20 (s, 1H), 8.00-7.95 (m, 2H), 7.78 (dd, J = 8.5, 0.6, 1H), 3.92 (s, 3H) | HPLC-MS [M + H]+ 335.2 |
| "A52" | {2-[2-Amino-5-(1-methyl-1H-pyrazol-4-yl)pyridin-3-yl]-3H-benzimidazol-4-yl}methanol | HPLC-MS [M + H]+ 321.2 |

-continued

| No. | Name and/or structure | Analysis |
|---|---|---|
| "A53" | 3-(6-tert-Butyl-1H-benzimidazol-2-yl)-5-(1-piperidin-4-yl-1H-pyrazol-4-yl)pyridin-2-ylamine | HPLC-MS [M + H]⁺ 416.2 |
| "A54" | 3-(2,2-Difluoro-5H-1,3-dioxolo[4′,5′:4,5]benzo[1,2-d]-imidazol-6-yl)-5-(1-piperidin-4-yl-1H-pyrazol-4-yl)-pyridin-2-ylamine<br><br>hydrochloride | HPLC-MS [M + H]⁺ 440.2 |
| "A55" | 6-[2-Amino-5-(1-piperidin-4-yl-1H-pyrazol-4-yl)pyridin-3-yl]-3,5-dihydro-1H-benzo[1,2-d′;4,5-d″]diimidazol-2-one<br><br>hydrochloride | HPLC-MS [M + H]⁺ 489.2 |
| "A56" | 3-(7-Fluoro-1H-benzimidazol-2-yl)-5-(1-methyl-1H-pyrazol-4-yl)pyridin-2-amine | HPLC-MS [M + H]⁺ 309.2 |

-continued

| No. | Name and/or structure | Analysis |
|---|---|---|
| "A57" | 3-(5,6-Difluoro-1H-benzimidazol-2-yl)-5-(1-piperidin-4-yl-1H-pyrazol-4-yl)pyridin-2-ylamine<br><br>hydrochloride | HPLC-MS [M + H]⁺ 396.2 |
| "A58" | Methyl 2-[2-amino-5-(1-methyl-1H-pyrazol-4-yl)pyridin-3-yl]-3H-benzimidazole-5-carboxylate | HPLC-MS [M + H]⁺ 349.3 |
| "A59" | 5-(1-Piperidin-4-yl-1H-pyrazol-4-yl)-3-(6-trifluoromethyl-1H-benzimidazol-2-yl)pyridin-2-ylamine<br><br>hydrochloride | HPLC-MS [M + H]⁺ 428.2 |
| "A60" | 3-(4-Methoxy-1H-benzoimidazol-2-yl)-5-(1-piperidin-4-yl-1H-pyrazol-4-yl)pyridin-2-ylamine<br><br>hydrochloride | HPLC-MS [M + H]⁺ 390.2 |

¹H NMR (500 MHz, DMSO-d₆ + TFA-d₁) δ [ppm] 9.16 (d, J = 2.0, 1H), 8.47 (d, J = 1.8, 1H), 8.33 (s, 1H), 8.11 (d, J = 0.7, 1H), 7.39-7.29 (m, 2H), 6.95 (d, J = 7.0, 1H), 4.67-4.57 (m, 1H), 4.06 (s, 3H), 3.51 (dt, J = 6.2, 2.8, 2H), 3.20 (td, J = 12.6, 3.5, 2H), 2.36-2.20 (m, 4H)

-continued

| No. | Name and/or structure | Analysis |
|---|---|---|
| "A61" | 3-(6,7-Dihydro-1H-5,8-dioxa-1,3-diaza-cyclopenta[b]naphthalen-2-yl)-5-(1-piperidin-4-yl-1H-pyrazol-4-yl)pyridin-2-ylamine<br><br>hydrochloride | HPLC-MS<br>[M + H]$^+$<br>418.3 |
| "A62" | 2-[2-Amino-5-(1-piperidin-4-yl-1H-pyrazol-4-yl)pyridin-3-yl]-1H-benzimidazole-5-sulfonamide<br><br>formate | HPLC-MS<br>[M + H]$^+$<br>439.2 |
| "A63" | N-(4-{2-[2-Amino-5-(1-piperidin-4-yl-1H-pyrazol-4-yl)-pyridin-3-yl]-3H-benzimidazol-5-yloxy}phenyl)acetamide<br><br>formate | HPLC-MS<br>[M + H]$^+$<br>509.2 |
| "A64" | 3-[6-(2-Aminoethyl)-1H-benzimidazol-2-yl]-5-(1-methyl-1H-pyrazol-4-yl)pyridin-2-ylamine<br><br>trifluoroacetate | APCI-MS<br>[M + H]$^+$<br>334.3 |

| No. | Name and/or structure | Analysis |
|---|---|---|
| "A65" | Ethyl 2-[2-amino-5-(1-methyl-1H-pyrazol-4-yl)pyridin-3-yl]-3H-benzimidazole-5-carboxylate<br>trifluoroacetate | APCI-MS [M + H]+ 363.2 |
| "A66" | 3-(5,6-Dimethoxy-1H-benzimidazol-2-yl)-5-(1-piperidin-4-yl-1H-pyrazol-4-yl)pyridin-2-ylamine<br>hydrochloride | HPLC-MS [M + H]+ 420.2 |
| "A67" | 5-(1-Piperidin-4-yl-1H-pyrazol-4-yl)-3-(5-trifluoromethoxy-1H-benzimidazol-2-yl)pyridin-2-ylamine<br>formate | HPLC-MS [M + H]+ 444.2 |
| "A68" | {2-[2-Amino-5-(1-methyl-1H-pyrazol-4-yl)pyridin-3-yl]-3H-benzimidazol-5-yl}dimethylamine<br>trifluoroacetate | APCI-MS [M + H]+ 334.4 |

| No. | Name and/or structure | Analysis |
|---|---|---|
| "A69" | 3-(5-Fluoro-6-methoxy-1H-benzimidazol-2-yl)-5-(1-piperidin-4-yl-1H-pyrazol-4-yl)pyridin-2-ylamine<br>hydrochloride | HPLC-MS [M + H]⁺ 408.2 |

$^1$H NMR (400 MHz, DMSO-d$_6$ + TFA-d$_1$) δ [ppm] 9.10 (d, J = 2.0, 1H), 8.45 (d, J = 2.0, 1H), 8.39 (s, 1H), 8.10 (s, 1H), 7.63 (d, J = 11.1, 1H), 7.41 (d, J = 7.7, 1H), 4.65-4.55 (m, 1H), 3.96 (s, 3H), 3.47 (dd, J = 9.6, 3.6, 2H), 3.17 (td, J = 12.6, 2.9, 2H), 2.23 (dtd, J = 25.5, 13.4, 3.2, 4H)

| No. | Name and/or structure | Analysis |
|---|---|---|
| "A70" | 3-(6-Chloro-1H-benzimidazol-2-yl)-5-(1-piperidin-4-yl-1H-pyrazol-4-yl)pyridin-2-ylamine<br>hydrochloride | HPLC-MS [M + H]⁺ 394.2 |
| "A71" | 3-[6-Fluoro-5-(4-methylpiperazin-1-yl)-1H-benzimidazol-2-yl]-5-(1-piperidin-4-yl-1H-pyrazol-4-yl)pyridin-2-yl-amine<br>hydrochloride | APCI-MS [M + H]⁺ 476.3 |

| No. | Name and/or structure | Analysis |
|---|---|---|
| "A72" | 3-(5-Chloro-7-methyl-1H-benzimidazol-2-yl)-5-(1-piperidin-4-yl-1H-pyrazol-4-yl)pyridin-2-ylamine<br>hydrochloride | HPLC-MS [M + H]⁺ 408.2 |
| "A73" | 3-(6-Fluoro-5-morpholin-4-yl-1H-benzimidazol-2-yl)-5-(1-piperidin-4-yl-1H-pyrazol-4-yl)pyridin-2-ylamine<br>hydrochloride | HPLC-MS [M + H]⁺ 463.2 |
| "A74" | 3-(6-Fluoro-1H-benzimidazol-2-yl)-5-(1-methyl-1H-pyrazol-4-yl)pyridin-2-ylamine | HPLC-MS [M + H]⁺ 309.2 |
| "A75" | 5-(1-Methyl-1H-pyrazol-4-yl)-3-(4,5,6-trifluoro-1H-benzimidazol-2-yl)pyridin-2-ylamine | HPLC-MS [M + H]⁺ 345.2 |

| No. | Name and/or structure | Analysis |
|---|---|---|
| "A76" | 3-(4,6-Difluoro-1H-benzimidazol-2-yl)-5-(1-methyl-1H-pyrazol-4-yl)pyridin-2-ylamine | HPLC-MS [M + H]+ 327.2 |
| "A77" | {2-[2-Amino-5-(1-methyl-1H-pyrazol-4-yl)pyridin-3-yl]-3H-benzimidazol-5-yl}phenylmethanone<br><br>trifluoroacetate | ESI-MS [M + H]+ 395.2 |
| "A78" | 3-(6-Fluoro-5-methoxy-1H-benzimidazol-2-yl)-5-(1-methyl-1H-pyrazol-4-yl)pyridin-2-ylamine<br><br>¹H NMR (500 MHz, DMSO-d₆ + TFA-d₁) δ [ppm] 9.02 (d, J = 2.0, 1H), 8.39 (d, J = 2.0, 1H), 8.21 (s, 1H), 7.99 (s, 1H), 7.61 (d, J = 11.0, 1H), 7.41 (d, J = 7.7, 1H), 3.96 (d, J = 4.7, 6H) | HPLC-MS [M + H]+ 339.2 |
| "A79" | 5-(1-Methyl-1H-pyrazol-4-yl)-3-(4,5,6,7-tetrafluoro-1H-benzimidazol-2-yl)pyridin-2-ylamine | HPLC-MS [M + H]+ 363.2 |

-continued

| No. | Name and/or structure | Analysis |
|---|---|---|
| "A80" | {2-[2-Amino-5-(1-methyl-1H-pyrazol-4-yl)pyridin-3-yl]-3H-benzimidazol-5-yl}phenylmethanol<br><br>trifluoroacetate | ESI-MS [M + H]+ 397.2 |
| "A81" | 3-(6-Benzyl-1H-benzimidazol-2-yl)-5-(1-methyl-1H-pyrazol-4-yl)pyridin-2-ylamine<br><br>trifluoroacetate | ESI-MS [M + H]+ 381.3 |
| "A82" | 3-(6-Methoxy-1H-benzimidazol-2-yl)-5-(1H-pyrazol-4-yl)-pyridin-2-ylamine | HPLC-MS [M + H]+ 307.2 |
| "A83" | 2-[2-Amino-5-(1-methyl-1H-pyrazol-4-yl)pyridin-3-yl]-1H-benzimidazole-5-sulfonamide | HPLC-MS [M + H]+ 370.0 |

EXAMPLE 7

Preparation of 5-(6-methoxy-1H-benzimidazol-2-yl)-6'-piperazin-1-yl-[3,3']-bipyridinyl-6-ylamine ("A84") [method 1 route B]

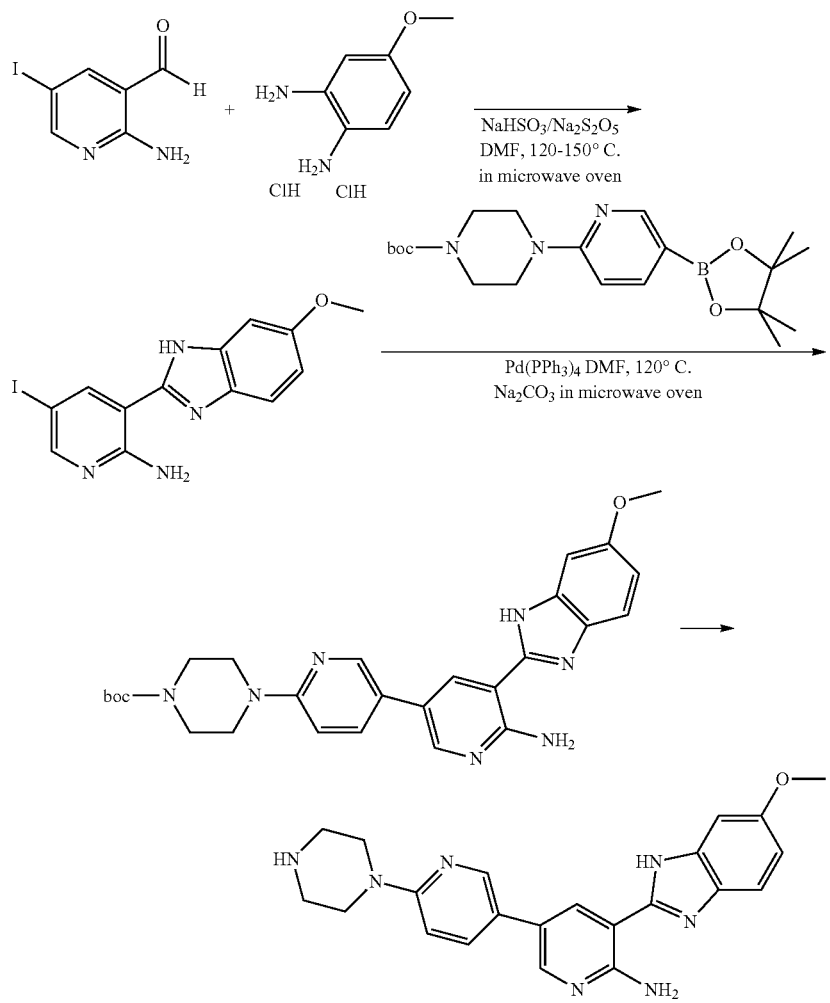

7.1 Cyclisation to the Benzimidazole:

3 ml (15.222 mmol) of 38-40% sodium hydrogensulfite solution are added to a solution of 1.355 g (5.462 mmol) of 2-amino-5-iodopyridine-3-carbaldehyde and 1.412 g (6.554 mmol) of 4-methoxyphenylene-1,2-diamine dihydrochloride in 17 ml of DMF, and the mixture is irradiated with microwaves for 30 min at 150° C. in the Biotage SmithSynthesizer. The reaction mixture is cooled to room temperature and evaporated to dryness. Water is added to the residue, and the mixture is extracted 3 times with ethyl acetate. The combined organic phases are dried using sodium sulfate, filtered and evaporated to dryness. The product is then crystallised from MTBE: 5-iodo-3-(5-methoxy-1H-benzimidazol-2-yl)pyridin-2-ylamine; HPLC-MS [M+H]$^+$ 367.0.

7.2 Suzuki Coupling:

128.87 mg (0.273 mmol) of 5-iodo-3-(5-methoxy-1H-benzimidazol-2-yl)pyridin-2-ylamine and 191.38 mg (0.492 mmol) of tert-butyl 4-[5-(4,4,5,5-tetramethyl-1,3,2-dioxaborolan-2-yl)pyridin-2-yl]piperazine-1-carboxylate are suspended in 2.5 ml of N,N-dimethylformamide in a nitrogen-filled microwave vessel, and 0.6 ml (1.2 mmol) of 2M sodium carbonate solution and 31.5 mg (0.027 mmol) of tetrakis(triphenylphosphine)palladium(0) are added. The reaction solution is irradiated with microwaves for 30 min at 120° C. in the Biotage SmithSynthesizer. The reaction mixture is cooled to room temperature and diluted with water/ethyl acetate and filtered. The aqueous phase is extracted a further 2× with ethyl acetate, and the combined organic phases are dried using sodium sulfate, filtered and evaporated to dryness. The residue is purified by means of RP-HPLC, giving tert-butyl 4-[6'-amino-5'-(6-methoxy-1H-benzimidazol-2-yl)-[3,3']bipyridinyl-6-yl]-piperazine-1-carboxylate.

7.3 BOC Removal:

3 ml of 4M HCl in dioxane are added to tert-butyl 4-[6'-amino-5'-(6-methoxy-1 H-benzimidazol-2-yl)-[3,3']bipyridinyl-6-yl]piperazine-1-carboxylate, and the mixture is stirred at room temperature for 14 h. The reaction mixture is evaporated to dryness, and water is added. The aqueous phase is adjusted to pH>10 using 2N NaOH and extracted 3× with ethyl acetate. The organic phases are dried using sodium sulfate, filtered and evaporated. The residue is purified by means of RP-HPLC and lyophilised, giving 5-(6-methoxy-1H-benzimidazol-2-yl)-6'-piperazin-1-yl-[3,3']bipyridinyl-6-ylamine as free base; HPLC-MS [M+H]$^+$ 402.2.

In general, the Boc removal is carried out using the standard methods of 4N HCl in dioxane or TFA/DCM, and the substances are isolated as free base, HCl or TFA salt.

The following compounds are obtained analogously

| No. | Name and/or structure | Analysis |
|---|---|---|
| "A85" | 3-(1H-Benzimidazol-2-yl)-5-(2H-pyrazol-3-yl)pyridin-2-ylamine | ESI-MS [M + H]$^+$ 277.2 |
| "A86" | 3-(1H-Benzimidazol-2-yl)-5-(2-methyl-2H-pyrazol-3-yl)-pyridin-2-ylamine | HPLC-MS [M + H]$^+$ 291.2 |
| "A87" | 3-(4-Ethoxy-1H-benzimidazol-2-yl)-5-(2H-pyrazol-3-yl)pyridin-2-ylamine | HPLC-MS [M + H]$^+$ 321.0 |
| "A88" | 3-(4-Ethoxy-1H-benzimidazol-2-yl)-5-(1-methyl-1H-pyrazol-4-yl)pyridin-2-ylamine | HPLC-MS [M + H]$^+$ 335.2 |

| No. | Name and/or structure | Analysis |
|---|---|---|
| "A89" | 3-(7-Methyl-1H-benzimidazol-2-yl)-5-(1-piperidin-4-yl-1H-pyrazol-4-yl)pyridin-2-ylamine<br><br>hydrochloride<br><br>$^1$H NMR (500 MHz, DMSO-d$_6$ + TFA-d$_1$) δ [ppm] 9.03 (d, J = 2.1, 1H), 8.45 (d, J = 2.1, 1H), 8.30 (s, 1H), 8.04 (s, 1H), 7.54 (d, J = 8.0, 1H), 7.29-7.25 (m, 1H), 7.16 (d, J = 7.3, 1H), 4.61-4.53 (m, 1H), 3.44 (d, J = 13.1, 2H), 3.14 (td, J = 12.7, 3.2, 2H), 2.62 (s, 3H), 2.29-2.15 (m, 4H) | HPLC-MS [M + H]$^+$ 374.2 |
| "A90" | 3-[5-(4-Methylpiperazin-1-yl)-1H-benzimidazol-2-yl]-5-(1-methyl-1H-pyrazol-4-yl)pyridin-2-ylamine | HPLC-MS [M + H]$^+$ 389.2 |
| "A91" | Ethyl {2-[2-amino-5-(1-methyl-1H-pyrazol-4-yl)pyridin-3-yl]-1H-benzimidazol-5-yl}acetate | HPLC-MS [M + H]$^+$ 377.2 |
| "A92" | 3-(6-Methoxy-1H-benzimidazol-2-yl)-5-(1-piperidin-4-yl-1H-pyrazol-4-yl)pyridin-2-ylamine<br><br>$^1$H NMR (400 MHz, DMSO-d$_6$ + TFA-d$_1$) δ [ppm] 9.01 (d, J = 2.0, 1H), 8.45 (d, J = 2.1, 1H), 8.35 (s, 1H), 8.08 (s, 1H), 7.68 (d, J = 8.9, 1H), 7.23 (d, J = 2.3, 1H), 7.03 (dd, J = 8.9, 2.4, 1H), 4.66-4.55 (m, 1H), 3.88 (s, 3H), 3.52-3.43 (m, 2H), 3.18 (td, J = 12.8, 3.1, 2H), 2.23 (dtd, J = 15.9, 13.6, 3.6, 4H) | HPLC-MS [M + H]$^+$ 390.2 |

-continued

| No. | Name and/or structure | Analysis |
|---|---|---|
| "A93" | 2-[2-Amino-5-(1-methyl-1H-pyrazol-4-yl)pyridin-3-yl]-1H-benzimidazole-4-carboxylic acid | HPLC-MS [M + H]$^+$ 335.2 |
| "A94" | 5-[1-(2-Dimethylaminoethyl)-1H-pyrazol-4-yl]-3-(6-methoxy-1H-benzimidazol-2-yl)pyridin-2-ylamine | HPLC-MS [M + H]$^+$ 378.2 |
| "A95" | 6'-Methoxy-5-(6-methoxy-1H-benzimidazol-2-yl)-[3,3']bipyridinyl-6-ylamine | HPLC-MS [M + H]$^+$ 348.2 |
| "A96" | 5-[1-(3-Dimethylaminopropyl)-1H-pyrazol-4-yl]-3-(6-methoxy-1H-benzimidazol-2-yl)pyridin-2-ylamine | HPLC-MS [M + H]$^+$ 392.2 |
| "A97" | 3-(6-Methoxy-1H-benzimidazol-2-yl)-5-(1H-pyrrol-2-yl)-pyridin-2-ylamine | HPLC-MS [M + H]$^+$ 306.2 |

-continued

| No. | Name and/or structure | Analysis |
|---|---|---|
| "A98" | 3-(6-Methoxy-1H-benzimidazol-2-yl)-5-(4-methyl-3,4-dihydro-2H-pyrido[3,2-b]-1,4-oxazin-7-yl)pyridin-2-yl-amine | HPLC-MS [M + H]$^+$ 389.2 |
| "A99" | 5-(6-Methoxy-1H-benzimidazol-2-yl)-[3,3']bipyridinyl-6,6'-diamine | HPLC-MS [M + H]$^+$ 333.2 |
| "A100" | 5-Benzo[b]thiophen-2-yl-3-(6-methoxy-1H-benzimidazol-2-yl)pyridin-2-ylamine | HPLC-MS [M + H]$^+$ 373.0 |
| "A101" | 5-Isoxazol-4-yl-3-(6-methoxy-1H-benzimidazol-2-yl)-pyridin-2-ylamine | ESI-MS [M + H]$^+$ 308.2 |
| "A102" | 2-[2-Amino-5-(1-methyl-1H-pyrazol-4-yl)pyridin-3-yl]-1H-benzimidazol-4-ol | HPLC-MS [M + H]$^+$ 307.2 |

-continued

| No. | Name and/or structure | Analysis |
|---|---|---|
| "A103" | 5-Benzofuran-2-yl-3-(6-methoxy-1H-benzimidazol-2-yl)pyridin-2-ylamine | HPLC-MS [M + H]⁺ 357.2 |
| "A104" | 5-(6-Methoxy-1H-benzimidazol-2-yl)-N6',N6'-dimethyl-[3,3']bipyridinyl-6,6'-diamine | HPLC-MS [M + H]⁺ 361.2 |
| "A105" | 5-(1-Ethyl-1H-pyrazol-4-yl)-3-(6-methoxy-1H-benzimidazol-2-yl)pyridin-2-ylamine hydrochloride $^1$H NMR (500 MHz, DMSO-d$_6$ + TFA-d$_1$) δ [ppm] 8.99 (d, J = 2.0, 1H), 8.40 (d, J = 1.9, 1H), 8.27 (s, 1H), 8.00 (s, 1H), 7.67 (d, J = 8.9, 1H), 7.22 (d, J = 2.3, 1H), 7.02 (dd, J = 8.8, 2.4 1H), 4.23 (q, J = 7.3, 2H), 3.87 (s, 3H), 1.46 (t, J = 7.3, 3H) | HPLC-MS [M + H]⁺ 335.2 |
| "A106" | 3-(6-Methoxy-1H-benzimidazol-2-yl)-5-[1-(1-methyl-piperidin-4-yl)-1H-pyrazol-4-yl]pyridin-2-ylamine hydrochloride $^1$H NMR (500 MHz, DMSO-d$_6$ + TFA-d$_1$) δ [ppm] 9.01 (d, J = 2.0, 1H), 8.46 (d, J = 2.0, 1H), 8.36 (s, 1H), 8.09 (s, 1H), 7.69 (d, J = 8.8, 1H), 7.24 (d, J = 2.2, 1H), 7.04 (dd, J = 8.9, 2.4, 1H), 4.61-4.53 (m, 1H), 3.88 (s, 3H), 3.65 (d, J = 12.8, 2H), 3.26 (t, J = 11.9, 2H), 2.91-2.86 (m, 3H), 2.40-2.19 (m, 4H) | HPLC-MS [M + H]⁺ 404.2 |

| No. | Name and/or structure | Analysis |
|---|---|---|
| "A107" | 5-(1-Isopropyl-1H-pyrazol-4-yl)-3-(6-methoxy-1H-benzimidazol-2-yl)pyridin-2-ylamine | HPLC-MS [M + H]+ 349.2 |

$^1$H NMR (400 MHz, DMSO-d$_6$ + TFA-d$_1$) δ [ppm] 8.97 (d, J = 2.1, 1H), 8.39 (d, J = 2.1, 1H), 8.29 (s, 1H), 7.98 (d, J = 0.6, 1H), 7.65 (d, J = 8.9, 1H), 7.20 (d, J = 2.3, 1H), 7.00 (dd, J = 8.9, 2.4, 1H), 4.56 (hept, J = 6.7, 1H), 3.85 (s, 3H), 1.48 (d, J = 6.7, 6H)

| No. | Name and/or structure | Analysis |
|---|---|---|
| "A108" | 3-(6-Methoxy-1H-benzimidazol-2-yl)-5-(1-propyl-1H-pyrazol-4-yl)pyridin-2-ylamine | HPLC-MS [M + H]+ 349.2 |
| "A109" | 5-(6-Methoxy-1H-benzimidazol-2-yl)-6'-methyl-[3,3']bipyridinyl-6-ylamine | HPLC-MS [M + H]+ 332.2 |
| "A110" | 2'-Fluoro-5-(6-methoxy-1H-benzimidazol-2-yl)-6'-methyl-[3,3']bipyridinyl-6-ylamine | HPLC-MS [M + H]+ 350.2 |
| "A111" | 6'-Amino-5'-(1H-benzimidazol-2-yl)-[3,3']bipyridinyl-6-carbonitrile | HPLC-MS [M + H]+ 313.2 |

-continued

| No. | Name and/or structure | Analysis |
|---|---|---|
| "A112" | N,N-Dimethyl-4-[6-amino-5-(6-methoxy-1H-benzimidazol-2-yl)pyridin-3-yl]pyrazole-1-carboxamide 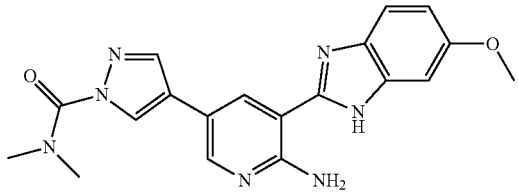 | HPLC-MS [M + H]⁺ 378.2 |
| "A113" | 3-(6-Methoxy-1H-benzimidazol-2-yl)-5-(1-thiophen-2-ylmethyl-1H-pyrazol-4-yl)pyridin-2-ylamine 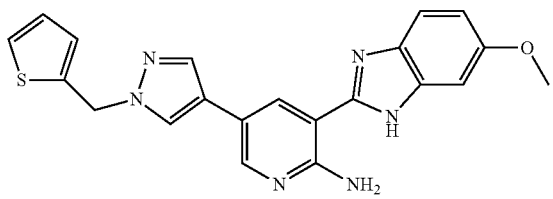 [SMILES: COc1ccc2nc(-c3cc(-c4cnn(Cc5cccs5)c4)cnc3N)[nH]c2c1] | HPLC-MS [M + H]⁺ 403.2 |
| "A114" | 3-(1H-Benzimidazol-2-yl)-5-(1-piperidin-4-yl-1H-pyrazol-4-yl)pyridin-2-ylamine 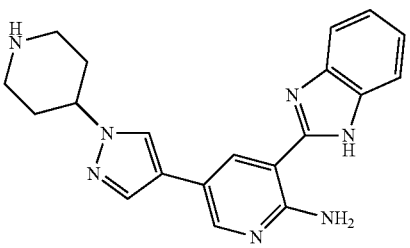 [SMILES: Nc1ncc(-c2cnn(C3CCNCC3)c2)cc1-c1nc2ccccc2[nH]1] hydrochloride  $^1$H NMR (400 MHz, DMSO-d$_6$ + TFA-d$_1$) δ [ppm] 9.31 (d, J = 2.0, 1H), 8.53 (d, J = 1.9, 1H), 8.50 (s, 1H), 8.16 (s, 1H), 7.78 (dd, J = 6.1, 3.1, 2H), 7.39 (dd, J = 6.1, 3.1, 2H), 4.66-4.55 (m, 1H), 3.47 (d, J = 13.0, 2H), 3.18 (td, J = 12.3, 2.7, 2H), 2.35-2.16 (m, 4H) | EI-MS [M]⁺ 359.3 |
| "A115" | 3-(1,7-Dihydroimidazo[4,5-f]indazol-6-yl)-5-(1-methyl-1H-pyrazol-4-yl)pyridin-2-ylamine 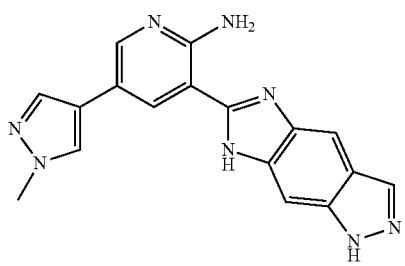 [SMILES: Cn1cc(-c2cnc(N)c(-c3nc4cc5cn[nH]c5cc4[nH]3)c2)cn1] | HPLC-MS [M + H]⁺ 331.2 |

-continued

| No. | Name and/or structure | Analysis |
|---|---|---|
| "A116" | 3-(5-Methoxy-1H-benzimidazol-2-yl)-5-[2-(4-methyl-piperazin-1-yl)thiazol-4-yl]pyridin-2-ylamine<br />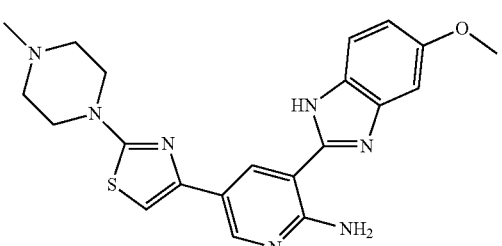 | HPLC-MS [M + H]+ 422.2 |

EXAMPLE 8

Preparation of 3-(1H-imidazo[4,5-b]pyridin-2-yl)-5-(1-methyl-1H-pyrazol-4-yl)pyridin-2-ylamine ("A117") [method 2]

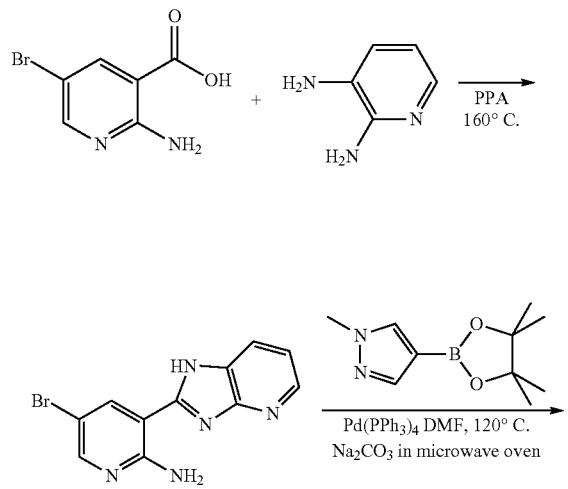

8.1 Cyclisation to the Benzimidazole:

50 mg (0.230 mmol) I) of 2-amino-5-bromonicotinic acid and 27.6 mg (0.253 mmol) of pyridine-2,3-diamine are added to 451.5 mg (5 mmol) of polyphosphoric acid, and the mixture is stirred at 160° C. for 4 days. The reaction mixture is cooled to room temperature, water is added, and the mixture is adjusted to pH 12 by means of 1N NaOH. The precipitate formed is filtered off with suction and dried, giving 5-bromo-3-(1H-imidazo[4,5-b]pyridin-2-yl)pyridin-2-ylamine.

8.2 Suzuki Coupling:

58 mg (0.200 mmol) of 5-bromo-3-(1H-imidazo[4,5-b]pyridin-2-yl)pyridin-2-ylamine and 45.8 mg (0.220 mmol) of 1-methyl-4-(4,4,5,5-tetramethyl-1,3,2-dioxaborolan-2-yl)-1H-pyrazole are suspended in 2 ml of N,N-dimethylformamide in a nitrogen-filled microwave vessel, and 0.57 ml (1.142 mmol) of 2M sodium carbonate solution and 23.1 mg (0.020 mmol) of tetrakis(triphenylphosphine)palladium(0) are added. The reaction solution is irradiated with microwaves for 30 min at 120° C. in the Biotage SmithSynthesizer. The reaction mixture is evaporated to dryness, and the residue is purified by means of RP-HPLC, giving 3-(1H-imidazo[4,5-b]pyridin-2-yl)-5-(1-methyl-1H-pyrazol-4-yl)pyridin-2-ylamine; HPLC-MS [M+H]+ 292.2;

$^1$H NMR (500 MHz, DMSO-d$_6$+TFA-d$_1$) δ [ppm] 9.16 (d, J=2.1, 1H), 8.67 (dd, J=5.3, 1.1, 1H), 8.56 (d, J=7.8, 1H), 8.52 (d, J=2.1, 1H), 8.20 (s, 1H), 7.99 (s, 1H), 7.65 (dd, J=8.0, 5.4, 1H), 3.92 (s, 3H).

An analogous procedure gives the compound 3-(6-methyl-7H-purin-8-yl)-5-(1-methyl-11H-pyrazol-4-yl)pyridin-2-ylamine ("A118")

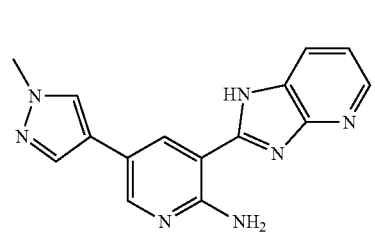

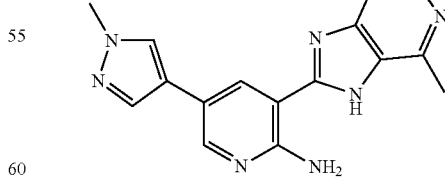

[Suzuki conditions: tripotassium phosphate trihydrate instead of sodium carbonate]; HPLC-MS [M+H]+ 307.2;

$^1$H NMR (400 MHz, DMSO-d$_6$) δ [ppm]

EXAMPLE 9

Preparation of 2-{2-[2-amino-5-(1-methyl-1H-pyrazol-4-yl)pyridin-3-yl]-1H-benzimidazol-5-yl}-N-(3,4-difluorobenzyl)acetamide ("A119")

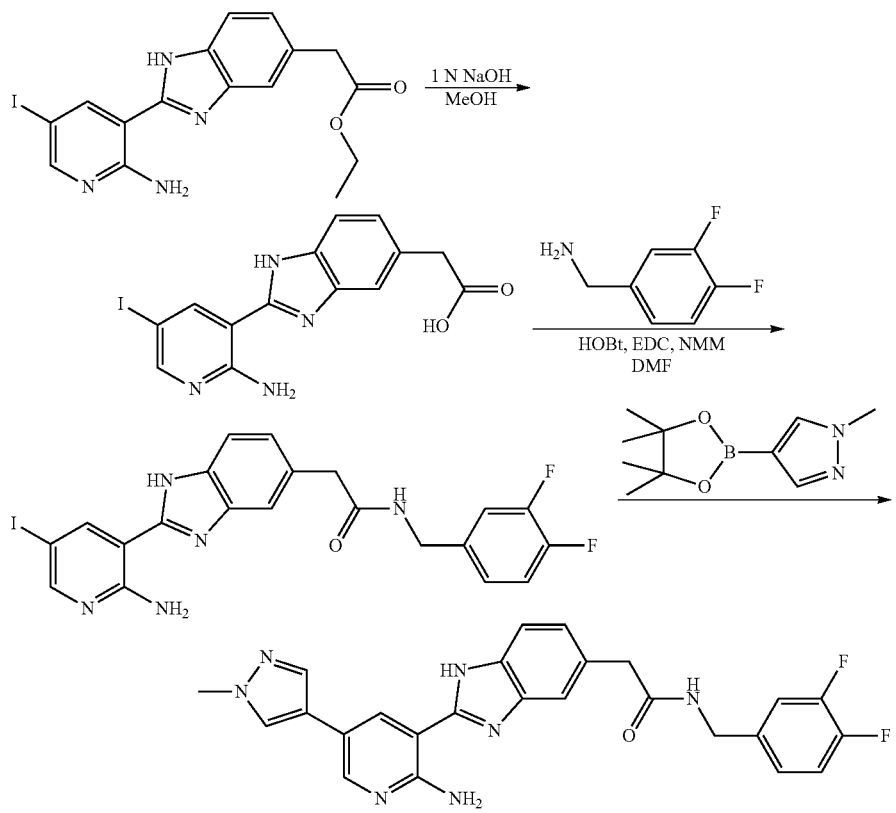

9.1 Ethyl [2-(2-amino-5-iodopyridin-3-yl)-1H-benzimidazol-5-yl]acetate is prepared analogously to method 1 route B.

9.2 51 mg (0.121 mmol) of ethyl [2-(2-amino-5-iodopyridin-3-yl)-1H-benzimidazol-5-yl]acetate are dissolved in 5 ml of methanol, and 242 µl of 1N NaOH (0.242 mmol) are added. The reaction mixture is irradiated for 10 min at 100° C. in a microwave unit. After cooling, it is evaporated to dryness and adjusted to pH 4-5 by means of 1N HCl. The precipitate formed is filtered off with suction and dried, giving [2-(2-amino-5-iodopyridin-3-yl)-1H-benzimidazol-5-yl]acetic acid; HPLC-MS [M+H]$^+$ 395.0.

9.3 44 mg of [2-(2-amino-5-iodopyridin-3-yl)-1H-benzimidazol-5-yl]acetic acid (0.112 mmol) are dissolved in 2 ml of DMF. 17.5 mg (0.123 mmol) of 3,4-difluorobenzylamine, 22.4 mg (0.145 mmol) of HOBt, 23.5 mg (0.123 mmol) of EDC and 12.9 µl (0.117 mmol) of N-methylmorpholine are added. The reaction mixture is stirred at room temperature for 3 days, and water is then added. The precipitate formed is filtered off with suction, washed with water and freeze-dried, giving: 2-[2-(2-amino-5-iodopyridin-3-yl)-1H-benzimidazol-5-yl]-N-(3,4-difluorobenzyl)acetamide; HPLC-MS [M+H]$^+$ 520.0.

9.4 Under standard Suzuki conditions (method 1 route B), 2-{2-[2-amino-5-(1-methyl-1H-pyrazol-4-yl)pyridin-3-yl]-1H-benzimidazol-5-yl}-N-(3,4-difluorobenzyl)acetamide is obtained HPLC-MS [M+H]$^+$ 474.2;

$^1$H NMR (400 MHz, DMSO-d$_6$+TFA-d$_1$) δ [ppm] 9.05 (d, J=2.1, 1H), 8.46 (d, J=2.1, 1 H), 8.24 (s, 1H), 8.02 (d, J=0.7, 1 H), 7.76-7.71 (m, 2H), 7.39-7.23 (m, 3H), 7.13 (s, 1H), 4.33 (s, 2H), 3.98 (s, 3H), 3.72 (s, 2H).

EXAMPLE 10

Preparation of 2-{2-[2-amino-5-(1-methyl-1H-pyrazol-4-yl)pyridin-3-yl]-1H-benzimidazol-5-yl}acetamide ("A120")

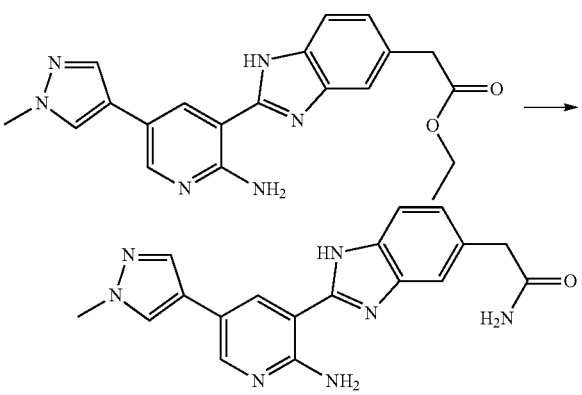

An excess of ammonia solution is added to a solution of "A91" in methanol. The reaction mixture is stirred at room temperature for 14 h. The solvent is then separated off. The residue is purified by means of preparative HPLC, giving 2-{2-[2-amino-5-(1-methyl-1H-pyrazol-4-yl)pyridin-3-yl]-1H-benzimidazol-5-yl}acetamide trifluoroacetate; APCI-MS [M+H]⁺ 348;

¹H NMR (400 MHz, DMSO-d₆+TFA-d₁) δ [ppm] 8.98 (d, J=2.0, 1H), 8.39 (d, J=2.0, 1H), 8.19 (s, 1H), 7.97 (s, 1H), 7.67 (d, J=8.4, 1 H), 7.63 (d, J=0.7, 1H), 7.28 (dd, J=8.4, 1.5, 1H), 3.92 (s, 3H), 3.56 (s, 2H).

The following compounds are obtained analogously

2-{2-[2-amino-5-(1-methyl-1H-pyrazol-4-yl)pyridin-3-yl]-3H-benzimidazol-5-yl}-N-methylacetamide trifluoroacetate ("A121")

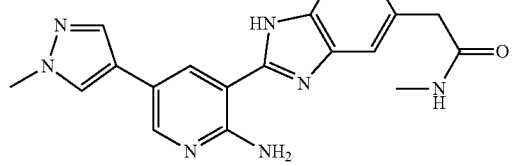

ESI-MS [M+H]⁺ 362.3;

¹H NMR (500 MHz, DMSO-d₆+TFA-d₁) δ [ppm] 9.02 (d, J=2.1, 1H), 8.44 (d, J=2.1, 1H), 8.21 (s, 1H), 8.00 (s, 1H), 7.69 (dd, J=13.8, 4.4, 2H), 7.32 (dd, J=8.4, 1.4, 1H), 3.95 (s, 3H), 3.62 (s, 2H), 2.64 (s, 3H);

2-{2-[2-amino-5-(1-methyl-1H-pyrazol-4-yl)pyridin-3-yl]-3H-benzimidazol-5-yl}-N-methylacetamide trifluoroacetate ("A122")

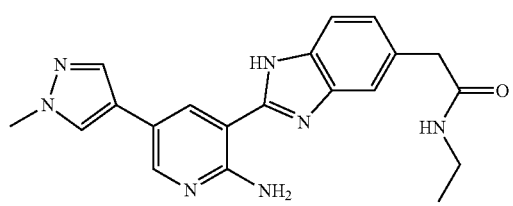 [SMILES: CCNC(=O)Cc1ccc2[nH]c(-c3cc(-c4cnn(C)c4)cnc3N)nc2c1]

ESI-MS [M+H]⁺ 376.3;

¹H NMR (500 MHz, DMSO-d₆+TFA-d₁) δ [ppm] 9.02 (d, J=2.1, 1H), 8.44 (d, J=2.1, 1H), 8.21 (s, 1H), 8.00 (d, J=0.5, 1H), 7.71 (d, J=8.4, 1H), 7.68 (s, 1H), 7.33 (dd, J=8.4, 1.4, 1H), 3.95 (s, 3H), 3.61 (s, 2H), 3.13 (q, J=7.2, 2H), 1.07 (t, J=7.2, 3H).

EXAMPLE 11

Preparation of N-isopropyl-2-[2-amino-5-(1-methyl-1H-pyrazol-4-yl)pyridin-3-yl]-3H-benzimidazole-5-carboxamide ("A123")

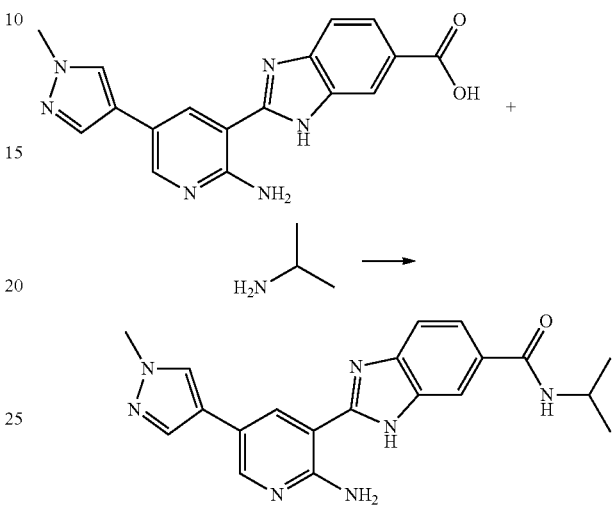

70 mg of "A51" (0.209 mmol) are dissolved in 10 ml of DMF. 54 µl (0.630 mmol) of isopropylamine, 28 mg (0.210 mmol) of HOBt, 81 mg (0.420 mmol) of EDC and 69.2 µl (0.630 mmol) of N-methylmorpholine are added. The reaction mixture is stirred at 80° C. for 2 days, and ethyl acetate is then added. The organic phase is washed 3× with water, dried using sodium sulfate, filtered, and the solvent is separated off. The residue is purified by means of RP-HPLC and lyophilised, giving N-isopropyl-2-[2-amino-5-(1-methyl-1H-pyrazol-4-yl)pyridin-3-yl]-3H-benzimidazole-5-carboxamide trifluoroacetate; ESI-MS [M+H]⁺ 376.3;

¹H NMR (500 MHz, DMSO-d₆+TFA-d₁) δ [ppm] 9.10 (d, J=2.1, 1H), 8.45 (d, J=2.1, 1H), 8.29 (d, J=1.0, 1H), 8.22 (s, 1H), 8.01 (d, J=0.5, 1H), 7.92 (dd, J=8.5, 1.6, 1 H), 7.78 (d, J=8.5, 1 H), 4.23-4.14 (m, 1H), 3.96 (s, 3H), 1.24 (d, J=6.6, 6H).

The following compounds are obtained analogously

| No. | Name and/or structure | Analysis |
|---|---|---|
| "A124" | N,N-Dimethyl-2-[2-amino-5-(1-methyl-1H-pyrazol-4-yl)pyridin-3-yl]-3H-benzimidazole-5-carboxamide<br><br>trifluoroacetate | APCI-MS [M + H]⁺ 362.3 |

¹H NMR (400 MHz, DMSO-d₆ + TFA-d₁) δ [ppm] 9.12 (d, J = 2.1, 1H), 8.46 (d, J = 2.0, 1H), 8.23 (s, 1H), 8.02 (d, J = 0.6, 1H), 7.82 (dd, J = 10.7, 4.8, 2H), 7.44 (dd, J = 8.3, 1.5, 1H), 3.97 (s, 3H), 3.05 (s, 6H)

-continued

| No. | Name and/or structure | Analysis |
|---|---|---|
| "A125" | tert-Butyl 4-({2-[2-amino-5-(1-methyl-1H-pyrazol-4-yl)-pyridin-3-yl]-3H-benzimidazole-5-carbonyl}amino)-piperidine-1-carboxylate | HPLC-MS [M + H]+ 517.2 |
| "A126" | N-Piperidin-4-yl-2-[2-amino-5-(1-methyl-1H-pyrazol-4-yl)pyridin-3-yl]-3H-benzimidazole-5-carboxamide dihydrochloride [by cleaving off BOC from "A125"] | HPLC-MS [M + H]+ 417.2 |
| "A127" | N-(2-Methoxyethyl)-2-[2-amino-5-(1-methyl-1H-pyrazol-4-yl)pyridin-3-yl]-1H-benzimidazole-4-carboxamide [by reaction of "A93" with 2-methoxyethylamine] | HPLC-MS [M + H]+ 392.2 |

$^1$H NMR (500 MHz, DMSO-$d_6$ + TFA-$d_1$) δ [ppm] 9.16 (d, J = 2.0, 1H), 8.46 (d, J = 2.0, 1H), 8.23 (s, 1H), 8.01 (s, 1H), 7.97-7.87 (m, 2H), 7.46 (t, J = 7.8, 1H), 3.92 (s, 3H), 3.60 (dt, J = 25.7, 5.2, 4H), 3.35 (s, 3H)

EXAMPLE 12

Preparation of N-[2-(3,4-difluorophenyl)ethyl]-2-[2-amino-5-(1-methyl-1H-pyrazol-4-yl)pyridin-3-yl]-3H-benzimidazole-5-carboxamide ("A128")

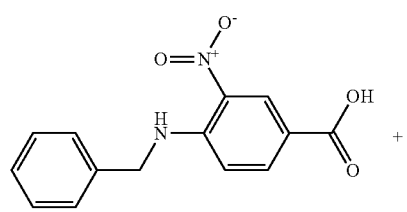

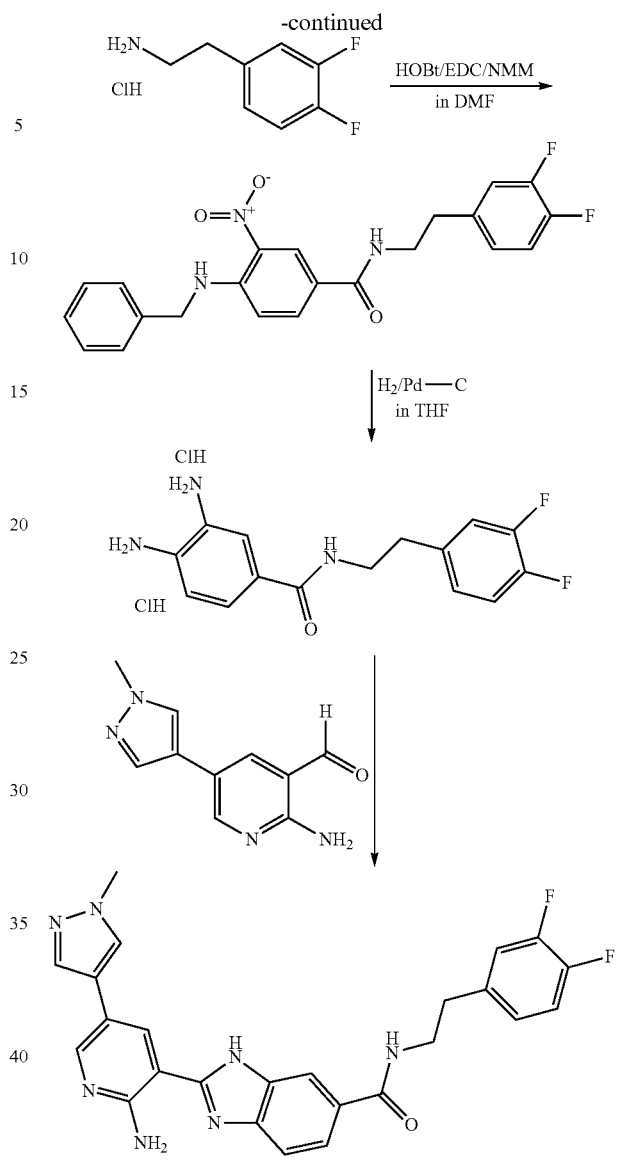

12.1 511 mg (1.877 mmol) of 4-benzylamino-3-nitrobenzoic acid are dissolved in 20 ml of DMF. 1.092 g (5.640 mmol) of 2-(3,4-difluorophenyl)ethylamine hydrochloride, 254 mg (1.88 mmol) of HOBt, 729 mg (3.8 mmol) of EDC and 1.033 ml (9.4 mmol) of N-methylmorpholine are added. The reaction mixture is stirred at room temperature for 3 days, and ethyl acetate is then added. The organic phase is washed 3× with water, dried using sodium sulfate, filtered, and the solvent is removed.

12.2 4-Benzylamino-N-[2-(3,4-difluorophenyl)ethyl]-3-nitrobenzamide is hydrogenated under standard conditions, and the crude product is isolated as 3,4-diamino-N-[2-(3,4-difluorophenyl)ethyl]benzamide dihydrochloride.

12.3 279 μl (1.4 mmol) of 38-40% sodium hydrogensulfite solution are added to a solution of 56 mg (0.277 mmol) of 2-amino-5-(1-methyl-1H-pyrazol-4-yl)pyridine-3-carbaldehyde and 102 mg (0.280 mmol) of 3,4-diamino-N-[2-(3,4-difluorophenyl)ethyl]benzamide dihydrochloride in 5 ml of DMF, and the suspension formed is stirred at 50° C. for 14 h. The reaction mixture is cooled to RT, water is added, and the mixture is extracted 3× with dichloromethane/isopropanol. The organic phases are washed 2× with water and dried using sodium sulfate, filtered, and the solvent is removed. The residue is purified further by means of preparative RP-HPLC, giving N-[2-(3,4-difluorophenyl)ethyl]-2-[2-amino-5-(1-methyl-1H-pyrazol-4-yl)pyridin-3-yl]-3H-benzimidazole-5-carboxamide trifluoroacetate as yellow solid; APCI-MS [M+H]+ 474.3;

¹H NMR (500 MHz, DMSO-d$_6$+TFA-d$_1$) δ [ppm] 9.09 (d, J=2.1, 1H), 8.45 (d, J=2.1, 1H), 8.23 (s, 2H), 8.00 (d, J=0.5, 1H), 7.87 (dd, J=8.5, 1.6, 1H), 7.79 (d, J=8.4, 1H), 7.36-7.28 (m, 2H), 7.14-7.08 (m, 1H), 3.96 (s, 3H), 3.58 (t, J=7.1, 2H), 2.92 (t, J=7.1, 2H).

EXAMPLE 13

Preparation of N-piperidin-4-yl-2-[2-amino-5-(1-methyl-1H-pyrazol-4-yl)pyridin-3-yl]-1H-benzimidazole-4-carboxamide ("A129")

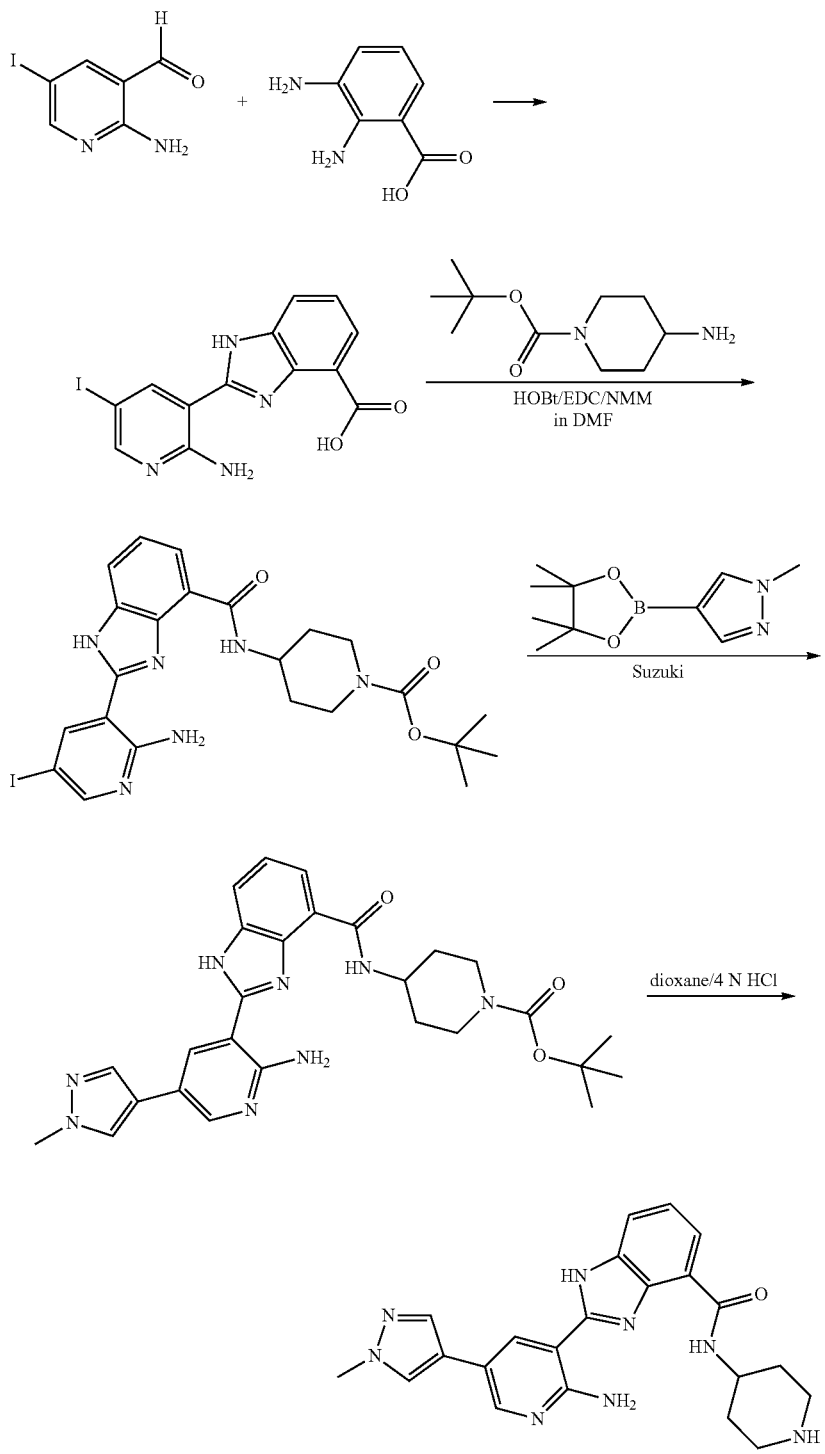

2-(2-Amino-5-iodopyridin-3-yl)-1H-benzimidazole-4-carboxylic acid is prepared by method 1 route B, and the amide coupling is carried out as in Example 14. This is followed by the Suzuki coupling as according to method 1 route B and the Boc removal using dioxane/4N HCl, giving N-piperidin-4-yl-2-[2-amino-5-(1-methyl-1H-pyrazol-4-yl)pyridin-3-yl]-1H-benzimidazole-4-carboxamide hydrochloride; HPLC-MS [M+H]⁺ 417.2;

¹H NMR (500 MHz, DMSO-d₆+TFA-d₁) δ [ppm] 9.24 (d, J=2.0, 1 H), 8.47 (d, J=2.1, 1H), 8.28 (s, 1H), 8.06 (s, 1H), 7.94 (t, J=7.6, 2H), 7.48 (t, J=7.8, 1H), 4.28-4.20 (m, 1H), 3.96 (s, 3H), 3.45-3.37 (m, 2H), 3.14 (td, J=12.5, 2.7, 2H), 2.17 (dd, J=14.1, 3.4, 2H), 1.94-1.83 (m, 2H).

EXAMPLE 14

Preparation of N-(2-methoxyethyl)-5-[6-amino-5-(6-methoxy-1H-benzimidazol-2-yl)pyridin-3-yl]thiophene-2-carboxamide ("A130")

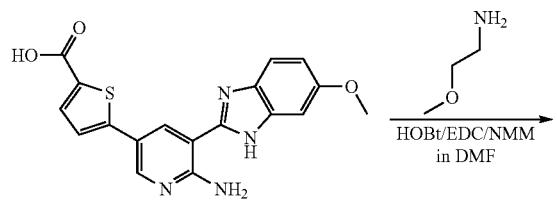

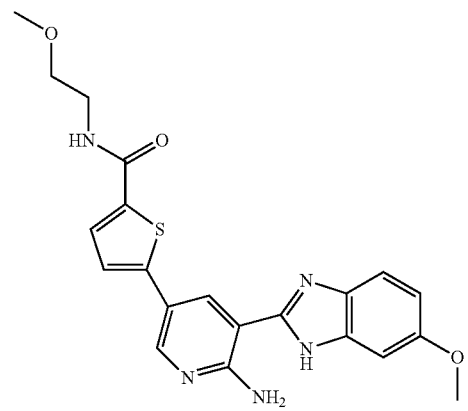

14.1 5-[6-Amino-5-(6-methoxy-1H-benzimidazol-2-yl)pyridin-3-yl]thiophene-2-carboxylic acid is prepared analogously to method 1 route B and reacted further as crude product.

14.2 157 mg (0.111 mmol) of 5-[6-amino-5-(6-methoxy-1H-benzimidazol-2-yl)pyridin-3-yl]thiophene-2-carboxylic acid are dissolved in 0.5 ml of DMF. 10 µl (0.114 mmol) of 2-methoxyethylamine, 14.9 mg (0.111 mmol) of HOBt, 21.2 mg (0.111 mmol) of EDC and 24.3 µl (0.221 mmol) of N-methylmorpholine are added. The reaction mixture is stirred at room temperature for 14 h, water is added, and the mixture is extracted with ethyl acetate. The organic phases are dried using sodium sulfate, filtered and evaporated. The residue is purified by means of RP-HPLC and lyophilised, giving N-(2-methoxyethyl)-5-[6-amino-5-(6-methoxy-1H-benzimidazol-2-yl)pyridin-3-yl]-thiophene-2-carboxamide; HPLC-MS [M+H]⁺ 424.2.

¹H NMR (400 MHz, DMSO-d₆+TFA-d₁) δ [ppm] 9.00 (d, J=2.1, 1H), 8.60 (d, J=2.0, 1 H), 7.90 (d, J=3.9, 1 H), 7.66 (dd, J=9.7, 6.4, 2H), 7.24-7.18 (m, 1H), 7.07-6.99 (m, 1H), 3.88 (s, 3H), 3.53-3.43 (m, 4H), 3.31 (s, 3H).

The following compounds are obtained analogously

| No. | Name and/or structure | Analysis |
|---|---|---|
| "A131" | N-(2-Dimethylaminoethyl)-5-[6-amino-5-(6-methoxy-1H-benzimidazol-2-yl)pyridin-3-yl]thiophene-2-carboxamide 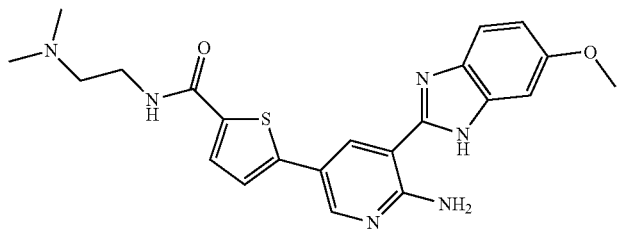 | HPLC-MS [M + H]⁺ 437.2 |

| No. | Name and/or structure | Analysis |
|---|---|---|
| "A132" | N-Piperidin-4-yl-5-[6-amino-5-(6-methoxy-1H-benzimidazol-2-yl)pyridin-3-yl]thiophene-2-carboxamide<br><br>[final step: cleaving off of the BOC protecting group in HCl/dioxane] | HPLC-MS [M + H]$^+$ 449.2 |
| "A133" | N-(1-Methylpiperidin-4-yl)-5-[6-amino-5-(6-methoxy-1H-benzimidazol-2-yl)pyridin-3-yl]thiophene-2-carboxamide<br><br>$^1$H NMR (500 MHz, DMSO-d$_6$ + TFA-d$_1$) δ [ppm] 9.02 (d, J = 2.2, 1H), 8.60 (d, J = 2.1, 1H), 7.92 (d, J = 3.9, 1H), 7.67 (dd, J = 6.3, 4.4, 2H), 7.22 (d, J = 2.2, 1H), 7.04 (dd, J = 8.9, 2.4, 1H), 4.11-4.00 (m, 1H), 3.89 (s, 3H), 3.53 (d, J = 12.6, 2H), 3.16 (td, J = 13.1, 2.2, 2H), 2.83 (s, 3H), 2.10 (dd, J = 13.6 2.7, 2H), 1.91-1.76 (m, 2H) | HPLC-MS [M + H]$^+$ 463.2 |
| "A134" | N-(Pyridin-4-ylmethyl)-5-[6-amino-5-(6-methoxy-1H-benzimidazol-2-yl)pyridin-3-yl]thiophene-2-carboxamide<br><br>$^1$H NMR (500 MHz, DMSO-d$_6$ + TFA-d$_1$) δ [ppm] 9.02 (d, J = 2.1, 1H), 8.93 (d, J = 6.8, 2H), 8.62 (d, J = 2.1, 1H), 8.06 (d, J = 6.7, 2H), 7.99 (d, J = 3.9, 1H), 7.71 (d, J = 3.9, 1H), 7.68 (d, J = 8.8, 1H), 7.22 (d, J = 2.3, 1H), 7.04 (dd, J = 8.9, 2.4, 1H), 4.82 (s, 2H), 3.88 (s, 3H) | HPLC-MS [M + H]$^+$ 457.2 |

EXAMPLE 15

Preparation of N-(2-{2-[2-amino-5-(1-methyl-1H-pyrazol-4-yl)pyridin-3-yl]-3H-benzimidazol-5-yl}ethyl)-3,4-difluorobenzamide ("A135")

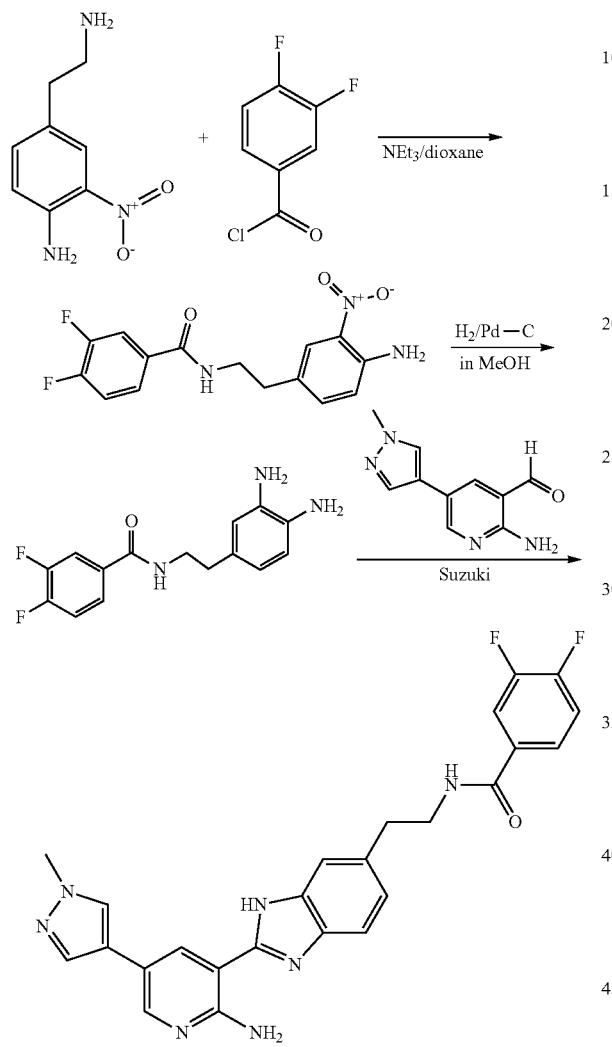

480 mg (2.649 mmol) of 4-(2-aminoethyl)-2-nitrophenylamine are dissolved in 30 ml of dioxane, and 1.102 ml (7.950 mmol) of triethylamine are added. 0.334 ml (2.650 mmol) of 3,4-difluorobenzoyl chloride are then added dropwise, and the mixture is stirred at room temperature for 30 min. Ethyl acetate is added to the reaction mixture, which is then washed 3× with water, dried using sodium sulfate, filtered and distilled off to dryness, giving N-[2-(4-amino-3-nitrophenyl)ethyl]-3,4-difluorobenzamide; EI-MS [M]$^+$ 321, which is hydrogenated further under standard conditions, giving N-[2-(3,4-diaminophenyl)ethyl]-3,4-difluorobenzamide; HPLC-MS [M+H]$^+$ 292.2.

The cyclisation to the benzimidazole is carried out in accordance with the conditions of method 1 route A, giving N-(2-{2-[2-amino-5-(1-methyl-1H-pyrazol-4-yl)pyridin-3-yl]-3H-benzimidazol-5-yl}ethyl)-3,4-difluorobenzamide trifluoroacetate; HPLC-MS [M+H]$^+$ 474.3;

$^1$H NMR (500 MHz, DMSO-d$_6$+TFA-d$_1$) δ [ppm] 9.02 (d, J=2.0, 1H), 8.43 (d, J=2.0, 1 H), 8.21 (s, 1H), 7.99 (s, 1H), 7.92-7.83 (m, 1H), 7.78-7.72 (m, 1H), 7.70 (d, J=8.3, 1H), 7.63 (s, 1H), 7.50 (dt, J=10.3, 8.4, 1H), 7.31 (dd, J=8.4, 1.2, 1H), 3.95 (s, 3H), 3.62 (t, J=7.2, 2H), 3.06 (t, J=7.2, 2H).

EXAMPLE 16

Preparation of 2-{2-[2-amino-5-(1-methyl-1H-pyrazol-4-yl)pyridin-3-yl]-3H-benzimidazol-4-yl}ethanol ("A136")

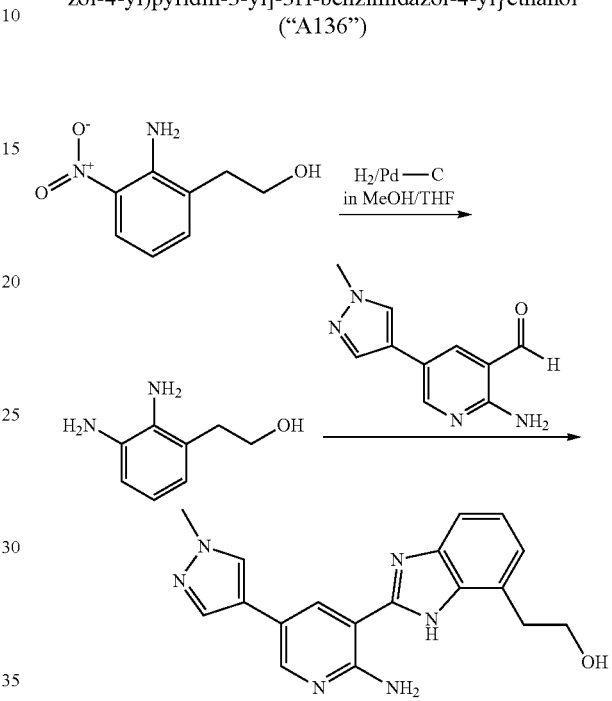

2-(2-Amino-3-nitrophenyl)ethanol is hydrogenated according to standard conditions to give 2-(2,3-diaminophenyl)ethanol; HPLC-MS [M+H]$^+$ 153.2. This is cyclised to the benzimidazole in accordance with method 1 route A, giving 2-{2-[2-amino-5-(1-methyl-1H-pyrazol-4-yl)pyridin-3-yl]-3H-benzimidazol-4-yl}ethanol; HPLC-MS [M+H]$^+$ 335.2;

$^1$H NMR (500 MHz, DMSO-d$_6$+TFA-d$_1$) δ [ppm] 9.06 (d, J=2.0, 1H), 8.43 (d, J=2.1, 1H), 8.22 (s, 1H), 7.99 (s, 1H), 7.58 (d, J=7.5, 1H), 7.33-7.27 (m, 1H), 7.22 (d, J=7.2, 1H), 3.94 (s, 3H), 3.82 (t, J=7.1, 2H), 3.20 (t, J=7.1, 2H).

EXAMPLE 17

Preparation of 3-[5-(4-methylpiperazine-1-sulfonyl)-1H-benzimidazol-2-yl]-5-(1-methyl-1H-pyrazol-4-yl)pyridin-2-ylamine ("A137")

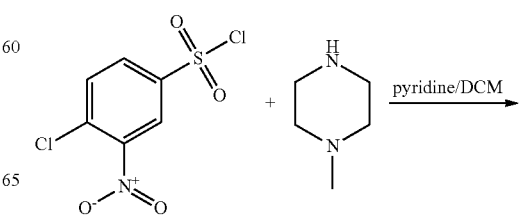

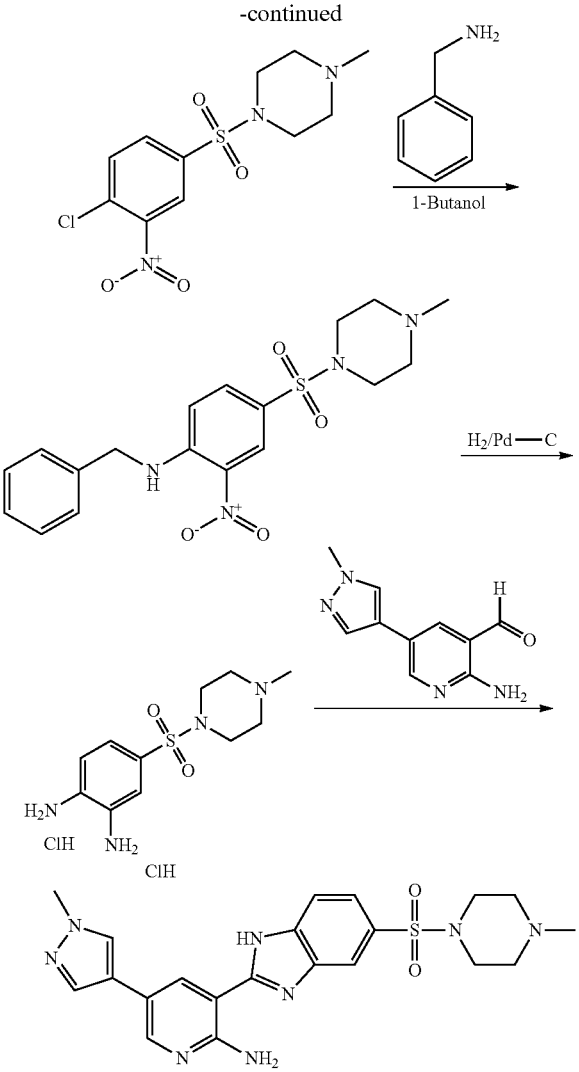

17.1 2.5 g (9.763 mmol) of 4-chloro-3-nitrobenzenesulfonyl chloride are dissolved in 100 ml of DCM. 1.574 ml (19.5 mmol) of pyridine and 1.086 ml (9.760 mmol) of N-methylpiperazine are added, and the mixture is stirred at room temperature for 14 h. The reaction mixture is washed 3× with water, the organic phase is dried using sodium sulfate, filtered, and the solvent is removed, giving 1-(4-chloro-3-nitrobenzenesulfonyl)-4-methylpiperazine; EI-MS [M]+ 319.

17.2 2.8 g (8.756 mmol) of 1-(4-chloro-3-nitrobenzenesulfonyl)-4-methylpiperazine are dissolved in 10 ml of 1-butanol, and 1.913 ml (17.5 mmol) of benzylamine are added. The reaction mixture is heated under reflux for 14 h. After cooling, MTBE is added, the precipitate formed is filtered off with suction and washed with MTBE and dried in vacuo, giving benzyl-[4-(4-methylpiperazine-1-sulfonyl)-2-nitrophenyl]amine; HPLC-MS [M+H]+ 391.2.

17.3 Benzyl-[4-(4-methylpiperazine-1-sulfonyl)-2-nitrophenyl]amine is hydrogenated under standard conditions to give 4-(4-methylpiperazine-1-sulfonyl)benzene-1,2-diamine and isolated as dihydrochloride; HPLC-MS [M+H]+ 271.2.

17.4 The cyclisation to the benzimidazole is carried out in accordance with method 1 route A, giving 3-[5-(4-methylpiperazine-1-sulfonyl)-1H-benzimidazol-2-yl]-5-(1-methyl-1H-pyrazol-4-yl)pyridin-2-ylamine; ESI-MS [M+H]+; 453.2 [2M+H]+ 905.0;

$^1$H NMR (500 MHz, DMSO-d$_6$+TFA-d$_1$) δ [ppm] 9.16 (d, J=2.1, 1H), 8.50 (d, J=1.8, 1H), 8.25 (s, 1H), 8.23 (d, J=1.5, 1H), 8.02 (t, J=4.2, 2H), 7.78 (dd, J=8.5, 1.6, 1H), 3.96 (s, 3H), 3.89 (d, J=13.2, 2H), 3.53 (d, J=12.3, 2H), 3.24 (td, J=12.0, 1.7, 2H), 2.83 (s, 3H), 2.63 (t, J=12.0, 2H).

The following compounds are obtained analogously

N-dimethyl-2-[2-amino-5-(1-methyl-1H-pyrazol-4-yl)pyridin-3-yl]-3H-benzimidazole-5-sulfonamide ("A138")

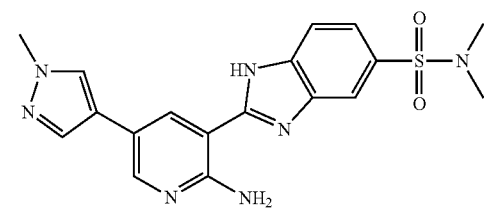

ESI-MS [M+H]+ 398.2;

$^1$H NMR (500 MHz, DMSO-d$_6$+TFA-d$_1$) δ [ppm] 9.13 (d, J=2.0, 1H), 8.48 (d, J=2.0, 1H), 8.24 (s, 1H), 8.15 (d, J=1.2, 1H), 8.01 (s, 1H), 7.97 (d, J=8.5, 1H), 7.74 (dd, J=8.5, 1.6, 1H), 3.96 (s, 3H), 2.67 (s, 6H);

N-ethyl-2-[2-amino-5-(1-methyl-1H-pyrazol-4-yl)pyridin-3-yl]-1H-benzimidazole-5-sulfonamide ("A139")

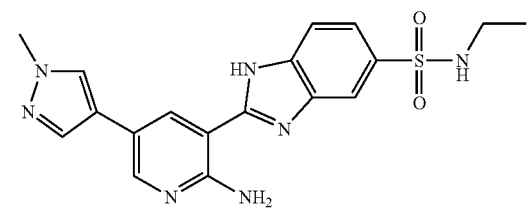 [SMILES: CCNS(=O)(=O)c1ccc2[nH]c(-c3cc(-c4cnn(C)c4)cnc3N)nc2c1]

EI-MS [M]+ 397.1;

$^1$H NMR (500 MHz, DMSO-d$_6$+TFA-d$_1$) δ [ppm] 9.08 (d, J=1.9, 1 H), 8.43 (d, J=2.0, 1H), 8.19 (s, 1H), 8.16 (d, J=1.4, 1H), 7.97 (d, J=2.3, 1H), 7.89 (d, J=8.5, 1H), 7.78 (dd, J=8.5, 1.5, 1H), 3.92 (s, 3H), 2.80 (q, J=7.2, 2H), 0.97 (t, J=7.2, 3H).

EXAMPLE 18

Preparation of N-(pyridin-4-ylmethyl)-2-[2-amino-5-(1-methyl-1H-pyrazol-4-yl)pyridin-3-yl]-5-fluoro-3H-benzimidazole-4-carboxamide ("A140")

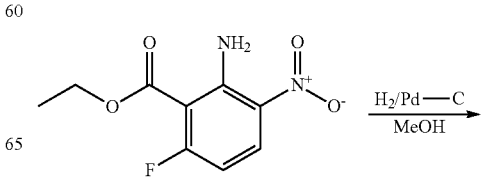

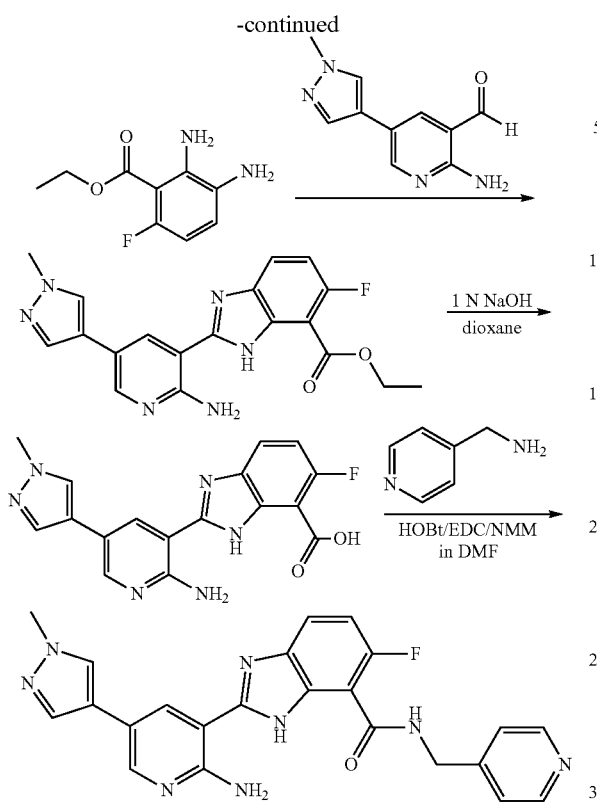

18.1 Ethyl 2-amino-6-fluoro-3-nitrobenzoate is hydrogenated under standard conditions to give ethyl 2,3-diamino-6-fluorobenzoate; HPLC-MS [M+H]$^+$ 199.2.

18.2 The cyclisation to the benzimidazole is carried out in accordance with method 1 route A, giving ethyl 2-[2-amino-5-(1-methyl-1H-pyrazol-4-yl)pyridin-3-yl]-5-fluoro-3H-benzimidazole-4-carboxylate ("A141"); HPLC-MS [M+H]$^+$ 381.2;

$^1$H NMR (500 MHz, DMSO-d$_6$+TFA-d$_1$) δ [ppm] 9.17 (d, J=2.0, 1H), 8.36 (d, J=2.0, 1H), 8.18 (s, 1H), 7.98 (s, 1H), 7.94 (dd, J=8.9, 4.3, 1H), 7.24 (dd, J=11.3, 8.9, 1H), 4.45 (q, J=7.1, 2H), 3.90 (s, 3H), 1.37 (t, J=7.1, 3H).

18.3 700 mg (1.840 mmol) of "A141" is dissolved in dioxane, and 7 ml (7 mmol) of 1N NaOH is added. The reaction mixture is stirred at 60° C. for 20 hours. The solid formed is filtered off with suction, washed with water and acetone and purified further by means of RP-HPLC, giving 2-[2-amino-5-(1-methyl-1H-pyrazol-4-yl)pyridin-3-yl]-5-fluoro-3H-benzimidazole-4-carboxylic acid ("A142"); HPLC-MS [M+H]$^+$ 353.2;

$^1$H NMR (500 MHz, DMSO-d$_6$+TFA-d$_1$) δ [ppm] 9.26 (d, J=2.0, 1H), 8.43 (d, J=2.0, 1H), 8.26 (s, 1H), 8.04 (s, 1H), 8.00 (dd, J=8.8, 4.3, 1H), 7.30 (dd, J=11.3, 8.9, 1H), 3.95 (s, 3H).

18.4 35 mg (0.099 mmol) of "A142" are dissolved in 3 ml of DMF. 11.05 μl (0.109 mmol) of 4-picolylamine, 14.8 mg (0.109 mmol) of HOBt, 20.9 mg (0.109 mmol) of EDC and 12 μl (0.109 mmol) of N-methylmorpholine are added. The reaction mixture is stirred at room temperature for 6 hours, and saturated NaHCO$_3$ solution is added. The precipitate formed is washed with water and dried, giving N-(pyridin-4-ylmethyl)-2-[2-amino-5-(1-methyl-1H-pyrazol-4-yl)pyridin-3-yl]-5-fluoro-3H-benzimidazole-4-carboxamide; HPLC-MS [M+H]$^+$ 443.2;

$^1$H NMR (500 MHz, DMSO-d$_6$+TFA-d$_1$) δ [ppm] 9.21 (d, J=2.0, 1H), 9.01-8.94 (m, 2H), 8.46 (d, J=2.1, 1H), 8.24 (s, 1H), 8.14 (d, J=6.1, 2H), 8.03 (s, 1H), 7.94 (dd, J=8.8, 4.5, 1H), 7.36 (dd, J=11.0, 8.9, 1H), 4.95 (s, 2H), 3.95 (s, 3H).

EXAMPLE 19

Preparation of 1-{2-[2-amino-5-(1-methyl-1H-pyrazol-4-yl)pyridin-3-yl]-1H-benzimidazol-5-yl}-1-phenylethanol ("A143")

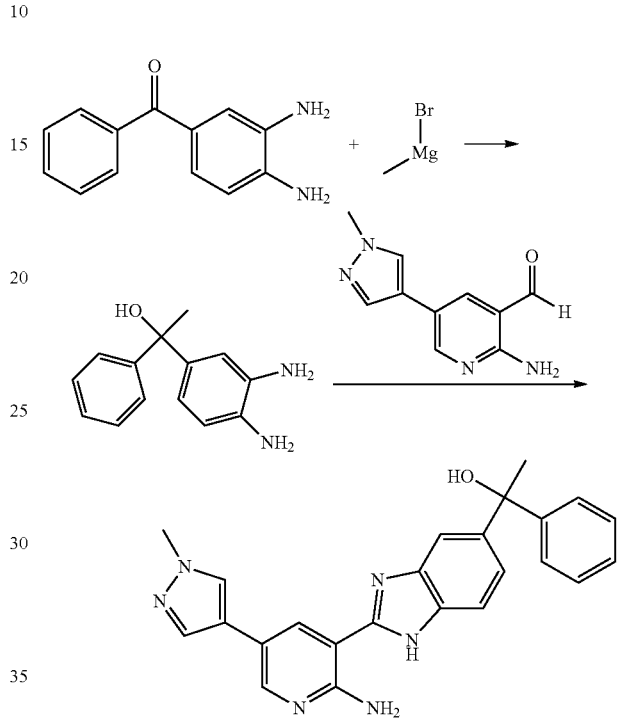

15 ml (45 mmol) of methylmagnesium bromide solution (3M in diethyl ether) is diluted with 13 ml of diethyl ether. A solution of 2 g (9.423 mmol) of 3,4-diaminophenone in 13 ml of diethyl ether is added dropwise to the Grignard solution at 0° C. The reaction mixture is quenched at 0° C. using 15 ml of saturated NaCl solution, and diethyl ether is added. The organic phase is separated off, and the aqueous phase is extracted 2× with ethyl acetate. The combined organic phases are dried over sodium sulfate, filtered, and the solvent is removed. The residue is chromatographed, giving 1-(3,4-diaminophenyl)-1-phenylethanol; HPLC-MS [M+H]$^+$ 229.2.

The cyclisation to the benzimidazole is carried out in accordance with method 1 route A, giving 1-{2-[2-amino-5-(1-methyl-1H-pyrazol-4-yl)pyridin-3-yl]-1H-benzimidazol-5-yl}-1-phenylethanol; HPLC-MS [M+H]$^+$ 411.2;

$^1$H NMR (500 MHz, DMSO-d$_6$+TFA-d$_1$) δ [ppm] 8.98 (d, J=2.1, 1H), 8.43 (d, J=2.1, 1H), 8.20 (s, 1H), 7.98 (s, 1H), 7.82 (d, J=1.2, 1H), 7.67 (d, J=8.6, 1H), 7.52 (dd, J=8.3, 1.1, 2H), 7.46 (dd, J=8.6, 1.5, 1 H), 7.32 (t, J=7.7, 2H), 7.21 (t, J=7.3, 1H), 3.95 (s, 3H), 1.97 (s, 3H).

EXAMPLE 20

Preparation of 3-(6-methoxy-1H-benzimidazol-2-yl)-5-thiophen-3-ylpyridin-2-ylamine ("A144")

Alternatively to the standard conditions of Suzuki coupling in method 1 route A, the Suzuki coupling can also be carried out using trifluoroborate starting materials.

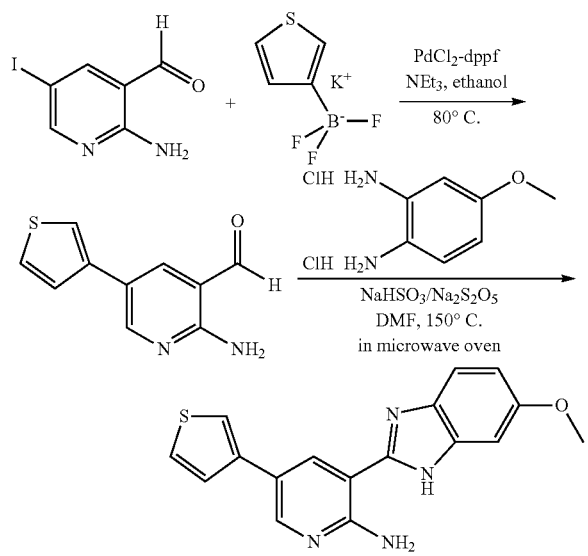

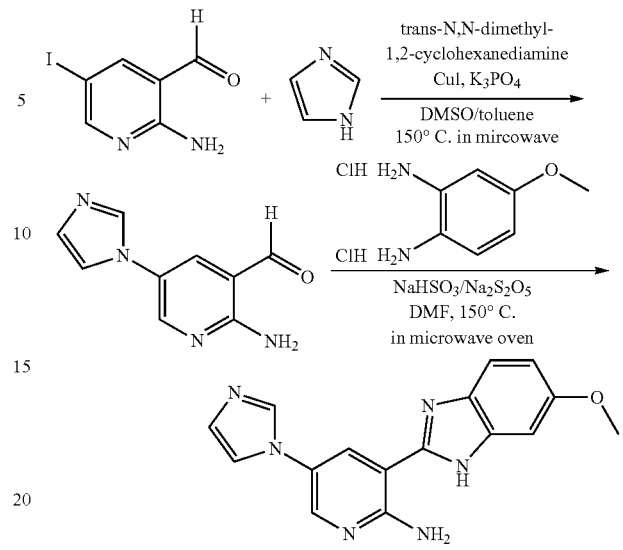

20.1 Suzuki Coupling:

150 mg (0.605 mmol) of 2-amino-5-iodopyridine-3-carbaldehyde and 115 mg (0.605 mmol) of potassium 3-thiophenetrifluoroborate are suspended in 4 ml of ethanol in a nitrogen-filled reaction vessel, and 251 μl (1.814 mmol) of triethylamine and 22.1 mg (0.030 mmol) of [1,1'-bis(diphenylphosphino)ferrocene]palladium(II) dichloride are added. The reaction mixture is stirred at 80° C. for 14 h under a nitrogen protective atmosphere. The reaction mixture is cooled to room temperature and diluted with water/ethyl acetate and filtered off. The organic phase is separated, and the aqueous phase is extracted a further 2× with ethyl acetate. The combined organic phases are dried over sodium sulfate, filtered, and the solvent is removed, giving 2-amino-5-thiophen-3-ylpyridine-3-carbaldehyde; HPLC-MS [M+H]$^+$ 205.2.

20.2 Cyclisation to the Benzimidazole:

147.9 μl (0.750 mmol) of 38-40% sodium hydrogensulfite solution are added to a solution of 81.1 mg (0.250 mmol) of 2-amino-5-thiophen-3-ylpyridine-3-carbaldehyde and 64.6 mg (0.300 mmol) of 4-methoxy-o-phenylenediamine dihydrochloride in 1.5 ml of DMF, and the mixture is irradiated with microwaves for 30 min at 150° C. in the Biotage Smith-Synthesizer. The reaction mixture is cooled to room temperature, water is added, and the mixture is extracted 3× with ethyl acetate. The combined organic phases are dried over sodium sulfate, filtered, and the solvent is removed. The residue is purified by means of RP-HPLC: 3-(6-methoxy-1H-benzimidazol-2-yl)-5-thiophen-3-ylpyridin-2-ylamine hydrochloride; HPLC-MS [M+H]$^+$ 323.2;

$^1$H NMR (500 MHz, DMSO-d$_6$+TFA-d$_1$) δ [ppm] 9.09 (d, J=2.0, 1H), 8.54 (d, J=2.0, 1H), 7.99 (d, J=1.6, 1H), 7.73 (dd, J=5.0, 3.0, 1H), 7.65 (dd, J=9.8, 4.8, 2H), 7.19 (d, J=2.2, 1H), 7.00 (dd, J=8.8, 2.3, 1H), 3.84 (s, 3H).

EXAMPLE 21

Preparation of 5-imidazol-1-yl-3-(5-methoxy-1H-benzimidazol-2-yl)pyridin-2-ylamine ("A145")

Alternatively to the standard conditions of the Suzuki coupling in method 1 route A, the synthesis sequence can also be started with a copper-catalysed coupling.

300 mg (1.210 mmol) of 2-amino-5-iodopyridine-3-carbaldehyde and 24 mg (3.629 mmol) of imidazole are dissolved in ml of DMSO in a nitrogen-filled microwave vessel. 51.6 mg (0.363 mmol) of trans-N,N-dimethyl-1,2-cyclohexanediamine, 69.1 mg (0.363 mmol) of copper iodide, 523.8 mg (2.468 mmol) of K$_3$PO$_4$ and 5 ml of toluene is added. The reaction mixture is irradiated with microwaves for 2 hours at 150° C. The reaction mixture is cooled to room temperature, filtered off, and the solvent is removed. Water/ethyl acetate is added to the residue. The organic phase is separated, and the aqueous phase is extracted a further 2× with ethyl acetate. The combined organic phases are dried over sodium sulfate, filtered, and the solvent is removed, giving 2-amino-5-imidazol-1-ylpyridine-3-carbaldehyde; HPLC-MS [M+H]$^+$ 189.2.

The cyclisation to the benzimidazole is carried out analogously to Example 20, giving 5-imidazol-1-yl-3-(5-methoxy-1H-benzimidazol-2-yl)pyridin-2-ylamine; HPLC-MS [M+H]$^+$ 307.2;

$^1$H NMR (500 MHz, DMSO-d$_6$+TFA-d$_1$) δ [ppm] 9.61 (t, J=1.4, 1H), 8.66 (dd, J=7.9, 2.6, 2H), 8.15 (t, J=1.7, 1 H), 7.98-7.93 (m, 1H), 7.68 (d, J=8.9, 1H), 7.22 (d, J=2.3, 1H), 7.06 (dd, J=8.9, 2.4, 1 H), 3.86 (s, 3H).

EXAMPLE 22

Preparation of 4-{2-[2-amino-5-(1-methyl-1H-pyrazol-4-yl)pyridin-3-yl]-3H-benzimidazol-5-yl}morpholin-3-one ("A146")

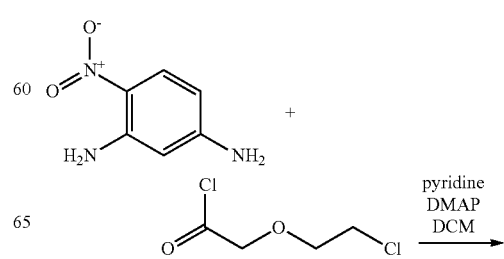

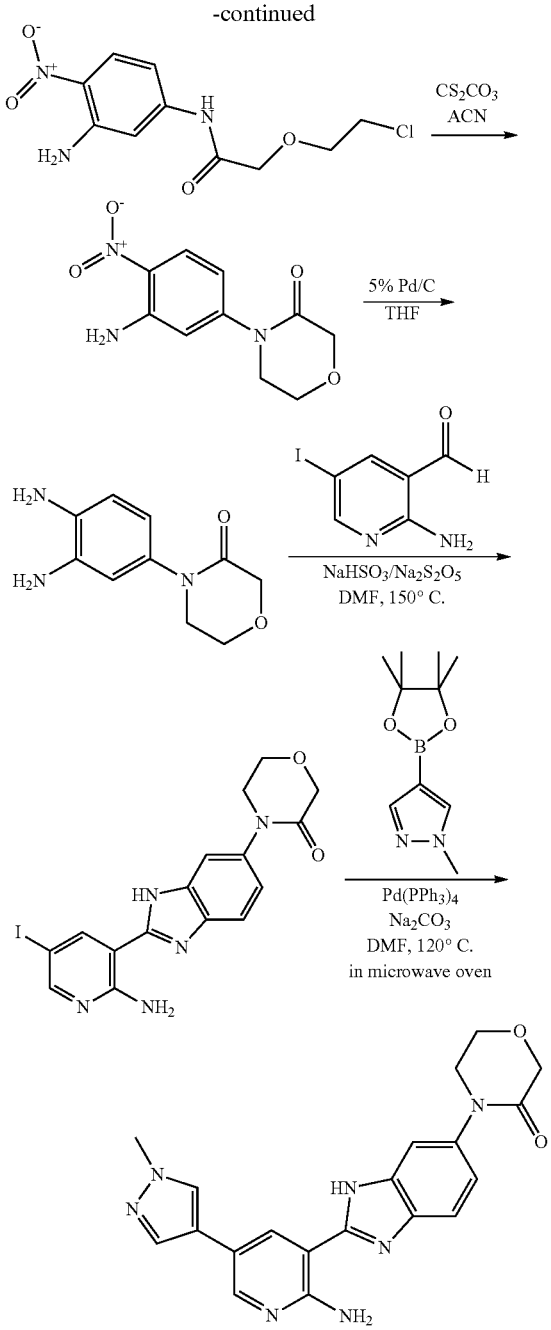

22.1 7.963 g (0.052 mol) of 1,3-diamino-4-nitrophenyl are suspended in 250 ml of DCM, and 8.394 ml (0.104 mol) of pyridine and 1.271 g (0.01 mol) of DMAP are added at room temperature under nitrogen. 16.4 g (0.104 mol) of (2-chloroethoxy)acetyl chloride are subsequently slowly added dropwise to the yellow suspension. Since the reaction is exothermic, the temperature is held at 20° C. by cooling with an ice/water bath. The mixture is stirred at room temperature for 18 h. The batch is diluted with about 500 ml of dichloromethane, and 750 ml of water are subsequently added. The organic phase is separated off, and the aqueous phase is extracted a further 2× with 500 ml of ethyl acetate each time. The entire organic phases are dried using anhydrous sodium sulfate, filtered, and the solvent is stripped off in a Rotavapor to about 200 ml. The crystals formed during evaporation in the rotary evaporator are separated off and dried, giving N-(3-amino-4-nitrophenyl)-2-(2-chloroethoxy)acetamide, HPLC-MS [M+H]$^+$ 274.1.

22.2 5.2 g (0.016 mol) of N-(3-amino-4-nitrophenyl)-2-(2-chloroethoxy)acetamide are suspended in 250 ml of acetonitrile, and 6.6 g (0.02 mol) of caesium carbonate are added. The mixture is stirred at room temperature for 18 h. The batch is poured into about 250 ml of water and extracted 3× with 200 ml of ethyl acetate each time. The entire organic phases are dried using anhydrous sodium sulfate, filtered, and the solvent is stripped off in a Rotavapor to a residual volume of about 150 ml. The crystals deposited during evaporation in the rotary evaporator are separated off and dried, giving 4-(3-amino-4-nitrophenyl)morpholin-3-one, HPLC-MS [M+H]$^+$ 238.1.

22.3 4-(3-Amino-4-nitrophenyl)morpholin-3-one is hydrogenated under standard conditions, giving 4-(3,4-diaminophenyl)morpholin-3-one; HPLC-MS [M+H]$^+$ 208.1.

22.4 320 mg (1.544 mmol) of 4-(3,4-diaminophenyl)morpholin-3-one are dissolved in 4 ml of DMF, and 382.99 mg (1.544 mmol) of 2-amino-5-iodopyridine-3-carbaldehyde and 0.913 ml (4.633 mmol) of 38-40% sodium hydrogensulfite solution are added at room temperature. The mixture is stirred at 150° C. for 18 hours. The batch is cooled to room temperature, poured into 20 ml of water, the precipitate which deposits in the process is separated off and washed well with about 10 ml of water. The precipitate is triturated with about 25 ml of acetonitrile, and the undissolved crystals are separated off and dried, giving 4-[2-(2-amino-5-iodopyridin-3-yl)-3H-benzimidazol-5-yl]morpholin-3-one; HPLC-MS [M+H]$^+$ 436.0.

22.5 The Suzuki coupling is carried out analogously to route 1 method B, giving 4-{2-[2-amino-5-(1-methyl-1H-pyrazol-4-yl)pyridin-3-yl]-3H-benzimidazol-5-yl}morpholin-3-one; HPLC-MS [M+H]$^+$ 390.2;

$^1$H NMR (500 MHz, DMSO-d$_6$+TFA-d$_1$) δ [ppm] 9.05 (d, J=2.1, 1H), 8.40 (d, J=2.1, 1H), 8.19 (s, 1H), 7.97 (s, 1H), 7.75 (dd, J=5.2, 3.2, 2H), 7.35 (dd, J=8.7, 1.9, 1 H), 4.24 (s, 2H), 4.04-3.99 (m, 2H), 3.92 (s, 3H), 3.84-3.78 (m, 2H).

EXAMPLE 23

Preparation of 3-{2-[2-amino-5-(1-methyl-1H-pyrazol-4-yl)pyridin-3-yl]-1H-benzimidazol-5-yl}-1,3-oxazinan-2-one ("A147")

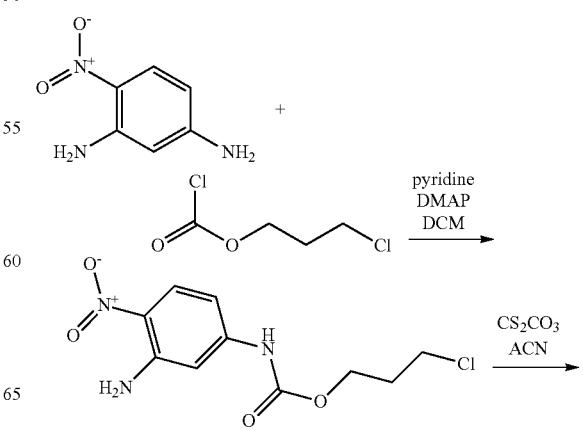

-continued

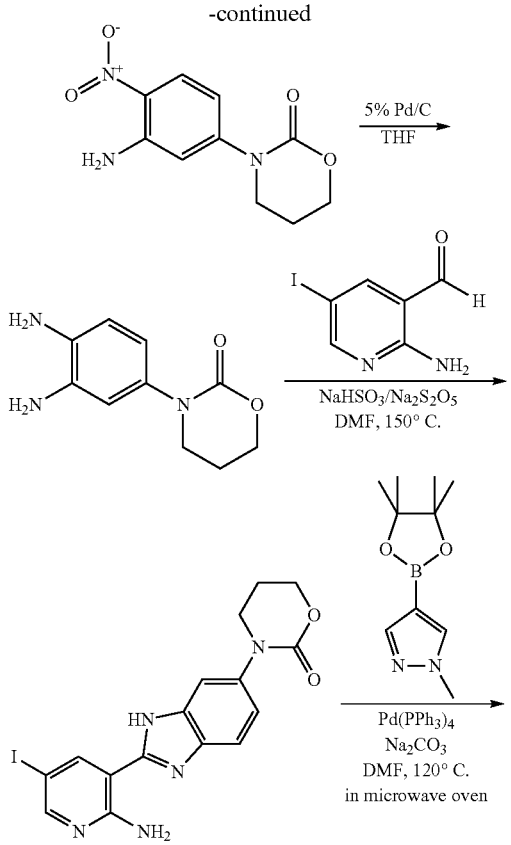

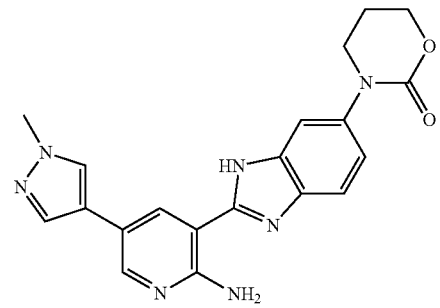

The synthesis sequence is carried out analogously to Example 22, giving 3-{2-[2-amino-5-(1-methyl-1H-pyrazol-4-yl)pyridin-3-yl]-1H-benzimidazol-5-yl}-1,3-oxazinan-2-one; HPLC-MS [M+H]+ 390.2;

$^1$H NMR (500 MHz, DMSO-d$_6$+TFA-d$_1$) δ [ppm] 9.02 (d, J=2.0, 1H), 8.39 (d, J=2.0, 1H), 8.17 (s, 1H), 7.96 (s, 1H), 7.72 (d, J=6.2, 1H), 7.71 (s, 1H), 7.33 (dd, J=8.8, 1.8, 1 H), 4.40-4.34 (m, 2H), 3.91 (s, 3H), 3.72 (t, J=6.0, 2H), 2.18-2.11 (m, 2H).

EXAMPLE 24

The following compounds are obtained analogously to method 1 route A

| No. | Name and/or structure | Analysis |
|---|---|---|
| "A148" | 3-(5-Fluoro-6-methoxy-1H-benzimidazol-2-yl)-5-[1-(2-morpholin-4-ylethyl)-1H-pyrazol-4-yl]pyridin-2-ylamine | MW 437.48 HPLC-MS [M + H]+ 438.2 |

$^1$H NMR (500 MHz, DMSO-d$_6$ + TFA-d$_1$) δ 9.07 (d, J = 2.0, 1H), 8.43 (d, J = 2.0, 1H), 8.38 (s, 1H), 8.14 (s, 1H), 7.62 (d, J = 11.0, 1H), 7.41 (d, J = 7.7, 1H), 4.68 (t, J = 6.5, 2H), 4.08-3.98 (m, 2H), 3.96 (s, 3H), 3.74 (t, J = 6.5, 4H), 3.58-3.45 (m, 2H), 3.30-3.14 (m, 2H)

| | | |
|---|---|---|
| "A149" | 1-{2-[2-Amino-5-(1-piperidin-4-yl-1H-pyrazol-4-yl)-pyridin-3-yl]-1H-benzimidazol-5-yl}-1-phenylethanol | |

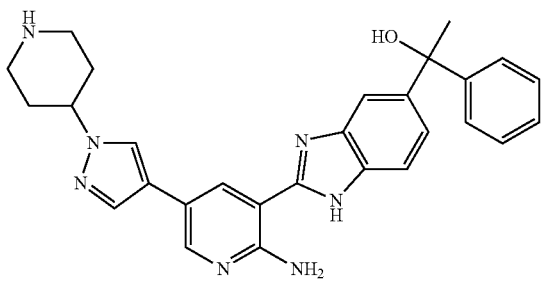 [SMILES: CC(O)(c1ccccc1)c1ccc2[nH]c(-c3cc(-c4cnn(C5CCNCC5)c4)cnc3N)nc2c1]

-continued

| No. | Name and/or structure | Analysis |
|---|---|---|
| "A150" | 1-(2-{2-Amino-5-[1-(2-morpholin-4-ylethyl)-1H-pyrazol-4-yl]pyridin-3-yl}-1H-benzimidazol-5-yl)-1-phenylethanol, formate | MW 509.61 HPLC-MS [M + H]+ 510.2 |

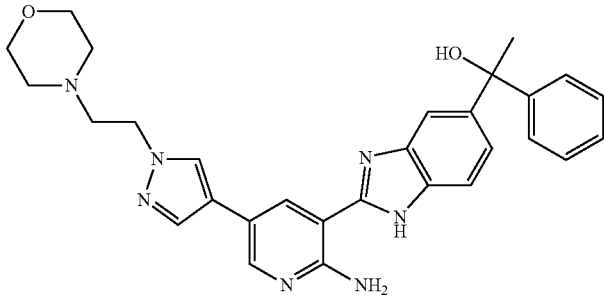 [SMILES: CC(O)(c1ccccc1)c1ccc2[nH]c(-c3cc(-c4cnn(CCN5CCOCC5)c4)cnc3N)nc2c1]

$^1$H NMR (400 MHz, DMSO-d$_6$ + TFA-d$_1$) δ [ppm] 8.98 (d, J = 2.1, 1H), 8.43 (d, J = 2.1, 1H), 8.20 (s, 1H), 7.98 (s, 1H), 7.82 (d, J = 1.2, 1H), 7.67 (d, J = 8.6, 1H), 7.52 (dd, J = 8.3, 1.1, 2H), 7.46 (dd, J = 8.6, 1.5, 2H), 7.32 (t, J = 7.7, 2H), 7.21 (t, J = 7.3, 1H), 4.68 (t, J = 6.5, 2H), 4.08-3.98 (m, 2H), 3.74 (t, J = 6.5, 4H), 3.58-3.45 (m, 2H), 3.30-3.14 (m, 2H), 1.97 (s, 3H)

Inhibition of PDK1
IC$_{50}$ of compounds according to the invention

| Compound No. | IC$_{50}$ PDK1 (enzyme) | IC$_{50}$ PDK1 (cell) | IC$_{50}$ IRAK-1 (enzyme) | IC$_{50}$ IRAK-4 (enzyme) | IC$_{50}$ IRAK-4 (cell) |
|---|---|---|---|---|---|
| "A1" | A | B | B | C | |
| "A2" | A | B | | | |
| "A3" | A | C | | | |
| "A4" | A | B | | | |
| "A8" | | | B | B | |
| "A9" | A | B | | | |
| "A11" | A | B | | | |
| "A12" | A | B | | | |
| "A13" | A | B | | | |
| "A15" | A | C | | | |
| "A16" | A | C | | | |
| "A17" | A | | | | |
| "A24" | A | | | | |
| "A25" | A | | | | |
| "A26" | A | | | | |
| "A29" | A | C | | | |
| "A30" | | | A | B | |
| "A32" | | | B | B | |
| "A34" | | | B | B | |
| "A35" | | | B | B | |
| "A42" | | | B | B | |
| "A43" | A | C | B | B | |
| "A44" | | | B | B | B |
| "A48" | | | B | B | |
| "A50" | | | B | A | |
| "A52" | A | B | B | B | |
| "A53" | A | B | | | |
| "A55" | A | | | | |
| "A62" | | | B | B | |
| "A64" | A | | | | |
| "A66" | | | B | B | |
| "A67" | A | B | | | |
| "A68" | A | C | | | |
| "A69" | A | | A | A | |
| "A70" | | | B | A | |
| "A72" | | | B | B | |
| "A74" | A | | B | B | |
| "A76" | | | B | C | |
| "A78" | | | A | B | |
| "A80" | A | C | | | |

| Compound No. | IC$_{50}$ PDK1 (enzyme) | IC$_{50}$ PDK1 (cell) | IC$_{50}$ IRAK-1 (enzyme) | IC$_{50}$ IRAK-4 (enzyme) | IC$_{50}$ IRAK-4 (cell) |
|---|---|---|---|---|---|
| "A89" | A | | B | B | |
| "A92" | A | C | A | A | B |
| "A94" | | | B | B | |
| "A96" | | | B | B | |
| "A102" | A | B | | | |
| "A105" | | | B | B | |
| "A106" | A | C | | | |
| "A107" | | | A | A | B |
| "A113" | | | A | B | |
| "A114" | | | B | A | |
| "A115" | | | B | B | |
| "A120" | A | | | | |
| "A128" | A | C | B | B | |
| "A130" | | | A | A | |
| "A133" | A | C | A | A | |
| "A144" | A | C | B | B | |
| "A148" | B | | B | A | |
| "A150" | B | | | | |

IC$_{50}$:
1 nM-0.1 μM = A
0.1 μM-10 μM = B
>10 μM = C

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains mg of active ingredient.

The invention claimed is:
1. Compounds of the formula I

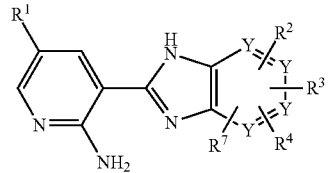

in which
$R^1$ denotes a mono- or bicyclic saturated, unsaturated or aromatic heterocycle having 1 to 4 N, O and/or S atoms, which may be unsubstituted or mono- or disubstituted by Hal, A, $OR^5$, $SR^5$, $NO_2$, CN, $NR^5COA$, $NR^5SO_2A$, $SO_2N(R^5)_2$, $S(O)_mA$, $[C(R^5)_2]_nCOOR^5$, $[C(R^5)_2]_nCON(R^5)_2$, $[C(R^5)_2]_nCONR^5[C(R^5)_2]_nAr$, $[C(R^5)_2]_nCONR^5[C(R^5)_2]_nHet$, $[C(R^5)_2]_nCO$-Het, $[C(R^5)_2]_nN(R^5)_2$, $[C(R^5)_2]_nAr$, $[C(R^5)_2]_nHet$, $O[C(R^5)_2]_nN(R^5)_2$, $O[C(R^5)_2]_nHet$, $NR^5COOA$, $NR^5CON(R^5)_2$, $NR^5COO[C(R^5)_2]_nN(R^5)_2$, $NR^5COO[C(R^5)_2]_nHet^1$, $NR^5CONR^5[C(R^5)_2]_nN(R^5)_2$, $NR^5CONR^5[C(R^5)_2]_1Het^1$, $OCONR^5[C(R^5)_2]_nN(R^5)_2$, $OCONR^5[C(R^5)_2]_nHet^1$, $[C(R^5)_2]_nR^5$, $[C(R^5)_2]_nCONR^5[C(R^5)_2]_n$—$N(R^5)_2$, CHO, COA, =S, =NH, =NA and/or =O (carbonyl oxygen),
Y, independently of one another, denotes N or C, where a maximum of two Y may denote N,
$R^2$, $R^3$, $R^4$, $R^7$ each, independently of one another, denote H, Hal, A, OA, $SR^5$, $NO_2$, CN, $NR^5COA$, $NR^5SO_2A$, $SO_2N(R^5)_2$, $S(O)_mA$, $S(O)_mHet$, CO—Ar, CO-Het, $[C(R^5)_2]_nAr$, $[C(R^5)_2]_nHet$, $C(R^5)(OR^5)Ar$, $C(R^5)(OR^5)Het$, $[C(R^5)_2]_nOR^5$, $[C(R^5)_2]_nOAr$, $[C(R^5)_2]_nOHet$, $[C(R^5)_2]_nN(R^5)_2$, $[C(R^5)_2]_nCON(R^5)_2$, $[C(R^5)_2]_nCOOR^5$, $[C(R^5)_2]_nCONR^5[C(R^5)_2]_nAr$, $[C(R^5)_2]CONR^5[C(R^5)_2]_nHet$, $[C(R^5)_2]_nCOO[C(R^5)_2]_nAr$, $[C(R^5)_2]_1COO[C(R^5)_2]_nHet$, $[C(R^5)_2]_nNR^5CO[C(R^5)_2]_nAr$ or $[C(R^5)_2]_nNR^5CO[C(R^5)_2]_nHet$,
or two adjacent radicals selected from the group $R^2$, $R^3$, $R^4$, $R^7$ together may denote $OCH_2O$, $OCH_2CH_2O$, NHCONH, $OCF_2O$, CH=N—NH or NH—N=CH,
with the proviso that
a) if one Y denotes N, $R^7$ is absent;
b) if two Y denote N, $R^4$ and $R^7$ are absent;
$R^5$ denotes A or H,
A denotes unbranched or branched alkyl having 1-10 C atoms, in which 1-7 H atoms may be replaced by F and/or in which one or two $CH_2$ groups may be replaced by O, S, $NR^5$ and/or by CH=CH groups, or cyclic alkyl having 3-7 C atoms,
Ar denotes phenyl, naphthyl or biphenyl, each of which is unsubstituted or mono-, di- or trisubstituted by Hal, A, $OR^5$, $N(R^5)_2$, $SR^5$, $NO_2$, CN, $COOR^5$, $CON(R^5)_2$, $NR^5COA$, $NR^5SO_2A$, $SO_2N(R^5)_2$, $S(O)_mA$, CO-$Het^1$, $Het^1$, $O[C(R^5)_2]_nN(R^5)_2$, $O[C(R^5)_2]_nHet^1$, NHCOOA, $NHCON(R^5)_2$, $NHCOO[C(R^5)_2]_nN(R^5)_2$, $NHCOO[C(R^5)_2]_nHet^1$, $NHCONH[C(R^5)_2]_nN(R^5)_2$, $NHCONH[C(R^5)_2]_nHet^1$, $OCONH[C(R^5)_2]_n$—$N(R^5)_2$, $OCONH[C(R^5)_2]_nHet^1$ and/or COA,
Het denotes a mono- or bicyclic saturated, unsaturated or aromatic heterocycle having 1 to 4 N, O and/or S atoms, which may be unsubstituted or mono- to trisubstituted by Hal, A, $OR^5$, $N(R^5)_2$, $SR^5$, $NO_2$, CN, $COOR^5$, $CON(R^5)_2$, $NR^5COA$, $NR^5SO_2A$, $SO_2N(R^5)_2$, $S(O)_mA$, CO-$Het^1$, $Het^1$, $[C(R^5)_2]_nN(R^5)_2$, $[C(R^5)_2]_nHet^1$, O[C

121

(R⁵)₂]ₙ—N(R⁵)₂, O[C(R⁵)₂]ₙHet¹, NHCOOA, NHCON(R⁵)₂, NHCOO[C(R⁵)₂]ₙN(R⁵)₂, NHCOO[C(R⁵)₂]ₙHet¹, NHCONH[C(R⁵)₂]ₙ—N(R⁵)₂, NHCONH[C(R⁵)₂]ₙHet¹, OCONH[C(R⁵)₂]ₙN(R⁵)₂, OCONH[C(R⁵)₂]-Het¹, CO-Het¹, CHO, COA, =S, =NH, =NA and/or =O (carbonyl oxygen), Het¹ denotes a monocyclic saturated heterocycle having 1 to 2 N and/or O atoms, which may be mono- or disubstituted by A, OA, OH, Hal and/or =O (carbonyl oxygen), Hal denotes F, Cl, Br or I, m denotes 0, 1 or 2, and n denotes 0, 1, 2, 3 or 4, and pharmaceutically usable salts, tautomers and stereoisomers thereof, including mixtures thereof in all ratios.

2. Compounds according to claim 1 in which

R¹ denotes a mono- or bicyclic saturated, unsaturated or aromatic heterocycle having 1 to 4 N, O and/or S atoms, which may be unsubstituted or mono- or disubstituted by Hal, A, OR⁵, CN, [C(R⁵)₂]ₙCOOR⁵, [C(R⁵)₂]ₙCON(R⁵)₂, [C(R⁵)₂]ₙCONR⁵[C(R⁵)₂]ₙAr, [C(R⁵)₂]ₙCONR⁵[C(R⁵)₂]ₙHet, [C(R⁵)₂]ₙCO-Het, [C(R⁵)₂]ₙN(R⁵)₂, [C(R⁵)₂]ₙAr, [C(R⁵)₂]ₙHet, [C(R⁵)₂]ₙOR⁵ and/or [C(R⁵)₂]ₙCONR⁵[C(R⁵)₂]ₙN(R⁵)₂, and pharmaceutically usable salts, tautomers and stereoisomers thereof, including mixtures thereof in all ratios.

3. Compounds according to claim 1 in which

R¹ denotes pyrazolyl, thiazolyl, thienyl, pyridyl, benzofuranyl, isoxazolyl, benzothienyl, 3,4-dihydro-2H-pyrido[3,2-b]-1,4-oxazinyl, pyrrolyl, pyrimidinyl, furanyl, imidazolyl, oxazolyl, triazolyl, tetrazolyl, thiadiazole, pyridazinyl, pyrazinyl, indolyl, isoindolyl, benzimidazolyl, indazolyl, quinolyl or 1,3-benzo-dioxolyl, each of which is unsubstituted or mono- or disubstituted by A, CH₂COHet, (CH₂)ₙOH, (CH₂)ₙHet, CONH(CH₂)ₙHet, (CH₂)ₙNH₂, OA, Hal, (CH₂)ₙNHA, (CH₂)ₙNA₂, CH₂Ar, CH₂CONA₂, (CH₂)ₙOA, (CH₂)ₙCOOH, (CH₂)ₙCOOA, CONH(CH₂)₂NA₂, CONH₂, CONHA, CONA₂, CONH(CH₂)₂OA and/or CN, and pharmaceutically usable salts, tautomers and stereoisomers thereof, including mixtures thereof in all ratios.

4. Compounds according to claim 1 in which

R², R³, R⁴, R⁷ each, independently of one another, denote H, Hal, A, OA, SO₂N(R⁵)₂, S(O)ₘHet, CO—Ar, [C(R⁵)₂]ₙAr, [C(R⁵)₂]ₙHet, C(R⁵)(OR⁵)Ar, [C(R⁵)₂]ₙOR⁵, [C(R⁵)₂]ₙOAr, [C(R⁵)₂]ₙN(R⁵)₂, [C(R⁵)₂]ₙCON(R⁵)₂, [C(R⁵)₂]ₙCOOR⁵, [C(R⁵)₂]ₙCONR⁵[C(R⁵)₂]ₙAr, [C(R⁵)₂]ₙCONR⁵[C(R⁵)₂]ₙHet or [C(R⁵)₂]ₙNR⁵CO[C(R⁵)₂]ₙAr with the proviso that a) if one Y denotes N, R⁷ is absent;

b) if two Y denote N, R⁴ and R⁷ are absent;

two adjacent radicals selected from the group R², R³, R⁴, R⁷ together also denote OCH₂O, OCH₂CH₂O, NHCONH, OCF₂O, CH=N—NH or NH—N=CH, and pharmaceutically usable salts, tautomers and stereoisomers thereof, including mixtures thereof in all ratios.

5. Compounds according to claim 1 in which

R², R³, R⁴, R⁷ each, independently of one another, denote H, (CH₂)ₙOH, (CH₂)ₙOA, (CH₂)ₙHet, Hal, A, SO₂NH₂, SO₂NHA, SO₂NA₂, (CH₂)ₙAr, CH(OH)Ar, (CH₂)ₙNHCO(CH₂)ₙAr, COAr, (CH₂)ₙCONH(CH₂)ₙAr, (CH₂)ₙCONH(CH₂)ₙHet, (CH₂)ₙCOOH, (CH₂)ₙCOOA, (CH₂)ₙCONH₂, (CH₂)ₙCONHA, (CH₂)ₙCONA₂, SO₂Het, (CH₂)ₙNH₂, (CH₂)ₙNHA, (CH₂)ₙNA₂, (CH₂)ₙOAr or CONH(CH₂)₂OA, or two adjacent radicals selected from the group R², R³, R⁴, R⁷ together may denote OCH₂O, OCH₂CH₂O, NHCONH, OCF₂O, CH=N—NH or NH—N=CH, with the proviso that a) if one Y denotes N, R⁷ is absent;

b) if two Y denote N, R⁴ and R⁷ are absent;

and pharmaceutically usable salts, tautomers and stereoisomers thereof, including mixtures thereof in all ratios.

6. Compounds according to claim 1 in which

A denotes unbranched or branched alkyl having 1-10 C atoms, in which 1-5 H atoms may be replaced by F and/or in which one CH₂ group may be replaced by 0, and pharmaceutically usable salts, tautomers and stereoisomers thereof, including mixtures thereof in all ratios.

7. Compounds according to claim 1 in which

Ar denotes phenyl which is unsubstituted or mono-, di- or trisubstituted by Hal and/or NR⁵COA, and pharmaceutically usable salts, tautomers and stereoisomers thereof, including mixtures thereof in all ratios.

8. Compounds according to claim 1 in which

Het denotes a mono- or bicyclic saturated, unsaturated or aromatic heterocycle having 1 to 4 N, O and/or S atoms, which may be unsubstituted or mono- to trisubstituted by A, COOR⁵ and/or =O (carbonyl oxygen), and pharmaceutically usable salts, tautomers and stereoisomers thereof, including mixtures thereof in all ratios.

9. Compounds according to claim 1 in which

Het denotes piperidinyl, 4,5-dihydropyridazinyl, pyridyl, mor-pholinyl, piperazinyl, pyrrolidinyl, tetrahydrofuranyl, 1,3-oxazinanyl, thienyl, pyrazolyl, thiazolyl, benzofuranyl, isoxazolyl, benzothienyl, 3,4-dihydro-2H-pyrido[3,2-b]-1,4-oxazinyl, pyrrolyl, pyrimidinyl, furanyl, imidazolyl, oxazolyl, triazolyl, tetrazolyl, thiadiazole, pyridazinyl, pyrazinyl, indolyl, isoindolyl, benzimidazolyl, indazolyl, quinolyl, 1,3-benzo-dioxolyl, tetrahydroimidazolyl, tetrahydropyrazolyl, oxazolidinyl or isoxazolidinyl, each of which is unsubstituted or mono- or disubstituted by A, COOR⁵ and/or =O (carbonyl oxygen), and pharmaceutically usable salts, tautomers and stereoisomers thereof, including mixtures thereof in all ratios.

10. Compounds according to claim 1 in which

Het¹ denotes pyrrolidinyl, tetrahydroimidazolyl, tetrahydropyrazolyl, piperidinyl, morpholinyl, piperazinyl, oxazolidinyl or isoxazolidinyl, each of which is unsubstituted or mono- or disubstituted by A and/or =O, and pharmaceutically usable salts, tautomers and stereoisomers thereof, including mixtures thereof in all ratios.

11. Compounds according to claim 1 in which

R¹ denotes a mono- or bicyclic saturated, unsaturated or aromatic heterocycle having 1 to 4 N, O and/or S atoms, which may be unsubstituted or mono- or disubstituted by Hal, A, OR⁵, CN, [C(R⁵)₂]ₙCOOR⁵, [C(R⁵)₂]ₙCON(R⁵)₂, [C(R⁵)₂]ₙCONR⁵[C(R⁵)₂]ₙAr, [C(R⁵)₂]ₙCONR⁵[C(R⁵)₂]ₙHet, [C(R⁵)₂]ₙCO-Het, [C(R⁵)₂]ₙN(R⁵)₂, [C(R⁵)₂]ₙAr, [C(R⁵)₂]ₙHet, [C(R⁵)₂]ₙOR⁵ and/or [C(R⁵)₂]ₙCONR⁵[C(R⁵)₂]ₙN(R⁵)₂, Y, independently of one another, denotes N or C, where a maximum of two Y may denote N, R², R³, R⁴, R⁷ each, independently of one another, denote H, Hal, A, OA, SO₂N(R⁵)₂, S(O)ₘHet, CO—Ar, [C(R⁵)₂]ₙAr, [C(R⁵)₂]ₙHet, C(R⁵)(OR⁵)Ar, [C(R⁵)₂]ₙOR⁵, [C(R⁵)₂]ₙOAr, [C(R⁵)₂]ₙN(R⁵)₂, [C(R⁵)₂]ₙCON (R⁵)₂, [C(R⁵)₂]ₙCOOR⁵, [C(R⁵)₂]ₙCONR⁵[C(R⁵)₂]ₙ Ar, [C(R⁵)₂]ₙCONR⁵[C(R⁵)₂]ₙHet or [C(R⁵)₂]ₙNR⁵CO [C(R⁵)₂]ₙAr or two adjacent radicals selected from the group R², R³, R⁴, R⁷ together may also denote OCH₂O, OCH₂CH₂O, NHCONH, OCF₂O, CH=N—NH or NH—N=CH, with the proviso that
a) if one Y denotes N, R⁷ is absent;
b) if two Y denote N, R⁴ and R⁷ are absent;

R⁵ denotes A or H,

A denotes unbranched or branched alkyl having 1-10 C atoms, in which 1-5 H atoms may be replaced by F and/or in which one
CH₂ group may be replaced by O, Ar denotes phenyl which is unsubstituted or mono-, di- or trisubstituted by Hal and/or NR⁵COA, Het denotes a mono- or bicyclic saturated, unsaturated or aromatic heterocycle having 1 to 4 N, O and/or S atoms, which may be unsubstituted or mono- to trisubstituted by A, COOR⁵ and/or =O (carbonyl oxygen), Hal denotes F, Cl, Br or I, m denotes 0, 1 or 2, n denotes 0, 1, 2, 3 or 4, and pharmaceutically usable salts, tautomers and stereoisomers thereof, including mixtures thereof in all ratios.

12. Compounds according to claim 1, selected from the group

| Compound No. | Name and/or structure |
|---|---|
| "A1" | 6-{2-[2-Amino-5-(1-methyl-1H-pyrazol-4-yl)pyridin-3-yl]-3H-benzimidazol-5-yl}-5-methyl-4,5-dihydro-2H-pyridazin-3-one |
| "A2" | (R)-6-{2-[2-Amino-5-(1-methyl-1H-pyrazol-4-yl)pyridin-3-yl]-3H-benzimidazol-5-yl}-5-methyl-4,5-dihydro-2H-pyridazin-3-one |
| "A3" | (S)-6-{2-[2-Amino-5-(1-methyl-1H-pyrazol-4-yl)pyridin-3-yl]-3H-benzimidazol-5-yl}-5-methyl-4,5-dihydro-2H-pyridazin-3-one |
| "A4" | 6-{2-[2-Amino-5-(1-methyl-1H-pyrazol-4-yl)pyridin-3-yl]-1H-benzimidazol-5-yl}-5-ethyl-4,5-dihydro-2H-pyridazin-3-one |
| "A5" | 6-{2-[2-Amino-5-(1-methyl-1H-pyrazol-4-yl)pyridin-3-yl]-3H-benzimidazol-5-yl}-5,5-dimethyl-4,5-dihydro-2H-pyridazin-3-one |
| "A6" | 6-{2-[2-Amino-5-(1-methyl-1H-pyrazol-4-yl)pyridin-3-yl]-3H-benzimidazol-5-yl}-2,5-dimethyl-4,5-dihydro-2H-pyridazin-3-one |
| "A7" | 6-{2-[2-Amino-5-(1-methyl-1H-pyrazol-4-yl)pyridin-3-yl]-3H-benzimidazol-5-yl}-4,5-dihydro-2H-pyridazin-3-one |
| "A8" | 6-{2-[2-Amino-5-(1-methyl-1H-pyrazol-4-yl)pyridin-3-yl]-3H-benzimidazol-5-yl}-2H-pyridazin-3-one |
| "A9" | 6-(2-{2-Amino-5-[1-(2-morpholin-4-ylethyl)-1H-pyrazol-4-yl]pyridin-3-yl}-1H-benzimidazol-5-yl)-5-methyl-4,5-dihydro-2H-pyridazin-3-one |
| "A10" | 6-(2-{2-Amino-5-[1-(3-fluorobenzyl)-1H-pyrazol-4-yl]pyridin-3-yl}-1H-benzimidazol-5-yl)-5-methyl-4,5-dihydro-2H-pyridazin-3-one |
| "A11" | 6-{2-[2-Amino-5-(1-isopropyl-1H-pyrazol-4-yl)pyridin-3-yl]-1H-benzimidazol-5-yl}-5-methyl-4,5-dihydro-2H-pyridazin-3-one |
| "A12" | 6-(2-{2-Amino-5-[1-(2-methoxyethyl)-1H-pyrazol-4-yl]pyridin-3-yl}-1H-benzimidazol-5-yl)-5-methyl-4,5-dihydro-2H-pyridazin-3-one |
| "A13" | 6-(2-{2-Amino-5-[1-(3-methoxypropyl)-1H-pyrazol-4-yl]pyridin-3-yl}-1H-benzimidazol-5-yl)-5-methyl-4,5-dihydro-2H-pyridazin-3-one |
| "A14" | 6-(2-{2-Amino-5-[1-(2-pyrrolidin-1-ylethyl)-1H-pyrazol-4-yl]pyridin-3-yl}-1H-benzimidazol-5-yl)-5-methyl-4,5-dihydro-2H-pyridazin-3-one |
| "A15" | 6-(2-{2-Amino-5-[1-(2-dimethylaminoethyl)-1H-pyrazol-4-yl]pyridin-3-yl}-1H-benzimidazol-5-yl)-5-methyl-4,5-dihydro-2H-pyridazin-3-one |
| "A16" | 6-(2-{2-Amino-5-[1-(1-methylpiperidin-4-yl)-1H-pyrazol-4-yl]pyridin-3-yl}-1H-benzimidazol-5-yl)-5-methyl-4,5-dihydro-2H-pyridazin-3-one |
| "A17" | 6-{2-[2-Amino-5-(1-piperidin-4-yl-1H-pyrazol-4-yl)pyridin-3-yl]-1H-benzimidazol-5-yl}-5-methyl-4,5-dihydro-2H-pyridazin-3-one |
| "A18" | 6-(2-{2-Amino-5-[1-(tetrahydrofuran-2-ylmethyl)-1H-pyrazol-4-yl]pyridin-3-yl}-1H-benzimidazol-5-yl)-5-methyl-4,5-dihydro-2H-pyridazin-3-one |
| "A19" | 6-[2-(6-Amino-6'-piperazin-1-yl-[3,3']bipyridinyl-5-yl)-1H-benzimidazol-5-yl]-5-methyl-4,5-dihydro-2H-pyridazin-3-one |
| "A20" | 6-{2-[2-Amino-5-(2-dimethylaminothiazol-4-yl)pyridin-3-yl]-1H-benzimidazol-5-yl}-5-methyl-4,5-dihydro-2H-pyridazin-3-one |
| "A21" | 6-[2-(6-Amino-6'-methoxy-[3,3']bipyridinyl-5-yl)-1H-benzimidazol-5-yl]-5-methyl-4,5-dihydro-2H-pyridazin-3-one |
| "A22" | 6-[2-(6,6'-Diamino-[3,3']bipyridinyl-5-yl)-1H-benzimidazol-5-yl]-5-methyl-4,5-dihydro-2H-pyridazin-3-one |
| "A23" | 6-{2-[2-Amino-5-(4-fluoro-2H-pyrazol-3-yl)pyridin-3-yl]-1H-benzimidazol-5-yl}-5-methyl-4,5-dihydro-2H-pyridazin-3-one |
| "A24" | (4-{6-Amino-5-[5-(4-methyl-6-oxo-1,4,5,6-tetrahydro-pyridazin-3-yl)-1H-benzimidazol-2-yl]pyridin-3-yl}pyrazol-1-yl)acetic acid |
| "A25" | 2-(4-{6-Amino-5-[5-(4-methyl-6-oxo-1,4,5,6-tetrahydropyridazin-3-yl)-1H-benzimidazol-2-yl]pyridin-3-yl}pyrazol-1-yl)-N,N-dimethylacetamide |
| "A26" | 6-[2-(2-Amino-5-{1-[2-(4-methylpiperazin-1-yl)-2-oxoethyl]-1H-pyrazol-4-yl}pyridin-3-yl)-1H-benzimidazol-5-yl]-5-methyl-4,5-dihydro-2H-pyridazin-3-one |
| "A27" | 2-{4-[6-Amino-5-(6-methoxy-1H-benzimidazol-2-yl)pyridin-3-yl]pyrazol-1-yl}-N-(3,4-difluorobenzyl)acetamide |
| "A28" | 6-(2-{2-Amino-5-[1-(2-oxo-2-piperidin-1-ylethyl)-1H-pyrazol-4-yl]pyridin-3-yl}-3H-benzimidazol-5-yl)-5-methyl-4,5-dihydro-2H-pyridazin-3-one |
| "A29" | 6-(2-{2-Amino-5-[1-(2-hydroxyethyl)-1H-pyrazol-4-yl]pyridin-3-yl}-3H-benzimidazol-5-yl)-5-methyl-4,5-dihydro-2H-pyridazin-3-one |
| "A30" | 2-{4-[6-Amino-5-(5-fluoro-6-methoxy-1H-benzimidazol-2-yl)-pyridin-3-yl]pyrazol-1-yl}-1-piperidin-1-ylethanone |
| "A31" | 3-(1H-Benzimidazol-2-yl)-5-(1-piperidin-4-yl-1H-pyrazol-4-yl)-pyridin-2-ylamine |
| "A32" | 5-(1H-Benzimidazol-2-yl)-[3,4']bipyridinyl-6-ylamine |
| "A33" | 3-(1H-Benzimidazol-2-yl)-5-furan-ylpyridin-2-ylamine |
| "A34" | 3-(1H-Benzimidazol-2-yl)-5-(1-methyl-1H-pyrazol-4-yl)-pyridin-2-ylamine |
| "A35" | 5-(1H-Benzimidazol-2-yl)-[3,3']bipyridinyl-6,6'-diamine |
| "A36" | 3-(5-Isopropyl-1H-benzimidazol-2-yl)-5-(1-methyl-1H-pyrazol-4-yl)pyridin-2-ylamine |
| "A37" | 5-(1H-Benzimidazol-2-yl)-[3,3']bipyridinyl-6-ylamine |
| "A38" | 3-(1H-Benzimidazol-2-yl)-5-furan-ylpyridin-2-ylamine |
| "A39" | 3-(1H-Benzimidazol-2-yl)-5-(1H-pyrazol-4-yl)pyridin-2-ylamine |
| "A40" | 3-(1H-Benzimidazol-2-yl)-5-[1-(2-pyrrolidin-1-ylethyl)-1H-pyrazol-4-yl]pyridin-2-ylamine |
| "A41" | 3-(1H-Benzimidazol-2-yl)-5-pyrimidin-5-ylpyridin-2-ylamine |
| "A42" | 3-(7-Methyl-1H-benzimidazol-2-yl)-5-(1-methyl-1H-pyrazol-4-yl)pyridin-2-ylamine |
| "A43" | 3-(6-Methoxy-1H-benzimidazol-2-yl)-5-(1-methyl-1H-pyrazol-4-yl)pyridin-2-ylamine |
| "A44" | 3-(1H-Benzimidazol-2-yl)-5-(1-propyl-1H-pyrazol-4-yl)-pyridin-2-ylamine |
| "A45" | 5-(1-Isobutyl-1H-pyrazol-4-yl)-3-(7-methyl-1H-benzimidazol-2-yl)pyridin-2-ylamine |
| "A46" | 3-(7-Methyl-1H-benzimidazol-2-yl)-5-[1-(3-methylbutyl)-1H-pyrazol-4-yl]pyridin-2-ylamine |
| "A47" | 5-(7-Methyl-1H-benzimidazol-2-yl)-[3,3']bipyridinyl-6-ylamine |
| "A48" | 3-(7-Methyl-1H-benzimidazol-2-yl)-5-[1-(2-morpholin-4-ylethyl)-1H-pyrazol-4-yl]pyridin-2-ylamine |
| "A49" | 3-(5H-1,3-Dioxolo[4',5':4,5]benzo[1,2-d]imidazol-6-yl)-5-(1-piperidin-4-yl-1H-pyrazol-4-yl)pyridin-2-ylamine |
| "A50" | 3-(6-Fluoro-1H-benzimidazol-2-yl)-5-(1-piperidin-4-yl-1H-pyrazol-4-yl)pyridin-2-ylamine |
| "A51" | 2-[2-Amino-5-(1-methyl-1H-pyrazol-4-yl)pyridin-3-yl]-3H-benzimidazole-5-carboxylic acid |

-continued

| Compound No. | Name and/or structure |
|---|---|
| "A52" | {2-[2-Amino-5-(1-methyl-1H-pyrazol-4-yl)pyridin-3-yl]-3H-benzimidazol-4-yl}methanol |
| "A53" | 3-(6-tert-Butyl-1H-benzimidazol-2-yl)-5-(1-piperidin-4-yl-1H-pyrazol-4-yl)pyridin-2-ylamine |
| "A54" | 3-(2,2-Difluoro-5H-1,3-dioxolo[4',5':4,5]benzo[1,2-d]imidazol-6-yl)-5-(1-piperidin-4-yl-1H-pyrazol-4-yl)pyridin-2-ylamine |
| "A55" | 6-[2-Amino-5-(1-piperidin-4-yl-1H-pyrazol-4-yl)pyridin-3-yl]-3,5-dihydro-1H-benzo[1,2-d;4,5-d']diimidazol-2-one |
| "A56" | 3-(7-Fluoro-1H-benzimidazol-2-yl)-5-(1-methyl-1H-pyrazol-4-yl)pyridin-2-ylamine |
| "A57" | 3-(5,6-Difluoro-1H-benzimidazol-2-yl)-5-(1-piperidin-4-yl-1H-pyrazol-4-yl)pyridin-2-ylamine |
| "A58" | Methyl 2-[2-amino-5-(1-methyl-1H-pyrazol-4-yl)pyridin-3-yl]-3H-benzimidazole-5-carboxylate |
| "A59" | 5-(1-Piperidin-4-yl-1H-pyrazol-4-yl)-3-(6-trifluoromethyl-1H-benzimidazol-2-yl)pyridin-2-ylamine |
| "A60" | 3-(4-Methoxy-1H-benzimidazol-2-yl)-5-(1-methyl-1H-pyrazol-4-yl)pyridin-2-ylamine |
| "A61" | 3-(6,7-Dihydro-1H-5,8-dioxa-1,3-diaza-cyclopenta[b]naphthalen-2-yl)-5-(1-piperidin-4-yl-1H-pyrazol-4-yl)pyridin-2-ylamine |
| "A62" | 2-[2-Amino-5-(1-piperidin-4-yl-1H-pyrazol-4-yl)pyridin-3-yl]-1H-benzimidazole-5-sulfonamide |
| "A63" | N-(4-{2-[2-Amino-5-(1-piperidin-4-yl-1H-pyrazol-4-yl)pyridin-3-yl]-3H-benzimidazol-5-yloxy}phenyl)acetamide |
| "A64" | 3-[6-(2-Aminoethyl)-1H-benzimidazol-2-yl]-5-(1-methyl-1H-pyrazol-4-yl)pyridin-2-ylamine |
| "A65" | Ethyl 2-[2-amino-5-(1-methyl-1H-pyrazol-4-yl)pyridin-3-yl]-3H-benzimidazole-5-carboxylate |
| "A66" | 3-(5,6-Dimethoxy-1H-benzimidazol-2-yl)-5-(1-piperidin-4-yl-1H-pyrazol-4-yl)pyridin-2-ylamine |
| "A67" | 5-(1-Piperidin-4-yl-1H-pyrazol-4-yl)-3-(5-trifluoromethoxy-1H-benzimidazol-2-yl)pyridin-2-ylamine |
| "A68" | {2-[2-Amino-5-(1-methyl-1H-pyrazol-4-yl)pyridin-3-yl]-3H-benzimidazol-5-yl}dimethylamine |
| "A69" | 3-(5-Fluoro-6-methoxy-1H-benzimidazol-2-yl)-5-(1-piperidin-4-yl-1H-pyrazol-4-yl)pyridin-2-ylamine |
| "A70" | 3-(6-Chloro-1H-benzimidazol-2-yl)-5-(1-piperidin-4-yl-1H-pyrazol-4-yl)pyridin-2-ylamine |
| "A71" | 3-[6-Fluoro-5-(4-methylpiperazin-1-yl)-1H-benzimidazol-2-yl]-5-(1-piperidin-4-yl-1H-pyrazol-4-yl)pyridin-2-ylamine |
| "A72" | 3-(5-Chloro-7-methyl-1H-benzimidazol-2-yl)-5-(1-piperidin-4-yl-1H-pyrazol-4-yl)pyridin-2-ylamine |
| "A73" | 3-(6-Fluoro-5-morpholin-4-yl-1H-benzimidazol-2-yl)-5-(1-piperidin-4-yl-1H-pyrazol-4-yl)pyridin-2-ylamine |
| "A74" | 3-(6-Fluoro-1H-benzimidazol-2-yl)-5-(1-methyl-1H-pyrazol-4-yl)pyridin-2-ylamine |
| "A75" | 5-(1-Methyl-1H-pyrazol-4-yl)-3-(4,5,6-trifluoro-1H-benzimidazol-2-yl)pyridin-2-ylamine |
| "A76" | 3-(4,6-Difluoro-1H-benzimidazol-2-yl)-5-(1-methyl-1H-pyrazol-4-yl)pyridin-2-ylamine |
| "A77" | {2-[2-Amino-5-(1-methyl-1H-pyrazol-4-yl)pyridin-3-yl]-3H-benzimidazol-5-yl}phenylmethanone |
| "A78" | 3-(6-Fluoro-5-methoxy-1H-benzimidazol-2-yl)-5-(1-methyl-1H-pyrazol-4-yl)pyridin-2-ylamine |
| "A79" | 5-(1-Methyl-1H-pyrazol-4-yl)-3-(4,5,6,7-tetrafluoro-1H-benzimidazol-2-yl)pyridin-2-ylamine |
| "A80" | {2-[2-Amino-5-(1-methyl-1H-pyrazol-4-yl)pyridin-3-yl]-3H-benzimidazol-5-yl}phenylmethanol |
| "A81" | 3-(6-Benzyl-1H-benzimidazol-2-yl)-5-(1-methyl-1H-pyrazol-4-yl)pyridin-2-ylamine |
| "A82" | 3-(6-Methoxy-1H-benzimidazol-2-yl)-5-(1H-pyrazol-4-yl)-pyridin-2-ylamine |
| "A83" | 2-[2-Amino-5-(1-methyl-1H-pyrazol-4-yl)pyridin-3-yl]-1H-benzimidazole-5-sulfonamide |
| "A84" | 5-(6-Methoxy-1H-benzimidazol-2-yl)-6'-piperazin-1-yl-[3,3']bipyridinyl-6-ylamine |
| "A85" | 3-(1H-Benzimidazol-2-yl)-5-(2H-pyrazol-3-yl)pyridin-2-ylamine |
| "A86" | 3-(1H-Benzimidazol-2-yl)-5-(2-methyl-2H-pyrazol-3-yl)pyridin-2-ylamine |
| "A87" | 3-(4-Ethoxy-1H-benzimidazol-2-yl)-5-(2H-pyrazol-3-yl)pyridin-2-ylamine |
| "A88" | 3-(4-Ethoxy-1H-benzimidazol-2-yl)-5-(1-methyl-1H-pyrazol-4-yl)pyridin-2-ylamine |
| "A89" | 3-(7-Methyl-1H-benzimidazol-2-yl)-5-(1-piperidin-4-yl-1H-pyrazol-4-yl)pyridin-2-ylamine |
| "A90" | 3-[5-(4-Methylpiperazin-1-yl)-1H-benzimidazol-2-yl]-5-(1-methyl-1H-pyrazol-4-yl)pyridin-2-ylamine |
| "A91" | Ethyl {2-[2-amino-5-(1-methyl-1H-pyrazol-4-yl)pyridin-3-yl]-1H-benzimidazol-5-yl}acetate |
| "A92" | 3-(6-Methoxy-1H-benzimidazol-2-yl)-5-(1-piperidin-4-yl-1H-pyrazol-4-yl)pyridin-2-ylamine |
| "A93" | 2-[2-Amino-5-(1-methyl-1H-pyrazol-4-yl)pyridin-3-yl]-1H-benzimidazole-4-carboxylic acid |
| "A94" | 5-[1-(2-Dimethylaminoethyl)-1H-pyrazol-4-yl]-3-(6-methoxy-1H-benzimidazol-2-yl)pyridin-2-ylamine |
| "A95" | 6'-Methoxy-5-(6-methoxy-1H-benzimidazol-2-yl)-[3,3']bipyridinyl-6-ylamine |
| "A96" | 5-[1-(3-Dimethylaminopropyl)-1H-pyrazol-4-yl]-3-(6-methoxy-1H-benzimidazol-2-yl)pyridin-2-ylamine |
| "A97" | 3-(6-Methoxy-1H-benzimidazol-2-yl)-5-(1H-pyrrol-2-yl)-pyridin-2-ylamine |
| "A98" | 3-(6-Methoxy-1H-benzimidazol-2-yl)-5-(4-methyl-3,4-dihydro-2H-pyrido[3,2-b]-1,4-oxazin-7-yl)pyridin-2-ylamine |
| "A99" | 5-(6-Methoxy-1H-benzimidazol-2-yl)-[3,3']bipyridinyl-6,6'-diamine |
| "A100" | 5-Benzo[b]thiophen-2-yl-3-(6-methoxy-1H-benzimidazol-2-yl)-pyridin-2-ylamine |
| "A101" | 5-Isoxazol-4-yl-3-(6-methoxy-1H-benzimidazol-2-yl)pyridin-2-ylamine |
| "A102" | 2-[2-Amino-5-(1-methyl-1H-pyrazol-4-yl)pyridin-3-yl]-1H-benzimidazol-4-ol |
| "A103" | 5-Benzofuran-2-yl-3-(6-methoxy-1H-benzimidazol-2-yl)-pyridin-2-ylamine |
| "A104" | 5-(6-Methoxy-1H-benzimidazol-2-yl)-N6',N6'-dimethyl-[3,3']bipyridinyl-6,6'-diamine |
| "A105" | 5-(1-Ethyl-1H-pyrazol-4-yl)-3-(6-methoxy-1H-benzimidazol-2-yl)pyridin-2-ylamine |
| "A106" | 3-(6-Methoxy-1H-benzimidazol-2-yl)-5-[1-(1-methyl-piperidin-4-yl)-1H-pyrazol-4-yl]pyridin-2-ylamine |
| "A107" | 5-(1-Isopropyl-1H-pyrazol-4-yl)-3-(6-methoxy-1H-benzimidazol-2-yl)pyridin-2-ylamine |
| "A108" | 3-(6-Methoxy-1H-benzimidazol-2-yl)-5-(1-propyl-1H-pyrazol-4-yl)pyridin-2-ylamine |
| "A109" | 5-(6-Methoxy-1H-benzimidazol-2-yl)-6'-methyl-[3,3']bipyridinyl-6-ylamine |
| "A110" | 2'-Fluoro-5-(6-methoxy-1H-benzimidazol-2-yl)-6'-methyl-[3,3']bipyridinyl-6-ylamine |
| "A111" | 6'-Amino-5'-(1H-benzimidazol-2-yl)-[3,3']bipyridinyl-6-carbonitrile |
| "A112" | N,N-Dimethyl-4-[6-amino-5-(6-methoxy-1H-benzimidazol-2-yl)pyridin-3-yl]pyrazole-1-carboxamide |
| "A113" | 3-(6-Methoxy-1H-benzimidazol-2-yl)-5-(1-thiophen-2-ylmethyl-1H-pyrazol-4-yl)pyridin-2-ylamine |
| "A114" | 3-(1H-Benzimidazol-2-yl)-5-(1-piperidin-4-yl-1H-pyrazol-4-yl)pyridin-2-ylamine |
| "A115" | 3-(1,7-Dihydroimidazo[4,5-f]indazol-6-yl)-5-(1-methyl-1H-pyrazol-4-yl)pyridin-2-ylamine |
| "A116" | 3-(5-Methoxy-1H-benzimidazol-2-yl)-5-[2-(4-methyl-piperazin-1-yl)thiazol-4-yl]pyridin-2-ylamine |
| "A117" | 3-(1H-Imidazo[4,5-b]pyridin-2-yl)-5-(1-methyl-1H-pyrazol-4-yl)pyridin-2-ylamine |
| "A118" | 3-(6-Methyl-7H-purin-8-yl)-5-(1-methyl-1H-pyrazol-4-yl)-pyridin-2-ylamine |
| "A119" | 2-{2-[2-Amino-5-(1-methyl-1H-pyrazol-4-yl)pyridin-3-yl]-1H-benzimidazol-5-yl}-N-(3,4-difluorobenzyl)acetamide |
| "A120" | 2-{2-[2-Amino-5-(1-methyl-1H-pyrazol-4-yl)pyridin-3-yl]-1H-benzimidazol-5-yl}-acetamide |
| "A121" | 2-{2-[2-Amino-5-(1-methyl-1H-pyrazol-4-yl)pyridin-3-yl]-3H-benzimidazol-5-yl}-N-methylacetamide |
| "A122" | 2-{2-[2-Amino-5-(1-methyl-1H-pyrazol-4-yl)pyridin-3-yl]-3H-benzimidazol-5-yl}-N-methylacetamide |
| "A123" | N-Isopropyl-2-[2-amino-5-(1-methyl-1H-pyrazol-4-yl)pyridin-3-yl]-3H-benzimidazole-5-carboxamide |
| "A124" | N,N-Dimethyl-2-[2-amino-5-(1-methyl-1H-pyrazol-4-yl)pyridin-3-yl]-3H-benzimidazole-5-carboxamide |
| "A125" | tert-Butyl 4-({2-[2-amino-5-(1-methyl-1H-pyrazol-4-yl)pyridin-3-yl]-3H-benzimidazole-5-carbonyl}amino)-piperidine-1-carboxylate |

| Compound No. | Name and/or structure |
|---|---|
| "A126" | N-Piperidin-4-yl-2-[2-amino-5-(1-methyl-1H-pyrazol-4-yl)-pyridin-3-yl]-3H-benzimidazole-5-carboxamide |
| "A127" | N-(2-Methoxyethyl)-2-[2-amino-5-(1-methyl-1H-pyrazol-4-yl)-pyridin-3-yl]-1H-benzimidazole-4-carboxamide |
| "A128" | N-[2-(3,4-Difluorophenyl)ethyl]-2-[2-amino-5-(1-methyl-1H-pyrazol-4-yl)pyridin-3-yl]-3H-benzimidazole-5-carboxamide |
| "A129" | N-Piperidin-4-yl-2-[2-amino-5-(1-methyl-1H-pyrazol-4-yl)-pyridin-3-yl]-1H-benzimidazole-4-carboxamide |
| "A130" | N-(2-Methoxyethyl)-5-[6-amino-5-(6-methoxy-1H-benzimidazol-2-yl)pyridin-3-yl]thiophene-2-carboxamide |
| "A131" | N-(2-Dimethylaminoethyl)-5-[6-amino-5-(6-methoxy-1H-benzimidazol-2-yl)pyridin-3-yl]thiophene-2-carboxamide |
| "A132" | N-Piperidin-4-yl-5-[6-amino-5-(6-methoxy-1H-benzimidazol-2-yl)pyridin-3-yl]thiophene-2-carboxamide |
| "A133" | N-(1-Methylpiperidin-4-yl)-5-[6-amino-5-(6-methoxy-1H-benzimidazol-2-yl)pyridin-3-yl]thiophene-2-carboxamide |
| "A134" | N-(Pyridin-4-ylmethyl)-5-[6-amino-5-(6-methoxy-1H-benzimidazol-2-yl)pyridin-3-yl]thiophene-2-carboxamide |
| "A135" | N-(2-{2-[2-Amino-5-(1-methyl-1H-pyrazol-4-yl)pyridin-3-yl]-3H-benzimidazol-5-yl}ethyl)-3,4-difluorobenzamide |
| "A136" | 2-{2-[2-Amino-5-(1-methyl-1H-pyrazol-4-yl)pyridin-3-yl]-3H-benzimidazol-4-yl}ethanol |
| "A137" | 3-[5-(4-Methylpiperazine-1-sulfonyl)-1H-benzimidazol-2-yl]-5-(1-methyl-1H-pyrazol-4-yl)pyridin-2-ylamine |
| "A138" | N,N-Dimethyl-2-[2-amino-5-(1-methyl-1H-pyrazol-4-yl)pyridin-3-yl]-3H-benzimidazole-5-sulfonamide |
| "A139" | N-Ethyl-2-[2-amino-5-(1-methyl-1H-pyrazol-4-yl)pyridin-3-yl]-1H-benzimidazole-5-sulfonamide |
| "A140" | N-(Pyridin-4-ylmethyl)-2-[2-amino-5-(1-methyl-1H-pyrazol-4-yl)pyridin-3-yl]-5-fluoro-3H-benzimidazole-4-carboxamide |
| "A141" | Ethyl 2-[2-amino-5-(1-methyl-1H-pyrazol-4-yl)pyridin-3-yl]-5-fluoro-3H-benzimidazol-4-carboxylate |
| "A142" | 2-[2-Amino-5-(1-methyl-1H-pyrazol-4-yl)pyridin-3-yl]-5-fluoro-3H-benzimidazole-4-carboxylic acid |
| "A143" | 1-{2-[2-Amino-5-(1-methyl-1H-pyrazol-4-yl)pyridin-3-yl]-1H-benzimidazol-5-yl}-1-phenylethanol |
| "A144" | 3-(6-Methoxy-1H-benzimidazol-2-yl)-5-thiophen-3-yl-pyridin-2-ylamine |
| "A145" | 5-Imidazol-1-yl-3-(5-methoxy-1H-benzimidazol-2-yl)pyridin-2-ylamine |
| "A146" | 4-{2-[2-Amino-5-(1-methyl-1H-pyrazol-4-yl)pyridin-3-yl]-3H-benzimidazol-5-yl}morpholin-3-one |
| "A147" | 3-{2-[2-Amino-5-(1-methyl-1H-pyrazol-4-yl)pyridin-3-yl]-1H-benzimidazol-5-yl}-1,3-oxazinan-2-one |
| "A148" | 3-(5-Fluoro-6-methoxy-1H-benzimidazol-2-yl)-5-[1-(2-morpholin-4-ylethyl)-1H-pyrazol-4-yl]pyridin-2-ylamine |
| "A149" | 1-{2-[2-Amino-5-(1-piperidin-4-yl-1H-pyrazol-4-yl)pyridin-3-yl]-1H-benzimidazol-5-yl}-1-phenylethanol |
| "A150" | 1-(2-{2-Amino-5-[1-(2-morpholin-4-ylethyl)-1H-pyrazol-4-yl]pyridin-3-yl}-1H-benzimidazol-5-yl)-1-phenylethanol | and pharmaceutically usable salts, tautomers and stereoisomers thereof, including mixtures thereof in all ratios.

13. Process for the preparation of compounds of the formula I according to claim 1 and pharmaceutically usable salts, tautomers and stereoisomers thereof, characterised in that a) a compound of the formula II

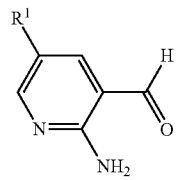

in which $R^1$ has the meaning indicated in claim 1, is reacted with a compound of the formula III

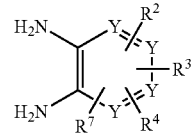

in which Y, $R^2$, $R^3$, $R^4$, $R^7$ have the meanings indicated in claim 1, or b) a compound of the formula IV

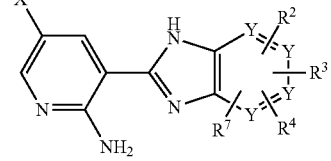

in which Y, $R^2$, $R^3$, $R^4$, $R^7$ have the meanings indicated in claim 1 and X denotes Br or I,
is reacted with a compound of the formula V $R^1$-L          V in which $R^1$ has the meaning indicated in claim 1 and L denotes a boronic acid or boronic acid ester radical, and/or a base or acid of the formula I is converted into one of its salts.

14. A pharmaceutical composition comprising at least one compound of the formula I according to claim 1 and/or pharmaceutically usable salts, tautomers and stereoisomers thereof, including mixtures thereof in all ratios, and optionally excipients and/or adjuvants.

* * * * *

UNITED STATES PATENT AND TRADEMARK OFFICE
CERTIFICATE OF CORRECTION

PATENT NO. : 8,648,201 B2  
APPLICATION NO. : 13/383605  
DATED : February 11, 2014  
INVENTOR(S) : Calderini et al.

Page 1 of 1

It is certified that error appears in the above-identified patent and that said Letters Patent is hereby corrected as shown below:

In the claims

Column 120, line 25 reads "$(R^5)_2]_nN(R^5)_2, NR^5CONR^5[C(R^5)_2]_1Het^1, OCONR^5[C$"  
should read -- $(R^5)_2]_nN(R^5)_2, NR^5CONR^5[C(R^5)_2]_nHet^1, OCONR^5[C$ --

Column 120, line 26 reads "$(R^5)_2]_nN(R^5)_2, OCONR^5[C(R^5)_2]_nHet^1, [C(R^5)_2]_nR^5,$"  
should read -- $(R^5)_2]_nN(R^5)_2, OCONR^5[C(R^5)_2]_nHet^1, [C(R^5)_2]_n OR^5,$ --

Column 120, line 37 reads "$COOR^5, [C(R^5)_2]_nCONR^5[C(R^5)_2]_nAr, [C(R^5)_2]$"  
should read -- $COOR^5, [C(R^5)_2]_nCONR^5[C(R^5)_2]_nAr, [C(R^5)_2]_n$ --

Column 120, line 39 reads "$[C(R^5)_2]_1COO[C(R^5)_2]_nHet, [C(R^5)_2]_nNR^5CO[C$"  
should read -- $[C(R^5)_2]_nCOO[C(R^5)_2]_nHet, [C(R^5)_2]_nNR^5CO[C$ --

Column 121, line 5 reads "$(R^5)_2]-Het^1, CO-Het^1, CHO, COA, =S, =NH, =NA$"  
should read -- $(R^5)_2]_n-Het^1, CO-Het^1, CHO, COA, =S, =NH, =NA$ --

Signed and Sealed this  
First Day of July, 2014

Michelle K. Lee  
*Deputy Director of the United States Patent and Trademark Office*